US010830780B2

(12) United States Patent
Giese et al.

(10) Patent No.: US 10,830,780 B2
(45) Date of Patent: Nov. 10, 2020

(54) APPARATUS AND METHODS FOR SAMPLE ANALYSIS AND CLASSIFICATION BASED ON TERPENES AND CANNABINOIDS IN THE SAMPLE

(71) Applicant: Biotech Institute, LLC, Westlake Village, CA (US)

(72) Inventors: Matthew W. Giese, Westlake Village, CA (US); Mark Anthony Lewis, Westlake Village, CA (US)

(73) Assignee: Biotech Institute, LLC, Westlake Village, CA (US)

( * ) Notice: Subject to any disclaimer, the term of this patent is extended or adjusted under 35 U.S.C. 154(b) by 346 days.

(21) Appl. No.: 15/539,346

(22) PCT Filed: Jan. 27, 2016

(86) PCT No.: PCT/US2016/015011
§ 371 (c)(1),
(2) Date: Jun. 23, 2017

(87) PCT Pub. No.: WO2016/123160
PCT Pub. Date: Aug. 4, 2016

(65) Prior Publication Data
US 2018/0284145 A1 Oct. 4, 2018

Related U.S. Application Data

(60) Provisional application No. 62/107,652, filed on Jan. 26, 2015.

(51) Int. Cl.
*G01N 33/94* (2006.01)
*G01N 30/68* (2006.01)
*G01N 30/88* (2006.01)
*G01N 30/02* (2006.01)

(52) U.S. Cl.
CPC .......... *G01N 33/948* (2013.01); *G01N 30/68* (2013.01); *G01N 2030/025* (2013.01); *G01N 2030/027* (2013.01); *G01N 2030/884* (2013.01)

(58) Field of Classification Search
CPC .............................. G01N 33/94; G01N 30/68
USPC .......................................................... 436/93
See application file for complete search history.

(56) References Cited

U.S. PATENT DOCUMENTS

| | | | |
|---|---|---|---|
| 4,279,824 A | 7/1981 | McKinney | |
| 5,252,490 A * | 10/1993 | ElSohly | G01N 33/02 436/161 |
| 5,532,131 A | 7/1996 | Lewis | |
| 5,757,659 A | 5/1998 | Arai et al. | |
| 6,403,126 B1 | 6/2002 | Webster et al. | |
| 6,439,027 B1 | 8/2002 | Hiss | |
| 6,466,929 B1 | 10/2002 | Brown et al. | |
| 6,630,507 B1 | 10/2003 | Hampson et al. | |
| 6,635,490 B1 * | 10/2003 | Fu | A61K 31/7048 436/94 |
| 7,117,188 B2 | 10/2006 | Guyon et al. | |
| 7,968,594 B2 | 6/2011 | Guy et al. | |
| 8,402,027 B1 | 3/2013 | Dange et al. | |
| 8,445,034 B1 * | 5/2013 | Coles, Jr. | A61K 31/05 424/725 |
| 9,095,554 B2 | 8/2015 | Lewis et al. | |
| 9,370,164 B2 | 6/2016 | Lewis et al. | |
| 9,394,510 B2 * | 7/2016 | Peet | C12M 41/30 |
| 9,642,317 B2 | 5/2017 | Lewis et al. | |
| 10,319,475 B1 * | 6/2019 | Croan | G06F 19/3456 |
| 2003/0021752 A1 * | 1/2003 | Whittle | A61K 9/0031 424/45 |
| 2004/0034108 A1 * | 2/2004 | Whittle | A61K 9/006 514/772 |
| 2004/0049059 A1 | 3/2004 | Mueller | |
| 2004/0192760 A1 * | 9/2004 | Whittle | A61K 9/0031 514/454 |
| 2005/0165088 A1 * | 7/2005 | Whittle | A61K 31/05 514/454 |
| 2005/0266108 A1 | 12/2005 | Flockhart et al. | |
| 2006/0100245 A1 | 5/2006 | Bakthavatchalam et al. | |
| 2006/0160888 A1 | 7/2006 | Kottayil et al. | |

(Continued)

FOREIGN PATENT DOCUMENTS

GB 2459125 A 10/2009
WO WO 2011/110866 A1 9/2011

(Continued)

OTHER PUBLICATIONS

Turner, C. E. et al, Journal of Natural Products 1979, 42, 317-319.*
Martin, B. R., Pharmacological Reviuews 1986, 38, 45-74.*
Compton, D. R. et al, Journal of Pharmacology and Experimental Theraputics 1992, 260, 201-209.*
ElSohly, M. A. Journal of Forensic Sciences 2000, 45, 24-30.*
Gambaro, V. et al, Analytica Chimica Acta 2002, 468, 245-254.*
Mehmedic, Z. et al, Journal of Forensic Sciences 2010, 55, 1209-1217.*
Brosues, J. et al, Forensic Science International 2010, 200, 87-92.*
Giese, M. W. et al, Journal of AOAC International 2015, 98, 1503-1522.*

(Continued)

*Primary Examiner* — Arlen Soderquist
(74) *Attorney, Agent, or Firm* — Cooley LLP

(57) ABSTRACT

The disclosure relates to systems, apparatuses, and methods for estimating a terpene level of two or more terpenes of the plurality of terpenes in the sample to generate a set of terpene levels; and/or estimating a cannabinoid level of two or more cannabinoids of the plurality of cannabinoids in the sample to generate a set of cannabinoid levels; configured to store a set of groups and classify the sample to a group of the set of groups, based on said terpene and cannabinoid levels. The present disclosure also relates to systems, apparatuses, and methods configured to generate entourage effect values and organoleptic values, based on said cannabinoid and terpene levels.

21 Claims, 13 Drawing Sheets

(56) References Cited

U.S. PATENT DOCUMENTS

| | | | |
|---|---|---|---|
| 2007/0077660 A1* | 4/2007 | Glas | G01N 30/90 |
| | | | 436/93 |
| 2008/0103193 A1 | 5/2008 | Castor et al. | |
| 2008/0241339 A1 | 10/2008 | Mitchell et al. | |
| 2009/0035396 A1 | 2/2009 | De Meijer | |
| 2010/0216872 A1 | 8/2010 | Letzel et al. | |
| 2011/0098348 A1 | 4/2011 | De Meijer | |
| 2011/0320135 A1 | 12/2011 | van de Voort et al. | |
| 2012/0052535 A1 | 3/2012 | Lange et al. | |
| 2012/0131701 A1* | 5/2012 | Shekdar | C12Q 1/6895 |
| | | | 800/298 |
| 2012/0311744 A1 | 12/2012 | Sirkowski | |
| 2013/0109747 A1 | 5/2013 | Whittle | |
| 2013/0334045 A1* | 12/2013 | Kuhr | G01N 1/22 |
| | | | 204/435 |
| 2013/0337477 A1* | 12/2013 | Kuhr | G01N 1/22 |
| | | | 435/7.92 |
| 2014/0088884 A1 | 3/2014 | Friedenberg et al. | |
| 2014/0235474 A1* | 8/2014 | Tang | C12Q 1/6869 |
| | | | 506/9 |
| 2014/0243405 A1 | 8/2014 | Whalley | |
| 2014/0245494 A1 | 8/2014 | Cohen | |
| 2014/0245495 A1 | 8/2014 | Cohen | |
| 2014/0271940 A1 | 9/2014 | Wurzer | |
| 2014/0287068 A1 | 9/2014 | Lewis et al. | |
| 2014/0298511 A1 | 10/2014 | Lewis | |
| 2014/0324660 A1 | 10/2014 | Bolno et al. | |
| 2015/0080265 A1* | 3/2015 | Elzinga | C11B 9/0038 |
| | | | 506/15 |
| 2015/0219610 A1* | 8/2015 | Jackson, Jr. | G01N 33/0098 |
| | | | 707/770 |
| 2015/0225482 A1* | 8/2015 | Song | C12N 15/635 |
| | | | 530/387.3 |
| 2015/0305651 A1* | 10/2015 | Attariwala | A61B 5/082 |
| | | | 600/532 |
| 2015/0359188 A1 | 12/2015 | Lewis et al. | |
| 2015/0366154 A1 | 12/2015 | Lewis et al. | |
| 2016/0139055 A1* | 5/2016 | Pierce, III | G01N 21/84 |
| | | | 356/326 |
| 2016/0264917 A1* | 9/2016 | Peet | C12M 41/30 |
| 2016/0300289 A1* | 10/2016 | Rose | G06Q 30/0631 |
| 2016/0324091 A1 | 11/2016 | Lewis et al. | |
| 2017/0202170 A1 | 7/2017 | Lewis et al. | |
| 2018/0064055 A1 | 3/2018 | Lewis et al. | |
| 2018/0143212 A1* | 5/2018 | Giese | A61K 36/185 |
| 2018/0224411 A1 | 8/2018 | Raber et al. | |

FOREIGN PATENT DOCUMENTS

| | | |
|---|---|---|
| WO | WO 2013/155553 A1 | 10/2013 |
| WO | WO 2014/145490 A2 | 9/2014 |
| WO | WO 2015/065544 A1 | 5/2015 |
| WO | WO 2016/105514 A1 | 6/2016 |
| WO | WO 2016/123160 A1 | 8/2016 |

OTHER PUBLICATIONS

STICKYGuide "A Guide to the StickyType Cannabis Classification System" 2011, 3 pages, downloaded Dec. 12, 2019 from https://www.stickyguide.com/blog/a-guide-to-the-stickytype-cannabis-classification-system.*

Habib, R. et al, Report I-502 Project $430-1c, 2013, 37 pages.*

Aberl and Coelhan, "Determination of Volatile Compounds in Different Hop Varieties by Headspace-Trap GC/MS—In Comparison with Conventional Hop Essential Oil Analysis." J. Agric. Food Chem. (2012); 60 (11): 2785-2792.

Agilent Technologies, Inc. "Consideration for Selecting GC/MS or LC/MS for Metabiomics", Feb. 24, 2007, 4 pages.

Analytical 360 Analysis of Critical Mass on Aug. 25, 2014, http://analytical360.com/m/expired/276599, 5 pages.

Analytical 360 analysis of Sweet & Sour Widow CBD on Nov. 2, 2013, http://analytical360.com/m/expired/131803, 4 pages.

Analytical 360 Analysis of Sweet n' Sour Widow on May 8, 2014, http://analytical360.com/m/expired/230612, 4 pages.

AOAC® Peer-Verified Methods Program, Manual on Policy and Procedures (1998); Arlington, VA, 35 pages.

Bertoli, A., et al., "Fibre hemp inflorescences: From crop-residues to essential oil production", Industrial Crops and Products, Nov. 1, 2010, pp. 329-337, vol. 32, No. 3.

Casano et al., "Variations in Terpene Profiles of Different Strains of Cannabis sativa L." Acta Horticulturae, vol. 925, pp. 115-121, 2011.

CBD Crew "About Us" Printed copy provided as published on Apr. 10, 2012. URL: http://cbdcrew.org/about-us/, 3 pages.

CBD Crew "Varieties" printed copy as published on Mar. 20, 2012 URL: http://cbdcrew.org/varieties/, 2 pages.

CBD Crew Analysis Report; (Critical Mass, Fundacion CANNA; Mar. 21, 2012), pp. 1-2, http://cbdcrew.org/varieties/cbd-critical-mass/.

CBD Crew Sweet and Sour Widow analysis published Nov. 2, 2013, pp. 1-5, http://analytical360.com/m/expired/131803.

CBD Crew variety "Sweet and Sour Widow" retrieved from the internet: https://web.archive.org/web/20120409021918/http://cbdcrew.org/varieties/cbd-sweet-and-sour-widow/, published on Apr. 9, 2012, retrieved on Mar. 10, 2017, 2 pages.

CBD Crew Web Pub; (Critical Mass sample available from Northwest Canna Connection; Feb. 26, 2014, pp. 1-5. http://analytical360.com/m/expired/197158.

CBD-crew front page on Nov. 22, 2014. www.cbdcrew.org, 2 pages.

Da Silva, et al., "Biological Activities of a-Pinene and β-Pinene Enantiomers." Molecules (2012); 17(6): 6305-6316.

Davies, et al., "Metabolome variability in crop plant species—When, where, how much and so what?" Regulatory Toxicology and Pharmacology (2010); 58(3-Supplement 1): S54-S61.

De Backer, et al., "Innovative development and validation of an HPLC/DAD method for the qualitative and quantitative determination of major cannabinoids in cannabis plant material." Journal of Chromatography B (2009); 877(32): 4115-4124.

De Meijer and Hammond, "The inheritance of chemical phenotype in Cannabis sativa L. (V): regulation of the propyl-/pentyl cannabinoid ratio, completion of a genetic model." Euphytica (2016); 210: 291-307.

De Meijer et al., 2003, "The Inheritance of Chemical Phenotype in Cannabis sativa L." Genetics, 163: 335-346.

De Meijer et al., 2005, "The Inheritance of Chemical Phenotype in Cannabis sativa L. (II) Cannabigerol Predominant Plants." Euphytica, 145:189-198.

De Meijer et al., 2009, "The Inheritance of chemical phenotype in Cannabis sativa L. (III) Variation in Cannabichromene Proportion", Euphytica, 165:293-311.

De Meijer et al., 2009, "The Inheritance of Chemical Phenotype in Cannabis sativa L. (IV) Cannabinoid-Free Plants", Euphytica, 168:95-112.

Do Vale, et al., "Central effects of citral, myrcene and limonene, constituents of essential oil chemotypes from Lippia alba (Mill.) N.E. Brown." Phytomedicine (2002); 9(8): 709-714.

Dussy, F.E., et al., "Isolation of $\Delta^9$-THCA-A from hemp and analytical aspects concerning the determination of $\Delta^9$-THC in cannabis products." Forensic Science International (2005); 149(a): 3-10.

Elsohly and Gul, "Constituents of Cannabis Sativa." Handbook of Cannabis (R.G. Pertwee (Eds), Oxford University Press, Oxford, UK. pp. 3-22.

Fischedick, J. et al., "Metabolic fingerprinting of Cannabis sativa L., cannabinoids and terpenoids for chemotaxonomic and drug standardization purposes" Phytochemistry 2010, vol. 71., pp. 2058-2073.

G. of Vancouver Island Seed Company, "How to make Clones", Cannabis Culture Magazine published on Tuesday, Apr. 29, 2009, 58 pages. Available online at http://www.cannabisculture.com/content/how-make-clones.

Grotenhermen, F., "Clinical Pharmacokinetics of Cannabinoids." Journal of Cannabis Therapeutics (2002); 3(1): 3-51.

Halent Laboratories "Test Results for Dougie's Farm H0-21", Test ID# 2960-1, Feb. 14, 2013, 5 pages.

(56) References Cited

OTHER PUBLICATIONS

Halent Labs Chemical Analysis for "Pineapple Purps" retrieved from the internet: http://steephilllab.com/thcv-the-sports-car-of-cannabinoids/, retrieved on Mar. 17, 2017, 1 page.

Hazekamp, A., Cannabis: Extracting the Medicine, Proefschrift Universiteit Leiden, Amsterdam, The Netherlands, (2007), pp. 91-106, 187 pages.

International PCT Search Report for PCT/US2014/030267, dated Nov. 7, 2014, 6 pages.

International PCT Search Report for PCT/US2014/046694, dated Jan. 5, 2015, 7 pages International Preliminary Report on Patentability for International Application No. PCT/US2014/030267 dated Sep. 15, 2015, 10 pages.

International Preliminary Report on Patentability for International Application No. PCT/US2014/046694 dated May 3, 2016, 11 pages.

International Preliminary Report on Patentability for International Application No. PCT/US2015/000263, dated Jun. 27, 2017, 8 pages.

International Preliminary Report on Patentability for International Application No. PCT/US2016/015011, dated Aug. 1, 2017, 15 pages.

International Search Report and Written Opinion for International Application No. PCT/US2015/000263, dated Mar. 4, 2016, 8 pages.

International Search Report and Written Opinion for International Application No. PCT/US2016/015011, dated Apr. 8, 2016, 16 pages.

Kojoma, M. et al., "DNA polymorphisms in the tetrahydrocannabinolic acid (THCA) synthase gene in "drug-type" and "fiber-type" Cannabis sativa L", Forensic Science International, Jun. 2, 2006, pp. 132-140, vol. 159, No. 2-3, Elsevier Scientific Publishers Ireland Ltd.

Kulkarni and Rathod, "Mapping of an ultrasonic bath for ultrasound assisted extraction of mangiferin from Mangifera indica leaves." Ultrasonics Sonochemistry (2014); 21(2): 606-611.

McPartland and Russo 2001 "Cannabis and Cannabis Extracts: Greater Than the Sum of Their Parts", Journal of Cannabis Therapeutics vol. 1, No. 3/4,2001, pp. 103-132.

Pertwee, RG. 2008 "The diverse $CB_1$ and $CB_2$ receptor pharmacology of three plant cannabinoids: $\Delta^9$ tetrahydrocannabinol, cannabidiol and $\Delta^9$ tetrahydrocannabivarin" Br. J Pharmacol. 153(2):199-215.

Rao, et al., "Effect of myrcene on nociception in mice." Journal of Pharmacy and Pharmacology (1990); 42(12): 877-878.

Restek ChromaBLOGraphy, https://blog.restek.com/?p=11770, Mar. 25, 2014, accessed Oct. 26, 2017, 7 pages.

Russo and Guy, "A tale of two cannabinoids: the therapeutic rationale for combining tetrahydrocannabinol and cannabidiol", Medical Hypothesis, 2006, 66:234-246.

Russo, E.B., "Taming THC: potential cannabis synergy and phytocannabinoid-terpenoid entourage effects" The British Journal of Pharmacology, 2011, pp. 1344-1364, vol. 163.

Satyal, P. et al. "Chemotyping and Determination of Antimicrobial Insecticidal, and Cytotoxic Properties of Wild Grown Cannabis saliva from Nepal" Journal of Medicinally Active Plants, Dec. 2014, vol. #3, Issue 1, pp. 9-16.

Seedsman Listing of "Sweet and Sour Widow", on May 21, 2013, http://web.archive.org/web/20130521045347/http://www.seedsman.com/en/cbd-sweet-n-sour-widow-regular-5-seeds, 3 pages.

Solon, Olivia, "Medical Marijuana Without the High", Jul. 5, 2012, retrieved from the internet: www.wired.com.

Steep Hill Halent Cannabis Analytics and Research: "Dougs Varin Decarb THCV Std.", Steep Hill Labs, Inc., Reported Jun. 10, 2014, retrieved from the internet: http://steephilllab.com/wp-content/uploads/2014/07/DougsVarinKief_Decarbed.pdf, retrieved on Mar. 17, 2017, 3 pages.

Steep Hill Halent Cannabis Analytics and Research: "Dougs Varin THCVA Std.", Steep Hill Labs, Inc., Reported Jun. 10, 2014, retrieved from the internet: http://steephilllab.com/wp-content/uploads/2014/07/DougsVarinKief.pdf, retrieved on Mar. 17, 2017, 3 pages.

Swift, et al., "Analysis of Cannabis Seizures in NSW, Australia: Cannabis Potency and Cannabinoid Profile." PLOS One (2013); 7: 1-9.

The Werc Shop Terpene Profiling Services, Aug. 26, 2012. http://web.archive.org/web/20120826071723/http://thewercshop.com/services/terpene-profiling-services, 4 pages.

Van Bakel, et al. "The draft genome and transcriptome of Cannabis sativa", Genome Biology, Oct. 20, 2011, p. R102, vol. 12, No. 10, Biomed Central Ltd., London, GB.

Waksmundzka-Hajnos and Monika, "High Performance Liquid Chromatography in Phytochemical Analysis (Chromatograhic Science Series)." Published May 14, 2012. p. 582 provided.

Written Opinion for International Application No. PCT/US2014/030267 dated Nov. 7, 2014, 9 pages.

Written Opinion for International Application No. PCT/US2014/046694 dated May 1, 2015, 10 pages.

Upton et al. (eds.), "Cannabis Inflorescence and Leaf," Preview Copy, American Herbal Pharmacopoeia, 2013, AHP, Scott's Valley, CA, pp. 1, 2, 5, 7, 11, 31, 32, 38, 42, 45, 46, 50, 55.

Analytical 360, Test results for "Nordle", Jun. 22, 2013 (Jun. 22, 2013), retrieved from the internet: http://archive.analytical360.com/m/archived/79871, retrieved on May 29, 2019, 4 pages.

Analytical 360, Test results for "Nordle", Jan. 8, 2014 (Jan. 8, 2014), retrieved from the internet: http://archive.analytical360.com/m/archived/166950, retrieved on May 29, 2019, 4 pages.

Analytical 360 Analysis of Girl Scout Cookie (Patient Solutions) on Jun. 23, 2014, https://web.archive.org/web/20140628182810/http://analytical360.com/m/flowers/251990, 3 pages.

Analytical 360 Analysis of Omrita Rx on Feb. 20, 2014, http://archive.analytical360.com/m/archived/192732, 3 pages.

Booth et al., "Terpene synthases from Cannabis sativa," PLoS One (2017) 12(3): e0173911, 20 pages.

Elsohly, M.A., et al., "Constituents of Cannabis sativa L. XXIV: The Potency of Confiscated Marijuana, Hashish, and Hash Oil Over a Ten-Year Period," Journal of Forensic Sciences, 1984; vol. 29, No. 2, pp. 500-514, 15 pages.

Gieringer, D., "Cannabis "Vaporization": A Promising Strategy for Smoke Harm Reduction." Journal of Cannabis Therapeutics (2001); 1 (3-4): 153-170.

Grotenhermen et al., "The therapeutic potential of cannabis and cannabinoids", Dtsch Arztebl Int., vol. 109, No. 29-30, pp. 495-501, 2012.

Hazekamp and Fischedick, "Cannabis—from cultivar to chemovar", Drug Testing and Analysis, vol. 4, pp. 660-667, 2012, published online Feb. 24, 2012 (Feb. 24, 2012).

Hillig, "A chemotaxonomic analysis of terpenoid variation in Cannabis," Biochemical Systematics and Ecology (2004), 32:875-891.

Ito et al., "The sedative effect of inhaled terpinolene in mice and its structure-activity relationships," Journal of Natural Medicines, 2013, vol. 67, Issue 4, pp. 833-837, published online Jan. 22, 2013 (Jan. 22, 2013).

Klingeren and Ham, "Antibacterial activity of $\Delta^9$-tetrahydrocannabinol and cannabidiol", Antonie van Leeuwenhoek (1976); 42 (1-2): 9-12.

Okumura et al., "Terpinolene, a component of herbal sage, downregulates AKT1 expression in K562 cells", Oncology Letters, vol. 3, pp. 321-324, 2012.

Pertwee, RG., "Emerging strategies for exploiting cannabinoid receptor agonists as medicines." Br J Pharmacol. (2009); 156 (3): 397-411.

Pure Analytics LLC, "How THC and CBD Work Together," Web document, Feb. 19, 2012, 5 pages.

* cited by examiner

APPARATUS AND METHODS FOR SAMPLE ANALYSIS AND CLASSIFICATION BASED ON TERPENES AND CANNABINOIDS IN THE SAMPLE

CROSS-REFERENCE TO RELATED APPLICATIONS

This application is the National Stage of International Application No. PCT/US2016/015011, filed Jan. 27, 2016, which in turn claims priority to U.S. Provisional Application No. 62/107,652, filed on Jan. 26, 2015, each of which is hereby incorporated by reference in its entirety for all purposes.

FIELD

The present disclosure relates to methods for classifying analytical data. In some embodiments, the analytical data is derived from *cannabis*, such as medical and recreational *cannabis*, based on their psychoactive, medical, entourage, organoleptic properties, etc.

BACKGROUND

Traditional classification schemes are based on morphological characteristics, and are not able to account for the substantial amount of chemical diversity within similar looking lines. That is, historical classification approaches that are currently used for plant products (e.g., for *cannabis*) requires manual study of plant form, and fails to account for the breath of psychoactive, medical, entourage, and organoleptic range of parameters associated with the plant products.

Thus, there is a great need in the art for the development of improved, chemical-based classification that does not suffer from the drawbacks of current approaches.

SUMMARY OF THE DISCLOSURE

In some embodiments, the present disclosures teaches a kit, comprising: a chemical analyzer configured to: receive a sample, the sample including a plurality of terpenes; and chemically analyze the sample, including a) estimating a terpene level of two or more terpenes of the plurality of terpenes in the sample to generate a set of terpene levels; and a computing apparatus operatively coupled to the chemical analyzer, the computing apparatus including: a memory configured to receive and store the set of terpene levels, the memory further configured to store a set of groups; and a processor configured to, based on the set of terpene levels, classify the sample to a group of the set of groups In some embodiments, the present disclosures teaches a kit, comprising: a chemical analyzer configured to: receive a sample, the sample including a plurality of terpenes and a plurality of cannabinoids; and chemically analyze the sample, including a) estimating a terpene level of two or more terpenes of the plurality of terpenes in the sample to generate a set of terpene levels; b) estimating a cannabinoid level of two or more cannabinoids of the plurality of cannabinoids in the sample to generate a set of cannabinoid levels; and c) a computing apparatus operatively coupled to the chemical analyzer, the computing apparatus including: a memory configured to receive and store the set of terpene levels and cannabinoid levels, the memory further configured to store a set of groups; and a processor configured to, based on the set of terpene levels and cannabinoid levels, classify the sample to a group of the set of groups.

In some embodiments disclosed herein, the chemical analyzer includes one or more of a high performance liquid chromatography (HPLC) analyzer or gas chromatography flame ionization detection (GC-FID) analyzer.

In some embodiments disclosed herein, the sample comprises one or more *cannabis* species, each *cannabis* species selected from the group consisting of *Cannabis sativa*, *Cannabis indica*, and *Cannabis ruderalis*.

In some embodiments disclosed herein, the processor is further configured to classify the sample based on a highest terpene level of the set of terpene levels.

In some embodiments disclosed herein, the processor can be further configured to classify the sample based on two or more terpene levels of the set of terpene levels, the two or more terpene levels including a first terpene level and a second terpene level, the first terpene level being the highest terpene level of the set of terpene levels, the second terpene level being lesser than the first terpene level and greater than a remainder of the set of terpene levels.

In some embodiments disclosed herein, the processor can be further configured to classify the sample based on three or more terpene levels of the set of terpene levels, the three or more terpene levels including a first terpene level, a second terpene level, and a third terpene level; the first terpene level being the highest terpene level of the set of terpene levels, the second terpene level being lesser than the first terpene level and greater than a remainder of the set of terpene levels, and the third terpene level being lesser than the first and second terpene levels, and greater than a remainder of the set of terpene levels.

In some embodiments disclosed herein, the processor is further configured to classify the sample based on a highest cannabinoid level of the set of cannabinoid levels.

In some embodiments disclosed herein, the processor can be further configured to classify the sample based on two or more cannabinoid levels of the set of cannabinoid levels, the two or more cannabinoid levels including a first cannabinoid level and a second cannabinoid level, the first cannabinoid level being the highest cannabinoid level of the set of cannabinoid levels, the second cannabinoid level being lesser than the first cannabinoid level and greater than a remainder of the set of cannabinoid levels.

In some embodiments, the present disclosure teaches an apparatus, comprising: a chemical analyzer configured to: receive a sample, the sample including a plurality of terpenes; chemically analyze the sample, including estimating a terpene level of two or more terpenes of the plurality of terpenes in the sample to generate a set of terpene levels; a classifier implemented in a memory or a processing device, the classifier communicably coupled to the chemical analyzer, the classifier configured to, based on the set of terpene levels, classify the sample to a group of a set of groups.

In some embodiments, the present disclosure teaches an apparatus, comprising: a chemical analyzer configured to: receive a sample, the sample including a plurality of terpenes and a plurality of cannabinoids; chemically analyze the sample, including estimating a terpene level of two or more terpenes of the plurality of terpenes in the sample to generate a set of terpene levels, and estimating a cannabinoid level of two or more cannabinoids of the plurality of cannabinoids in the sample to generate a set of cannabinoid levels; a classifier implemented in a memory or a processing device, the classifier communicably coupled to the chemical analyzer, the classifier configured to, based on the set of terpene levels and the set of cannabinoid levels, classify the sample to a group of a set of groups.

In some embodiments disclosed herein, the chemical analyzer includes one or more of a high performance liquid chromatography (HPLC) analyzer or gas chromatography flame ionization detection (GC-FID) analyzer.

In some embodiments disclosed herein, the sample includes one or more *cannabis* species, each *cannabis* species selected from the group consisting of *Cannabis sativa, Cannabis indica*, and *Cannabis ruderalis*.

In some embodiments disclosed herein, the sample includes a *cannabis* extract.

In some embodiments disclosed herein, the classifier is further configured to classify the sample based on a highest terpene level of the set of terpene levels.

In some embodiments disclosed herein, the classifier is further configured to classify the sample based on two or more terpene levels of the set of terpene levels, the two or more terpene levels including a first terpene level and a second terpene level, the first terpene level being the highest terpene level of the set of terpene levels, the second terpene level being lesser than the first terpene level and greater than a remainder of the set of terpene levels.

In some embodiments disclosed herein, the classifier is further configured to classify the sample based on three or more terpene levels of the set of terpene levels, the three or more terpene levels including a first terpene level, a second terpene level, and a third terpene level, the first terpene level being the highest terpene level of the set of terpene levels, the second terpene level being lesser than the first terpene level and greater than a remainder of the set of terpene levels, and the third terpene level being lesser than the first and second terpene levels, and greater than a remainder of the set of terpene levels.

In some embodiments disclosed herein, the classifier is further configured to classify the sample based on a highest cannabinoid level of the set of cannabinoid levels.

In some embodiments disclosed herein, the classifier can be further configured to classify the sample based on two or more cannabinoid levels of the set of cannabinoid levels, the two or more cannabinoid levels including a first cannabinoid level and a second cannabinoid level, the first cannabinoid level being the highest cannabinoid level of the set of cannabinoid levels, the second cannabinoid level being lesser than the first cannabinoid level and greater than a remainder of the set of cannabinoid levels.

In some embodiments disclosed herein, the classifier is further configured to classify the sample based on from two or more terpene levels of the set of terpene levels to fifty or more terpene levels of the set of terpene levels.

In some embodiments disclosed herein, the set of terpene levels includes terpene levels for at least the following: terpinolene, alpha phellandrene, beta ocimene, carene, limonene, gamma terpinene, alpha pinene, alpha terpinene, beta pinene, fenchol, camphene, alpha terpineol, alpha humulene, beta caryophyllene, linalool, caryophyllene oxide, and myrcene.

In some embodiments disclosed herein, the set of terpene levels is a set of absolute terpene levels, the classifier configured to generate a set of relative terpene levels based on the set of absolute terpene levels, the classifier further configured to classify the sample based on the set of relative terpene levels.

In some embodiments disclosed herein, the classifier is further configured to: for a first relative terpene level, identify a contribution factor associated therewith, the first relative terpene level being the highest relative terpene level of the set of relative terpene levels; for a second relative terpene level, identify a modulation factor associated therewith, the second relative terpene level being lesser than the first terpene level and greater than a remainder of the set of relative terpene levels, the contribution factor based on a ratio of the second relative terpene level and the first relative terpene level; classify the sample to a first group of the set of groups if the contribution factor is greater than the modulation factor; and classify the sample to a second group of the set of groups if the modulation factor is equal to or greater than the contribution factor.

In some embodiments disclosed herein, wherein the contribution factor is a first contribution factor, the memory configured to store a set of contribution factors including the first contribution factor, the apparatus further comprising an interface for modifying the set of contribution factors.

In some embodiments disclosed herein, the classifier is configured to classify the sample using bottom up hierarchical classification.

In some embodiments disclosed herein, the classifier is configured to classify the sample using an agglomerative hierarchical clustering approach.

In some embodiments disclosed herein, the agglomerative hierarchical clustering approach selected from the group consisting of average linkage clustering, complete linkage clustering, single linkage clustering, and Ward's linkage clustering.

In some embodiments disclosed herein, the agglomerative hierarchical clustering approach generating an output cluster tree, the classifier is configured to prune the output cluster tree at a prespecified level to classify the sample.

A method, comprising: receiving a sample, the sample including a plurality of terpenes and a plurality of cannabinoids; chemically analyzing the sample, including estimating a terpene level of two or more terpenes of the plurality of terpenes in the sample to generate a set of terpene levels; estimating a cannabinoid level of two or more cannabinoids of the plurality of cannabinoids in the sample to generate a set of cannabinoid levels; and based on the set of terpene levels and cannabinoid levels, classifying the sample to a group of a set of groups.

In some embodiments disclosed herein, the chemically analyzing step includes carrying out one or more of high performance liquid chromatography (HPLC) analysis or gas chromatography flame ionization detection (GC-FID) analysis.

In some embodiments of the methods disclosed herein, the sample includes one or more *cannabis* species, each *cannabis* species selected from the group consisting of *Cannabis sativa, Cannabis indica*, and *Cannabis ruderalis*.

In some embodiments of the methods disclosed herein, the sample includes one or more *cannabis* extracts.

In some embodiments of the methods disclosed herein, the classifying step includes classifying the sample based on a highest terpene level of the set of terpene levels.

In some embodiments of the methods disclosed herein, the classifying step includes classifying the sample based on two or more terpene levels of the set of terpene levels, the two or more terpene levels including a first terpene level and a second terpene level, the first terpene level being the highest terpene level of the set of terpene levels, the second terpene level being lesser than the first terpene level and greater than a remainder of the set of terpene levels.

In some embodiments of the methods disclosed herein, the classifying step includes classifying the sample based on three or more terpene levels of the set of terpene levels, the three or more terpene levels including a first terpene level, a second terpene level, and a third terpene level; the first terpene level being the highest terpene level of the set of terpene levels, the second terpene level being lesser than the first terpene level and greater than a remainder of the set of terpene levels, and the third terpene level being lesser than the first and second terpene levels, and greater than a remainder of the set of terpene levels.

In some embodiments of the methods disclosed herein, the classifying step includes classifying the sample based on a highest cannabinoid level of the set of cannabinoid levels.

In some embodiments of the methods disclosed herein, the classifying step includes classifying the sample based on two or more cannabinoid levels of the set of cannabinoid levels, the two or more cannabinoid levels including a first cannabinoid level and a second cannabinoid level, the first cannabinoid level being the highest cannabinoid level of the set of cannabinoid levels, the second cannabinoid level being lesser than the first cannabinoid level and greater than a remainder of the set of cannabinoid levels.

In some embodiments of the methods disclosed herein, the classifying step includes classifying the sample based on from two or more terpene levels of the set of terpene levels to fifty or more terpene levels of the set of terpene levels.

In some embodiments of the methods disclosed herein, the set of terpene levels includes terpene levels for at least the following: terpinolene, alpha phellandrene, beta ocimene, carene, limonene, gamma terpinene, alpha pinene, alpha terpinene, beta pinene, fenchol, camphene, alpha terpineol, alpha humulene, beta caryophyllene, linalool, caryophyllene oxide, and myrcene.

In some embodiments of the methods disclosed herein, the set of terpene levels is a set of absolute terpene levels, the classifying including: generating a set of relative terpene levels based on the set of absolute terpene levels; classifying the sample based on the set of relative terpene levels.

In some embodiments of the methods disclosed herein, the classifying step further includes: for a first relative terpene level of the set of relative terpene levels, identifying a contribution factor associated therewith, the first relative terpene level being the highest relative terpene level of the set of relative terpene levels; for a second relative terpene level of the set of relative terpene levels, identifying a modulation factor associated therewith, the second relative terpene level being lesser than the first terpene level and greater than a remainder of the set of relative terpene levels, the contribution factor based on a ratio of the second relative terpene level and the first relative terpene level; classifying the sample to a first group of the set of groups if the contribution factor is greater than the modulation factor; and classifying the sample to a second group of the set of groups if the modulation factor is equal to or greater than the contribution factor.

In some embodiments of the methods disclosed herein, the classifying including classifying the sample using bottom up hierarchical classification.

In some embodiments of the methods disclosed herein, the classifying step includes classifying the sample using an agglomerative hierarchical clustering approach.

In some embodiments of the methods disclosed herein, the agglomerative hierarchical clustering approach selected from the group consisting of average linkage clustering, complete linkage clustering, single linkage clustering, and Ward's linkage clustering.

In some embodiments of the methods disclosed herein, the agglomerative hierarchical clustering approach generating an output cluster tree, the classifying including pruning the output cluster tree at a prespecified level to classify the sample.

In some embodiments, the present disclosure teaches an apparatus, comprising: a chemical analyzer configured to: receive a sample, the sample including a plurality of cannabinoids; chemically analyze the sample, including estimating a cannabinoid level of two or more cannabinoids of the plurality of cannabinoids in the sample to generate a set of cannabinoid levels; a classifier implemented in a memory or a processing device, the classifier communicably coupled to the chemical analyzer, the classifier configured to, based on the set of cannabinoid levels, classify the sample to a group of a set of groups.

In some embodiments disclosed herein, the classifier is further configured to classify the sample based on two or more cannabinoid levels of the set of cannabinoid levels, the two or more cannabinoid levels including a first cannabinoid level and a second cannabinoid level, the first cannabinoid level being the highest cannabinoid level of the set of cannabinoid levels, the second cannabinoid level being lesser than the first cannabinoid level and greater than a remainder of the set of cannabinoid levels.

In some embodiments disclosed herein, the apparatus further comprises: a sequence generator configured to generate an alphanumeric sequence, the alphanumeric sequence including a first subsequence representing a chemotype associated with the sample based on the cannabinoid levels, the alphanumeric sequence further including a second subsequence representing a cannabinoid associated with the second cannabinoid level; and an output interface configured to transmit the alphanumeric sequence.

In some embodiments disclosed herein, the first subsequence includes one or more numeric characters, and wherein the second subsequence includes one or more alphabetical characters.

In some embodiments disclosed herein, the set of cannabinoid levels is a set of absolute cannabinoid levels, the classifier configured to generate a set of relative cannabinoid levels based on the set of absolute cannabinoid levels, the classifier further configured to classify the sample based on the set of relative cannabinoid levels.

In some embodiments, the present disclosure teaches an apparatus, comprising a chemical analyzer configured to receive a sample, the sample including a plurality of cannabinoids and a plurality of terpenes; chemically analyze the sample, including estimating a cannabinoid level of two or more cannabinoids of the plurality of cannabinoids in the sample to generate a set of cannabinoid levels, further including estimating a terpene level of two or more terpenes of the plurality of terpenes in the sample to generate a set of terpene levels; a classifier implemented in a memory or a processing device, the classifier communicably coupled to the chemical analyzer, the classifier configured to, based on the set of cannabinoid levels and based on the set of terpene levels, classify the sample to a group of a set of groups.

In some embodiments disclosed herein, the classifier further configured to classify the sample based on a first cannabinoid level of the set of cannabinoid levels and based on a first terpene level of the set of terpene levels, the first cannabinoid level being the highest cannabinoid level of the set of cannabinoid levels, the first terpene level being the highest terpene level of the set of terpene levels.

In some embodiments disclosed herein, the apparatus further comprises a sequence generator configured to generate an alphanumeric sequence, the alphanumeric sequence including a first subsequence representing a chemotype associated with the sample based on the cannabinoid levels, the alphanumeric sequence further including a second subsequence representing a terpene associated with the first terpene level; and an output interface configured to transmit the alphanumeric sequence.

In some embodiments disclosed herein, the first subsequence occurs prior to the second subsequence in the alphanumeric sequence.

In some embodiments disclosed herein the second subsequence occurs prior to the first subsequence in the alphanumeric sequence In some embodiments, the present disclosures teaches a kit, comprising: a chemical analyzer configured to: receive a sample, the sample including a plurality of terpenes; and chemically analyze the sample, including estimating a terpene level of two or more terpenes of the plurality of terpenes in the sample to generate a set of terpene levels; and a computing apparatus operatively coupled to the chemical analyzer, the computing apparatus including: a memory configured to receive and store the set of terpene levels, the memory further configured to store a set of predetermined terpene loading factors, the memory further configured to store a set of organoleptic values; and a processor configured to, based on the set of terpene levels and the corresponding terpene loading factors, generate organoleptic values for said sample.

In some embodiments, the present disclosure teaches an apparatus, comprising: a chemical analyzer configured to: receive a sample, the sample including a plurality of terpenes; chemically analyze the sample, including estimating a terpene level of two or more terpenes of the plurality of terpenes in the sample to generate a set of terpene levels; a categorizer implemented in a memory or a processing device, the categorizer communicably coupled to the chemical analyzer, the categorizer configured to, based on the set of terpene levels and a set of predetermined loading factors, generate organoleptic values for the sample.

In some embodiments, the present disclosures teaches a kit, comprising: a chemical analyzer configured to: receive a sample, the sample including a plurality of terpenes and a plurality of cannabinoids; and chemically analyze the sample, including a) estimating a terpene level of two or more terpenes of the plurality of terpenes in the sample to generate a set of terpene levels; b) estimating a cannabinoid level of two or more cannabinoids of the plurality of cannabinoids in the sample to generate a set of cannabinoid levels; and c) a computing apparatus operatively coupled to the chemical analyzer, the computing apparatus including: a memory configured to receive and store the set of terpene levels and cannabinoid levels, the memory further configured to store a set of terpene-cannabinoid combination synergy factors; the memory further configured to store a set entourage effect values; and a processor configured to, based on the set of terpene levels, cannabinoid levels, and terpene-cannabinoid combination synergy factors, generate a set of entourage effect values for the sample.

In some embodiments, the present disclosure teaches an apparatus, comprising: a chemical analyzer configured to: receive a sample, the sample including a plurality of terpenes and a plurality of cannabinoids; chemically analyze the sample, including estimating a terpene level of two or more terpenes of the plurality of terpenes in the sample to generate a set of terpene levels, and estimating a cannabinoid level of two or more cannabinoids of the plurality of cannabinoids in the sample to generate a set of cannabinoid levels; a categorizer implemented in a memory or a processing device, the categorizer communicably coupled to the chemical analyzer, the categorizer configured to, based on the set of terpene level, the set of cannabinoid levels, and terpene-cannabinoid combination synergy factors, generate a set of entourage effect values for the sample.

In some embodiments, the present invention teaches methods of classifying and naming *cannabis* samples based on their cannabinoid and terpene compositions.

In some embodiments, the present invention teaches a method for classifying *cannabis*, said method comprising the steps of: a) determining the absolute cannabinoid contents of a *cannabis* sample; b) determining the relative terpene contents of said sample based on the sample's terpene profile; and c) assigning the *cannabis* sample to a category based on: i. the relative terpene content of the 3 highest accumulating terpenes; and ii. the sample's chemotype, and second highest accumulating cannabinoid; wherein said terpene profile consists of the contents of terpinolene, alpha phellandrene, beta ocimene, careen, limonene, gamma terpinene, alpha pinene, alpha terpinene, beta pinene, fenchol, camphene, alpha terpineol, alpha humulene, beta caryophyllene, linalool, caryophyllene oxide, and myrcene in said *cannabis* sample.

In some embodiments, the present invention teaches that the cannabinoid content is measured by high performance liquid chromatography (HPLC).

In some embodiments, the present inventions teaches that terpene contents are measured by Gas Chromatography (GC).

In some embodiments, the present invention teaches that classification based on the 3 highest accumulating terpenes is performed through the primary ethnobotanical classification method.

In some embodiments, the classification categories of the present invention are represented using a 5 digit code.)

In some embodiments, 2 digits represent the cannabinoid profile of the sample. In some embodiments 3 digits represent the terpene profile of the sample.

In some embodiments, the present invention teaches a method of reporting a *cannabis* sample's organoleptic properties, said method comprising: a. determining the absolute or relative terpene contents of the terpenes in the terpene profile or extended terpene profile of a *cannabis* sample; b. multiplying the absolute or relative content value of each of the terpenes against that terpene's aroma descriptor loading factor, and recording the resulting number; and c. adding each of the values that have been recorded during step b. for each aroma category and recording the final organoleptic values for each aroma; wherein the resulting organoleptic values for each aroma represent the organoleptic contributions from the terpene profile or extended terpene profile.

In some embodiments disclosed herein, the apparatus and kits of the present disclosure comprise an output system for presenting the grouping of the sample on a website, directory, or commercial database.

In some embodiments, the present invention teaches a method of reporting a *cannabis* sample's organoleptic properties, said method comprising: a. determining the absolute or relative terpene contents of the terpenes in the terpene profile or extended terpene profile of a *cannabis* sample; b. multiplying the absolute or relative content value of each of the terpenes against that terpene's flavor descriptor loading factor, and recording the resulting number; and c. adding each of the values that have been recorded during step b for each flavor category and recording the final organoleptic values for each flavor; wherein the resulting organoleptic values for each flavor represent the organoleptic contributions from the terpene profile or extended terpene profile.

DETAILED DESCRIPTION

Definitions

Figure 1:
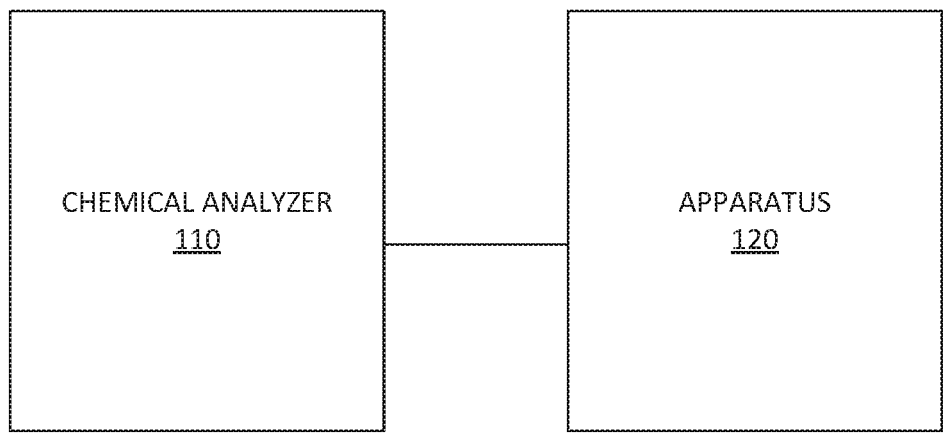
FIG. 1 illustrates a kit/system for classification, according to some embodiments.

As used herein, the verb "comprise" as is used in this description and in the claims and its conjugations are used in its non-limiting sense to mean that items following the word are included, but items not specifically mentioned are not excluded.

The invention provides *cannabis* plants. As used herein, the term "plant" refers to plants in the genus of *Cannabis* and plants derived thereof. Such as *cannabis* plants produced via asexual reproduction and via seed production.

The invention provides plant parts. As used herein, the term "plant part" refers to any part of a plant including but not limited to the embryo, shoot, root, stem, seed, stipule, leaf, petal, flower bud, flower, ovule, bract, trichome, branch, petiole, internode, bark, pubescence, tiller, rhizome, frond, blade, ovule, pollen, stamen, and the like. The two main parts of plants grown in some sort of media, such as soil or vermiculite, are often referred to as the "above-ground" part, also often referred to as the "shoots," and the "below-ground" part, also often referred to as the "roots". Plant part may also include certain extracts such as kief or hash which includes *cannabis* trichomes or glands.

As used herein, the term dominant refers to a terpene that is the most abundant in the terpene profile either in absolute content as a % by dry weight, or in relative content as a % of the terpene profile.

The term "a" or "an" refers to one or more of that entity; for example, "a gene" refers to one or more genes or at least one gene. As such, the terms "a" (or "an"), "one or more" and "at least one" are used interchangeably herein. In addition, reference to "an element" by the indefinite article "a" or "an" does not exclude the possibility that more than one of the elements is present, unless the context clearly requires that there is one and only one of the elements.

The International Code of Zoological Nomenclature defines rank, in the nomenclatural sense, as the level, for nomenclatural purposes, of a taxon in a taxonomic hierarchy (e.g., all families are for nomenclatural purposes at the same rank, which lies between superfamily and subfamily). While somewhat arbitrary, there are seven main ranks defined by the international nomenclature codes: kingdom, phylum/division, class, order, family, genus, and species.

The invention provides plant varieties. As used herein, the term "variety" means a group of similar plants that by genetic lineage is distinguished from other cultivars within the same species. Furthermore, the term "cultivar" variously refers to a variety, strain or race of plant that has been produced by horticultural or agronomic techniques and is not normally found in wild populations. The terms cultivar, variety, strain and race are often used interchangeably by plant breeders, agronomists and farmers.

The term "variety" as used herein has identical meaning to the corresponding definition in the International Convention for the Protection of New Varieties of Plants (UPOV treaty), of Dec. 2, 1961, as Revised at Geneva on Nov. 10, 1972, on Oct. 23, 1978, and on Mar. 19, 1991. Thus, "variety" means a plant grouping within a single botanical taxon of the lowest known rank, which grouping, irrespective of whether the conditions for the grant of a breeder's right are fully met, can be i) defined by the expression of the characteristics resulting from a given genotype or combination of genotypes, ii) distinguished from any other plant grouping by the expression of at least one of the said characteristics and iii) considered as a unit with regard to its suitability for being propagated unchanged.

As used herein, the term "inbreeding" refers to the production of offspring via the mating between relatives. The plants resulting from the inbreeding process are referred to herein as "inbred plants" or "inbreds."

The term LOQ as used herein refers to the limit of quantitation for Gas Chromatography (GC) and High Performance Liquid Chromatography measurements.

The term "secondary metabolites" as used herein refers to organic compounds that are not directly involved in the normal growth, development, or reproduction of an organism. In other words, loss of secondary metabolites does not result in immediate death of said organism.

The invention provides samples. As used herein, the term "sample" includes a sample from a plant, a plant part, a plant cell, or from a transmission vector, or a soil, water or air sample.

The invention provides offspring. As used herein, the term "offspring" refers to any plant resulting as progeny from a vegetative or sexual reproduction from one or more parent plants or descendants thereof. For instance an offspring plant may be obtained by cloning or selfing of a parent plant or by crossing two parent plants and include selfings as well as the F1 or F2 or still further generations. An F1 is a first-generation offspring produced from parents at least one of which is used for the first time as donor of a trait, while offspring of second generation (F2) or subsequent generations (F3, F4, etc.) are specimens produced from selfings of F1's, F2's etc. An F1 may thus be (and usually is) a hybrid resulting from a cross between two true breeding parents (true-breeding is homozygous for a trait), while an F2 may be (and usually is) an offspring resulting from self-pollination of said F1 hybrids.

The invention provides methods for crossing a first plant with a second plant. As used herein, the term "cross", "crossing", "cross pollination" or "cross-breeding" refer to the process by which the pollen of one flower on one plant is applied (artificially or naturally) to the ovule (stigma) of a flower on another plant. Backcrossing is a process in which a breeder repeatedly crosses hybrid progeny, for example a first generation hybrid (F1), back to one of the parents of the hybrid progeny. Backcrossing can be used to introduce one or more single locus conversions from one genetic background into another.

In some embodiments, the present invention provides methods for obtaining plant genotypes comprising recombinant genes. As used herein, the term "genotype" refers to the genetic makeup of an individual cell, cell culture, tissue, organism (e.g., a plant), or group of organisms.

The invention provides for *cannabis* samples. As used herein, a "*cannabis* sample" refers to any *cannabis* plant tissue, or an extract thereof.

The invention provides plant tissue. As used herein, the term "plant tissue" refers to any part of a plant. Examples of plant organs include, but are not limited to the leaf, stem, root, tuber, seed, branch, pubescence, nodule, leaf axil, flower, pollen, stamen, pistil, petal, peduncle, stalk, stigma, style, bract, fruit, trunk, carpel, sepal, anther, ovule, pedicel, needle, cone, rhizome, stolon, shoot, pericarp, endosperm, placenta, berry, stamen, and leaf sheath.

In some embodiments, the present invention provides plant varieties comprising the recombinant genes. As used herein, the term "variety" refers to a subdivision of a species, consisting of a group of individuals within the species that are distinct in form or function from other similar arrays of individuals.

In some embodiments, the methods of the present invention detect the levels of myrcene in a variety. In other embodiments, the present invention quantifies "couch lock" and relaxation effects of myrcene. As used herein, the term couch lock is defined as a heavy body high which reduces the ability of users to function, and is associated with lethargy and lack of motivation.

As used herein, a *cannabis* plant's terpene profile is defined in absolute or relative contents of 17 key terpenes including: terpinolene, alpha phellandrene, beta ocimene, carene, limonene, gamma terpinene, alpha pinene, alpha terpinene, beta pinene, fenchol, camphene, alpha terpineol, alpha humulene, beta caryophyllene, linalool, caryophyllene oxide, and myrcene.

As used herein the term "module" refers to any assembly and/or set of operatively-coupled electrical components that can include, for example, a memory, a processor, electrical traces, optical connectors, software (executing in hardware), and/or the like. For example, a module executed in the processor can be any combination of hardware-based module (e.g., a field-programmable gate array (FPGA), an application specific integrated circuit (ASIC), a digital signal processor (DSP)) and/or software-based module (e.g., a module of computer code stored in memory and/or executed at the processor) capable of performing one or more specific functions associated with that module.

FIG. 1 illustrates a system/kit 100 for chemical analysis and classification, according to embodiments. The system 100 includes a chemical analyzer 110 and an apparatus 120. In some embodiments, the chemical analyzer 110 includes a high performance liquid chromatography (HPLC) analyzer. In some embodiments, the chemical analyzer 110 includes a Gas Chromatography Flame Ionization Detection (GC-FID) analyzer. In some embodiments, the chemical analyzer 110 includes at least a memory and a processing device.

The chemical analyzer 110 can be communicatively coupled to the apparatus 120 using any suitable wired (e.g., data cables), wireless Bluetooth, NFC, and/or the like), and/or networked (e.g., the Internet, or a local area network) means. In some embodiments (not shown), one or more components, devices, and/or systems can be present in the connection between the chemical analyzer 110 and the apparatus 120, such as, for example, a database that receives chemical analysis data generated by the chemical analyzer 110, and accessible by the apparatus 120. In some embodiments, the chemical analyzer 110 and the apparatus 120 are formed within the same housing.

Figure 2:
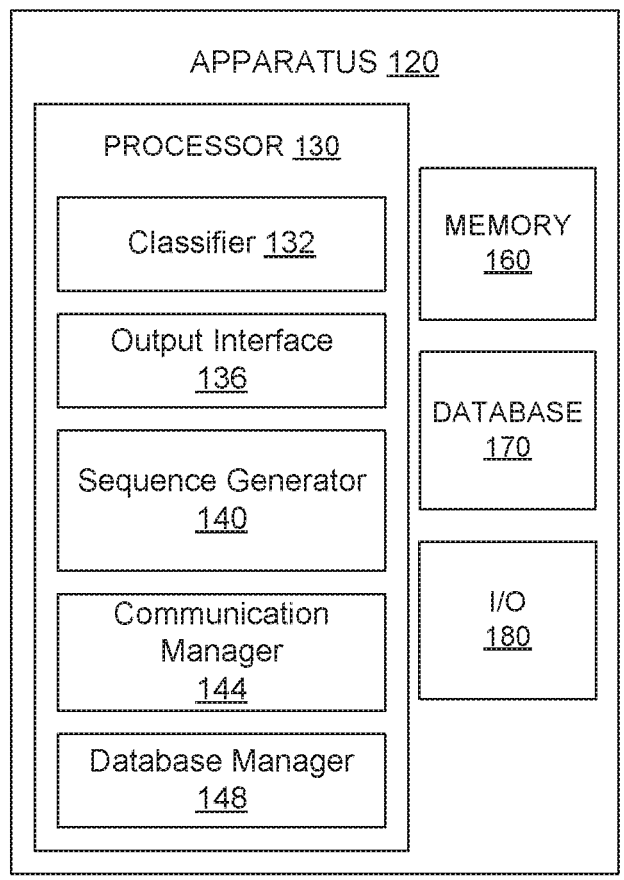
FIG. 2 illustrates an apparatus for classification, according to some embodiments.

As best illustrated in FIG. 2, in some embodiments, the apparatus 120 includes at least a processor 130 and a memory 160, and further includes a database 170, although it is understood that, in some embodiments, the memory 160 and the database 170 can be the same component. In some embodiments, the database constitutes one or more databases. Further, in other embodiments (not shown), at least one database can be external to the apparatus 120 and/or the system 100. The apparatus 120 can be a personal computer, a server, a workstation, a tablet, a mobile device, a cloud computing environment (e.g., including one or more servers, processors, etc.), an application or a module running on any of these platforms, and/or the like.

The memory 160 and/or the database 170 of the apparatus 120 can independently be, for example, a random access memory (RAM), a memory buffer, a hard drive, a database, an erasable programmable read-only memory (EPROM), an electrically erasable read-only memory (EEPROM), a read-only memory (ROM), Flash memory, and/or so forth. The memory 160 and/or the database 170 can store instructions to cause the processor 130 to execute modules, processes and/or functions associated with the apparatus 120.

In some embodiments, the apparatus 120 can be communicably coupled to a network, which can be any type of network such as, for example, a local area network (LAN), a wide area network (WAN), a virtual network, a telecommunications network, a data network, and/or the Internet, implemented as a wired network and/or a wireless network. In some embodiments, any or all communications can be secured using any suitable type and/or method of secure communication (e.g., secure sockets layer (SSL)) and/or encryption. In other embodiments, any or all communications can be unsecured.

Still referring to the apparatus 120, the processor 130 can be, for example, a general purpose processor, a Field Programmable Gate Array (FPGA), an Application Specific Integrated Circuit (ASIC), a Digital Signal Processor (DSP), and/or the like. The processor 130 can be configured to run and/or execute application processes and/or other modules, processes and/or functions associated with the apparatus 120, with the system 100, and/or the network. As illustrated in FIG. 2, the processor 130 can include a classifier 132, an output interface 136, and a sequence generator 140. In some embodiments, the processor 130 can include a communication manager 144 (i.e., a communication component/module) configured to facilitate network connectivity for the host device 106 and/or system 100. For example, the communication manager 144 can include and/or enable a network interface controller (NIC), wireless connection, a wired port, and/or the like. As such, the communication manager 144 can establish and/or maintain a communication session with the chemical analyzer 110. In some embodiments, the processor 130 includes a database manager 148 (i.e., a database component/module) configured to interface with the memory 160 and/or the database 170 for data manipulation (including storage, modification, and/or deletion). In some embodiments, the processor 130 can include additional components/modules (not shown).

Each component and/or module 132, 136, 140, 144, 148 can independently be a hardware component/module and/or a software component/module (implemented in hardware, such as the processor). In some embodiments, each of the components/modules can be operatively coupled to each other. In other embodiments, the functionality of one or more of the components/modules can be combined and/or overlap. In some embodiments, the functionality of one or more components/modules and/or the interaction between the components/modules can be based on regulatory requirements for data processing, storage, integrity, security, and/or the like. While shown as being implemented in the processor, in other embodiments, the components/modules, or a portion thereof, can be distributed, and implemented in other processors and/or network devices. Such processors and/or network devices can be communicatively coupled via, for example, a network.

Referring to FIGS. 1-2, in some embodiments, a kit 100 includes the chemical analyzer 110 and the apparatus 120. In some embodiments, the apparatus 120 includes the chemical analyzer 110. In some embodiments, the chemical analyzer 110 is configured to receive a sample for chemical analysis. In some embodiments, the sample is a *cannabis* sample that includes multiple terpenes. In some embodiments, the *cannabis* sample includes one or more *cannabis* species selected from the group consisting of *Cannabis sativa, Cannabis indica*, and *Cannabis ruderalis*.

In some embodiments, the chemical analyzer 110 is further configured to chemically analyze the sample to estimates a terpene level of two or more terpenes. In this manner, the chemical analyzer 110 can generate a set of terpene levels based on the estimated terpene levels. In some embodiments, the chemical analyzer includes one or more of a high performance liquid chromatography (HPLC) analyzer or gas chromatography flame ionization detection (GC-FID) analyzer.

In some embodiments, the memory 160 of the apparatus 120 is configured to receive the set of terpene levels from the chemical analyzer 110, and to store the set of terpene levels in the memory 130 and/or the database 170 (e.g., via the database manager 140. In some embodiments, the memory 130 stores a set of groups for purposes of classification.

In some embodiments, the classifier 132 is configured to, based on the set of terpene levels, classify the sample to a selected group of the set of groups. In some embodiments, the classifier 132 is further configured to classify the sample based on a highest terpene level of the set of terpene levels. In some embodiments, the classifier 132 is further configured to classify the sample based on 2 or more terpene levels, including a first terpene level and a second terpene level. The first terpene level is the highest/greatest terpene level of the set of terpene levels, and the second terpene level being lesser than the first terpene level and greater than the remaining terpene levels of the set of terpene levels, i.e., the second terpene level is the second-highest terpene level. In some embodiments, the classifier 132 is further configured to classify the sample based on 3 or more terpene levels, including a first terpene level, a second terpene level (second highest terpene level), and a third terpene level (third highest terpene level). In some embodiments, the processor 130 is further configured to classify the sample based on 4 or more highest terpene levels, 10 or more, 15 or more, 20 or more, 25 or more, 30 or more, 35 or more, 40 or more, 45 or more, 50 or more, 55 or more, 60 or more highest terpene levels, including all values and subranges in between. In some embodiments, the set of terpene levels includes terpene levels for one or more of the following: terpinolene, alpha phellandrene, beta ocimene, carene, limonene, gamma terpinene, alpha pinene, alpha terpinene, beta pinene, fenchol, camphene, alpha terpineol, alpha humulene, beta caryophyllene, linalool, caryophyllene oxide, and myrcene.

In some embodiments, the set of terpene levels generated by the chemical analyzer 110 is a set of absolute terpene levels, measurable in terms of w/w %. In some embodiments, the classifier 132 is configured to generate a set of relative terpene levels based on the set of absolute terpene levels, and to classify the sample based on the set of relative terpene levels. For example, the relative terpene levels can be measurable in terms of the percentage ratio of terpene level for a particular terpene to the total terpene level for all detectable terpenes.

In some embodiments, a set of contribution factors, each contribution factor corresponding to a different terpene, is specified and stored in the memory 160 and/or the database 170. In some embodiments, the classifier 132 is configured to for a first (highest) relative terpene level, identify the contribution factor associated therewith. The classifier 132 is further configured to for a second (second-highest) relative terpene level, identify/calculate a modulation factor. In some embodiments, the modulation factor is based on a ratio of the second relative terpene level and the first relative terpene level. The classifier 132 is further configured to classify the sample to a first group of the set of groups if the contribution factor is greater than the modulation factor, and to classify the sample to a second, different group of the set of groups if the modulation factor is equal to or greater than the contribution factor. In some embodiments, the contribution factor is about 50%. In some embodiments, the apparatus 120 includes an interface (e.g., via the I/O interface 180) that permits a user of the apparatus and/or another computing entity to modify the set of contribution factors stored in the memory 160 and/or the database 170.

The classifier 132 can be configured to classify the sample based on any suitable deterministic and/or probabilistic classification approach. In some embodiments, the classifier 132 is classify the sample using bottom up hierarchical classification based on the set of absolute and/or relative terpene levels. In some embodiments, the bottom up hierarchical classification approach includes an agglomerative hierarchical clustering approach implemented in any suitable manner. In some embodiments, the agglomerative hierarchical clustering approach is selected from the group consisting of average linkage clustering, complete linkage clustering, single linkage clustering, and Ward's linkage clustering. In some embodiments, the agglomerative hierarchical clustering approach results in a cluster tree, and the classifier 132 is configured to prune the output cluster tree at a prespecified level to classify the sample to a group.

The sequence generator 140 can be configured to receive an indication of the selected group of the set of groups, and further configured to generate an alphanumeric sequence based on at least one of the set of terpene levels and the selected group. The sequence generator 140 can be further configured to transmit the alphanumeric sequence to the output interface 136, such as for transmission to a user interface, to another device, and/or the like.

Still referring to FIGS. 1-2, in some embodiments, the chemical analyzer 110 is configured to receive a sample that includes multiple cannabinoids. In some embodiments, the sample includes one or more *cannabis* species, each *cannabis* species selected from the group consisting of *Cannabis sativa, Cannabis indica*, and *Cannabis ruderalis*.

In some embodiments, the chemical analyzer 110 is configured to chemically analyze the sample and estimate a cannabinoid level of two or more cannabinoids in the sample to generate a set of cannabinoid levels. In some embodiments, the chemical analyzer includes one or more of a high performance liquid chromatography (HPLC) analyzer or gas chromatography flame ionization detection (GC-FID) analyzer.

In some embodiments, the classifier 132 is configured to based on the set of cannabinoid levels, classify the sample to a group of a set of groups. In some embodiments, the classifier 132 is configured to classify the sample based on a highest cannabinoid level of the set of cannabinoid levels. In some embodiments, the classifier 132 is further configured to classify the sample based on two or more highest cannabinoid levels of the set of cannabinoid levels. Said another way, the two or more cannabinoid levels include a first cannabinoid level and a second cannabinoid level, where the first cannabinoid level is the highest cannabinoid level of the set of cannabinoid levels, and the second cannabinoid level is lesser than the first cannabinoid level but greater than a remainder of the set of cannabinoid levels.

In some embodiments, the set of cannabinoid levels is a set of absolute cannabinoid levels, and the classifier 132 is configured to generate a set of relative cannabinoid levels based on the set of absolute cannabinoid levels. In some embodiments, the classifier 132 is further configured to classify the sample based on the set of relative cannabinoid levels.

The sequence generator 140 is configured to generate an alphanumeric sequence based on the set of cannabinoid levels and/or the selected group. The alphanumeric sequence includes a first subsequence representing a cannabinoid associated with the first cannabinoid level, and a second subsequence representing a cannabinoid associated with the second cannabinoid level. In some embodiments, the first subsequence includes one or more numeric characters (e.g., numbers from 0-9, from 0-99, from 0-999, and/or the like), and wherein the second subsequence includes one or more alphabetical characters (e.g., letters from A-Z, AA-ZZ, and/or the like).

The output interface 136 is configured to receive the alphanumeric sequence (or an indication thereof), and to transmit an indication and/or representation of the alphanumeric sequence, such as to a user interface, a device (e.g., a printer), and/or the like.

Still referring to FIGS. 1-2, in some embodiments, the chemical analyzer 110 is configured to receive a sample that includes multiple cannabinoids and multiple terpenes. In some embodiments, the sample includes one or more *cannabis* species, each *cannabis* species selected from the group consisting of *Cannabis sativa, Cannabis indica*, and *Cannabis ruderalis*.

In some embodiments, the chemical analyzer 110 is configured to chemically analyze the sample to estimate a cannabinoid level of two or more cannabinoids to generate a set of cannabinoid levels, and to estimating a terpene level of two or more terpenes in the sample to generate a set of terpene levels. In some embodiments, the chemical analyzer 110 includes one or more of a high performance liquid chromatography (HPLC) analyzer or gas chromatography flame ionization detection (GC-FID) analyzer.

In some embodiments, the classifier 132 is configured to, based on the set of cannabinoid levels and based on the set of terpene levels, classify the sample to a group of a set of groups. In some embodiments, the classifier 132 is further configured to classify the sample based on a first (highest) cannabinoid level of the set of cannabinoid levels and based on a first (highest) terpene level of the set of terpene levels.

The sequence generator 140 is configured to generate an alphanumeric sequence based on one or more of the set of cannabinoid levels, the set of terpene levels, and the selected group. In some embodiments, the alphanumeric sequence includes a first subsequence representing a cannabinoid associated with the first cannabinoid level, and a second subsequence representing a terpene associated with the first terpene level. In some embodiments, the first subsequence occurs prior to the second subsequence in the alphanumeric sequence, and in other embodiments, the second subsequence occurs prior to the first subsequence in the alphanumeric sequence.

The output interface 136 is configured to receive the alphanumeric sequence (or an indication thereof), and to transmit an indication and/or representation of the alphanumeric sequence, such as to a user interface, a device (e.g., a printer), and/or the like.

Figure 3:
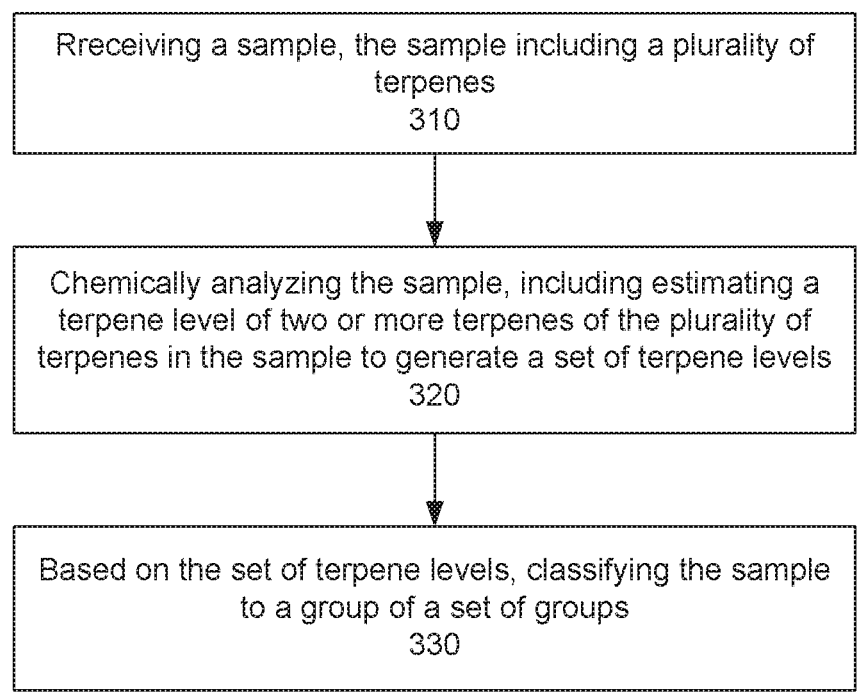
FIG. 3 illustrates a method for classification, according to some embodiments.)

Referring to FIG. 3, a method 300 of classification is illustrated that can be carried out by aspects of the system 100, and/or a structural/functional variant thereof. The method includes, at 310, receiving a sample that includes multiple terpenes (e.g., at the chemical analyzer 110). In some embodiments, the sample includes one or more *cannabis* species selected from the group consisting of *Cannabis sativa, Cannabis indica*, and *Cannabis ruderalis*.

The method also includes, at step 320, chemically analyzing (e.g., using the chemical analyzer 110) the sample to estimate a terpene level of two or more terpenes in the sample to generate a set of terpene levels. In some embodiments, chemical analysis includes one or more of high performance liquid chromatography (HPLC) analysis or gas chromatography flame ionization detection (GC-FID) analysis. In some embodiments, the set of terpene levels includes terpene levels for at least the following: terpinolene, alpha phellandrene, beta ocimene, carene, limonene, gamma terpinene, alpha pinene, alpha terpinene, beta pinene, fenchol, camphene, alpha terpineol, alpha humulene, beta caryophyllene, linalool, caryophyllene oxide, and myrcene.

In some embodiments, step 320 comprises chemically analyzing the sample to estimate a cannabinoid level for two or more cannabinoids in the sample to generate a set of cannabinoid levels.

The method also includes, at step 330, based on the set of terpene levels, classifying (e.g., via the classifier 132) the sample to a group of a set of groups. In some embodiments, the classifying including classifying the sample based on a highest terpene level. In some embodiments, the classifying including classifying the sample based on two or more highest terpene levels of the set of terpene levels. In some embodiments, the classifying including classifying the sample based on from two or more highest terpene levels to fifty or more highest terpene levels, including all values and subranges in between.

In some embodiments, the set of terpene levels is a set of absolute terpene levels, and the classifying at step 330 includes generating a set of relative terpene levels based on the set of absolute terpene levels, and classifying the sample based on the set of relative terpene levels.

In some embodiments, classifying step 330 includes classifying the sample to a group of a set of groups based on the cannabinoid levels.

In some embodiments, classifying step 330 includes classifying the sample to a group of a set of groups based on the cannabinoid levels and the terpene levels.

In some embodiments, the classifying at step 330 further includes, for a first relative (highest) terpene level, identifying a contribution factor associated therewith. In some embodiments, the classifying at step 330 further includes, for a second (second highest) relative terpene level, identifying/calculating a modulation factor associated therewith. The modulation factor is based on a ratio of the second relative terpene level and the first relative terpene level. In some embodiments, the classifying at step 330 further includes classifying the sample to a first group if the contribution factor is greater than the modulation factor, and to a second, different group if the modulation factor is equal to or greater than the contribution factor.

In some embodiments, the classifying at step 330 includes using a bottom up hierarchical classification. In some embodiments, the bottom up hierarchical classification employs a agglomerative hierarchical clustering approach. In some embodiments, the agglomerative hierarchical clustering approach is selected from the group consisting of average linkage clustering, complete linkage clustering, single linkage clustering, and Ward's linkage clustering. In some embodiments, the agglomerative hierarchical clustering approach generates an output cluster tree, and the classifying at step 330 includes pruning the output cluster tree at a prespecified level to classify the sample.

Cannabis Plants

*Cannabis* is an annual, dioecious, flowering herb. The leaves are palmately compound or digitate, with serrate leaflets. *Cannabis* normally has imperfect flowers, with staminate "male" and pistillate "female" flowers occurring on separate plants. It is not unusual, however, for individual plants to separately bear both male and female flowers (i.e., have monoecious plants). Although monoecious plants are often referred to as "hermaphrodites," true hermaphrodites (which are less common in *cannabis*) bear staminate and pistillate structures on individual flowers, whereas monoecious plants bear male and female flowers at different locations on the same plant.

The life cycle of *cannabis* varies with each variety but can be generally summarized into germination, vegetative growth, and reproductive stages. Because of heavy breeding and selection by humans, most *cannabis* seeds have lost dormancy mechanisms and do not require any pre-treatments or winterization to induce germination (See Clarke, R C et al. "*Cannabis*: Evolution and Ethnobotany" University of California Press 2013). Seeds placed in viable growth conditions are expected to germinate in about 3 to 7 days. The first true leaves of a *cannabis* plant contain a single leaflet, with subsequent leaves developing in opposite formation. In some embodiments, subsequent leaves develop with increasing number of leaflets. Leaflets can be narrow or broad depending on the morphology of the plant grown. *Cannabis* plants are normally allowed to grow vegetatively for the first 4 to 8 weeks. During this period, the plant responds to increasing light with faster and faster growth. Under ideal conditions, *cannabis* plants can grow up to 2.5 inches a day, and are capable of reaching heights of up to 20 feet. Indoor growth pruning techniques tend to limit *cannabis* size through careful pruning of apical or side shoots.

*Cannabis* is diploid, having a chromosome complement of 2n=20, although polyploid individuals have been artificially produced. The first genome sequence of *Cannabis*, which is estimated to be 820 Mb in size, was published in 2011 by a team of Canadian scientists (Bakel et al, "The draft genome and transcriptome of *Cannabis sativa*" Genome Biology 12:R102).

The genus *Cannabis* was formerly placed in the Nettle (Urticaceae) or Mulberry (Moraceae) family, and later, along with the *Humulus* genus (hops), in a separate family, the Hemp family (Cannabaceae sensu stricto). Recent phylogenetic studies based on cpDNA restriction site analysis and gene sequencing strongly suggest that the Cannabaceae sensu stricto arose from within the former Celtidaceae family, and that the two families should be merged to form a single monophyletic family, the Cannabaceae sensu lato.

Although, some *cannabis* varieties will flower without the need for external stimuli, most varieties have an absolute requirement for inductive photoperiods in the form of short days or long nights to induce fertile flowering. The first sign of flowering in *cannabis* is the appearance of undifferentiated flower primordial along the main stem of the nodes. At this stage, the sex of the plants is still not distinguishable. As the flower primordia continue to develop, female (pistillate), and male (staminate) flowers can be distinguished. The fruit of *cannabis* plants is known as the achene.

For most cannabinoid producing purposes, only female plants are desired. The presence of male flowers is considered undesirable as pollination is known to reduce the cannabinoid yield, and potentially ruin a crop. For this reason, most *cannabis* is grown "sinsemilla" through vegetative (i.e., asexual) propagation. In this way, only female plants are produced and no space is wasted on male plants.

Traditional *Cannabis* Classification Schemes

Although scientists have continually studied the phylogeny and morphology of the *cannabis* plant, its modern resurgence as a recreational and medical drug has led to a return of *cannabis* culture, and with it, a rise in the general population's interest in *cannabis* genetics, production, and use. Eager for ways to distinguish between strains with different colors, shapes, and "highs," the *cannabis* community turned to traditional methods of classifying plants based on morphological properties. A few of the more popular classification schemes are described below.

Classification of *Cannabis* into Species

*Cannabis* is a genus of flowering plants which have historically categorized into at least three species known as *Cannabis sativa, Cannabis indica,* and *Cannabis ruderalis.* The first recorded distinction between *Cannabis sativa* and *Cannabis indica* was made by Jean-Baptiste Lamarck in 1785, when Lamark noted that 'sativas' exhibited a taller, more fibrous morphology compared to the 'indicas,' which exhibited shorter, more bush-like structures. The third species known as *Cannabis ruderalis* was discovered in 1924 when Russian botanist D. E. Janischevsky identified a small and uncultivated weedy variety of *Cannabis* dispersed throughout Eurasian countries. This smaller 'wild' species, which produced trichome-like glands at the base of each seed to attract beetles, was hypothesized to be the ancestor of the better known psychotropic *C. sativa* and *C. indica* species which we know today.

Throughout the early 1900's much of the available *cannabis* in the United States was *C. saliva.* However, in the 1970's *C. indica* plants, whose cultivation had previously been concentrated in contiguous parts of Afghanistan, Pakistan, and Kashmir (see misnomer of *Cannabis afghanica*), was introduced into the North American and Western European markets. The *indica* plant's high THC production (resinous flowers), coupled with their small stature, made them ideal for indoor, or clandestine-outdoor cultivations, where they could be surreptitiously grown among different kinds of shrub-like vegetation.

As interest in the plant blossomed, amateur breeders began crossing the archetypal '*sativa*' and '*indica*' varieties to create new hybrids with desired psychotropic or morphological phenotypes (i.e. flower trichome production, morphology, color, etc). In its early stages, these breeding efforts resulted in varieties that could still be recognized as "mostly indicas" or "mostly sativas." With time however, repeated breeding cycles and accidental cross-hybridizations led to the blurring of the line between the two species. Today's cultivated varieties are classified into an increasingly subdivided spectrum of "*sativa*," "mostly *sativa,*" "*sativa*-like indicas," "*indica*-like sativas," etc.

Because these species classifications are largely based on a plant's outward appearance without serious consideration for each plant's chemical makeup, the medical and recreational effects of branded *indica* or *sativa* products rarely correlate with their name. Thus doctors and consumers are no longer able to rely on the historical properties associated with each species as an indicator for today's modern cultivated *cannabis* products.

Classification of *Cannabis* into "Varieties"

Another popular classification scheme was the identification of new *cannabis* products by strain names. These names were often associated with a specific morphological property of the plant. New hybrids with particularly distinct or desirable properties such as "Purple Haze" or "Panama Red," became popular due to their respective purple and red colors, and the effects associated with the strain.

The use of variety names to distinguish between different *cannabis* types remains the most popular method of distinguishing products to date. Today, most *cannabis* in the United States is sold based on variety names. Popular varieties include for example, the 1995 high times *cannabis* cup winner "White Widow," or the 2010 high times *cannabis* cup winner "Amnesia Lemon."

Despite its popularity, this new trend in *cannabis* classification presents several issues for consumers. First, the naming of a new variety is entirely arbitrary and does not convey any information related to the effects a consumer is expected to experience. Second, popular strains are often high jacked or reused to indicate parental lineages for new plants that often share little to no similarity to the original product, further confusing any association of the name with an effect (e.g. "OG Wreck," "OG Legend," and "Classic OG").

Moreover, because there is no standard practice of comparing varieties bearing a strain name to its original namesake, plants having the same name can have wildly different properties. For example, a grower obtaining a seed of the popular "White Rhino" variety is likely to produce the new product under the same name regardless of whether the seed was segregating for several critical genes (thus producing a different effect), or was incorrectly or fraudulently labeled at the time it was acquired. It is also known that *cannabis* products can vary in chemical composition depending on the growth conditions in which they were produced. Thus without standard growth conditions, even plants which are genetically identical can end up producing different effects in consumers.

The end result is that while variety naming provides a popular way to brand new products, it bears little correlation to the medical or recreational effect that the plant will have on the consumer.

Classification of *Cannabis* into Chemotypes

Chemotype classifications were one of the first attempts at classifying *cannabis* samples based on their chemical compositions rather than their morphological properties. Research into the genes responsible for the production of each cannabinoid led to the classification of *cannabis* into "chemotype" groups based on the presence of key biosynthetic isozymes. See de Meijer et al. I, II, III, and IV (I: 2003, *Genetics,* 163:335-346; II: 2005, *Euphytica,* 145:189-198; III: 2009, *Euphytica,* 165:293-311; and IV: 2009, *Euphytica,* 168:95-112.

These chemotype classifications used among researchers provide information regarding the genetic background of a *cannabis* plant, while also providing a rough idea of the cannabinoid content that is expected in the plant. For example *cannabis* plants with $B_T/B_T$ genotypes, and THC as the main cannabinoid constituent are classified into the chemotype I group. *Cannabis* plants with $B_T/B_D$ genotypes and accumulation of both THC and CBD are classified into the chemotype II group. Chemotype III plants contain $B_D/B_D$ genotypes and accumulate CBD as the main cannabinoid constituent. Chemotype N plants contain Bo/Bo genotypes and accumulate CBG, with residual amounts of CBD. Chemotype V plants contain o/o genotypes and do not accumulate detectable levels of cannabinoids.

While the chemotype categorization of *cannabis* plants presented a step in the right direction, it still suffered from many drawbacks. As an initial matter, the classification scheme only accounted for a few of the cannabinoids, ignoring the short hand classification of plants containing CBC, or propyl cannabinoids. In addition, because the chemotype classifications were largely based on genetic studies, rather than chemical profile analyses, they often fail to provide information regarding the relative accumulation of cannabinoids. For example, a chemotype II label on a plant indicates the presence of both THC and CBD, but does not provide information as to which of the cannabinoids is most prevalent (e.g. a 1:2 or 2:1 THC to CBD ratio).

The chemotype classification's focus on genotype can also lead to situation in which no information is provided regarding the secondary cannabinoids (e.g. the accumulation of CBG in chemotype I, II, or II plants). Finally the chemotype characterization only provided information regarding the cannabinoid accumulation of the plant, without also considering the important effects of terpenes in producing an organoleptic experience, and modulating the recreational and medical effects of the *cannabis* via entourage interactions.

Thus there was a need for the development of new *cannabis* classification methods based on the chemical profiles of *cannabis* which are responsible for the organoleptic and physiological effects experienced by consumers.

Cannabinoids and Terpenes—The Chemistry of *Cannabis* Cannabinoids

*Cannabis* plants produce a unique family of terpenophenolic compounds called cannabinoids. Cannabinoids, terpenoids, and other compounds are secreted by glandular trichomes that occur most abundantly on the floral calyxes and bracts of female plants. As a drug it usually comes in the form of dried flower buds (marijuana), resin (hashish), or various extracts collectively known as hashish oil. There are at least 483 identifiable chemical constituents known to exist in the *cannabis* plant (Rudolf Brenneisen, 2007, Chemistry and Analysis of Phytocannabinoids (cannabinoids produced by *cannabis*) and other *Cannabis* Constituents, In Marijuana and the Cannabinoids, ElSohly, ed.; incorporated herein by reference) and at least 85 different cannabinoids have been isolated from the plant (El-Alfy, Abir T, et al., 2010, "Antidepressant-like effect of delta-9-tetrahydrocannabinol and other cannabinoids isolated from *Cannabis sativa* L", Pharmacology Biochemistry and Behavior 95 (4): 434-42; incorporated herein by reference). The two cannabinoids usually produced in greatest abundance are cannabidiol (CBD) and/or $\Delta^9$-tetrahydrocannabinol (THC). THC is psychoactive while CBD is not. See, ElSohly, ed. (Marijuana and the Cannabinoids, Humana Press Inc., 321 papers, 2007), which is incorporated herein by reference in its entirety, for a detailed description and literature review on the cannabinoids found in marijuana.

Cannabinoids are the most studied group of secondary metabolites in *cannabis*. Most exist in two forms, as acids and in neutral (decarboxylated) forms. The acid form is designated by an "A" at the end of its acronym (i.e. THCA). The phytocannabinoids are synthesized in the plant as acid forms, and while some decarboxylation does occur in the plant, it increases significantly post-harvest and the kinetics increase at high temperatures. (Sanchez and Verpoorte 2008, "Secondary metabolism in *cannabis*", Phytochemistry Review 7:615-639). The biologically active forms for human consumption are the neutral forms. Decarboxylation is usually achieved by thorough drying of the plant material followed by heating it, often by either combustion, vaporization, or heating or baking in an oven. Unless otherwise noted, references to cannabinoids in a plant include both the acidic and decarboxylated versions (e.g., CBD and CBDA).

The cannabinoids in *cannabis* plants include, but are not limited to, $\Delta^9$-Tetrahydrocannabinol ($\Delta^9$-THC), $\Delta^8$-Tetrahydrocannabinol ($\Delta^8$-THC), Cannabichromene (CBC), Cannabicyclol (CBL), Cannabidiol (CBD), Cannabielsoin (CBE), Cannabigerol (CBG), Cannabinidiol (CBND), Cannabinol (CBN), Cannabitriol (CBT), and their propyl homologs, including, but are not limited to cannabidivarin (CBDV), $\Delta^9$-Tetrahydrocannabivarin (THCV), cannabichromevarin (CBCV), and cannabigerovarin (CBGV). See Holley et al. ("Constituents of *Cannabis sativa* L. XI Cannabidiol and cannabichromene in samples of known geographical origin", *J. Pharm. Sci.* 64:892-894, 1975) and De Zeeuw et al. ("Cannabinoids with a propyl side chain in *Cannabis*, Occurrence and chromatographic behavior", Science 175:778-779), each of which is herein incorporated by reference in its entirety for all purposes. Non-THC cannabinoids can be collectively referred to as "CBs", wherein CBs can be one of THCV, CBDV, CBGV, CBCV, CBD, CBC, CBE, CBG, CBN, CBND, and CBT cannabinoids.

Cannabinoids are a class of diverse chemical compounds that activate cannabinoid receptors. Cannabinoids produced by plants are called phytocannabinoids, a.k.a., natural cannabinoids, herbal cannabinoids, and classical cannabinoids. At least 85 different cannabinoids have been isolated from the *cannabis* plants (El-Alfy et al., 2010, "Antidepressant-like effect of delta-9-tetrahydrocannabinol and other cannabinoids isolated from *Cannabis sativa* L", Pharmacology Biochemistry and Behavior 95 (4): 434-42; Brenneisen, supra). Typical cannabinoids isolated from *cannabis* plants include, but are not limited to, Tetrahydrocannabinol (THC), Cannabidiol (CBD), CBG (Cannabigerol), CBC (Cannabichromene), CBL (Cannabicyclol), CBV (Cannabivarin), THCV (Tetrahydrocannabivarin), CBDV (Cannabidivarin), CBCV (Cannabichromevarin), CBGV (Cannabigerovarin), and CBGM (Cannabigerol Monomethyl Ether). In the *Cannabis* plant, cannabinoids are synthesized and accumulated as cannabinoid acids (e.g., cannabidiolic acid (CBDA)). When the herbal product is dried, stored, or heated, the acids decarboxylize gradually or completely into neutral forms (e.g., CBDA→CBD).

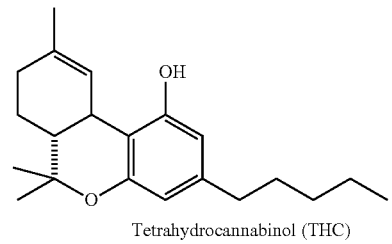

Tetrahydrocannabinol (THC)

Known as delta-9-tetrahydrocannabinol ($\Delta$9-THC), THC is the principal psychoactive constituent (or cannabinoid) of the *cannabis* plant. The initially synthesized and accumulated form in plant is THC acid (THCA).

THC has mild to moderate analgesic effects, and *cannabis* can be used to treat pain by altering transmitter release on dorsal root ganglion of the spinal cord and in the periaqueductal gray. Other effects include relaxation, alteration of visual, auditory, and olfactory senses, fatigue, and appetite stimulation. THC has marked antiemetic properties, and may also reduce aggression in certain subjects (Hoaken (2003). "Drugs of abuse and the elicitation of human aggressive behavior". *Addictive Behaviors* 28: 1533-1554).

The pharmacological actions of THC result from its partial agonist activity at the cannabinoid receptor CBI, located mainly in the central nervous system, and the $CB_2$ receptor, mainly expressed in cells of the immune system (Pertwee, 2006, "The pharmacology of cannabinoid receptors and their ligands: An overview." International Journal of Obesity 30: S13-S18.) The psychoactive effects of THC are primarily mediated by its activation of CB1G-protein coupled receptors, which result in a decrease in the concentration of the second messenger molecule cAMP through inhibition of adenylate cyclase (Elphick et al., 2001, "The neurobiology and evolution of cannabinoid signaling." *Philosophical Transactions of the Royal Society B: Biological Sciences* 356 (1407): 381-408.) It is also suggested that THC has an anticholinesterase action which may implicate it as a potential treatment for Alzheimer's and Myasthenia (Eubanks et al., 2006, "A Molecular Link Between the Active Component of Marijuana and Alzheimer's Disease Pathology." Molecular Pharmaceutics 3 (6): 773-7).

In the *cannabis* plant, THC occurs mainly as tetrahydrocannabinolic acid (THCA, 2-COOH-THC). Geranyl pyrophosphate and olivetolic acid react, catalyzed by an enzyme to produce cannabigerolic acid, which is cyclized by the enzyme THC acid synthase to give THCA. Over time, or when heated, THCA is decarboxylated producing THC. The pathway for THCA biosynthesis is similar to that which produces the bitter acid humulene in hops. See Fellermeier et al., (1998, "Prenylation of olivetolate by a hemp transferase yields cannabigerolic acid, the precursor of tetrahydrocannabinol". *FEBS Letters* 427 (2): 283-5); de Meijer et al. I, II, III, and IV (I: 2003, Genetics, 163:335-346; II: 2005, *Euphytica*, 145:189-198; III: 2009, *Euphytica*, 165:293-311; and IV: 2009, *Euphytica*, 168:95-112.)

Non-limiting examples of THC variants include:

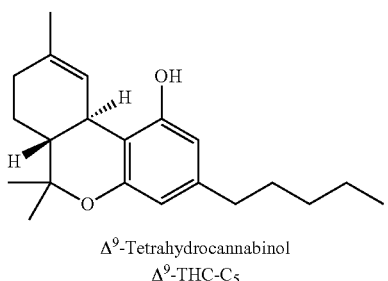

$\Delta^9$-Tetrahydrocannabinol
$\Delta^9$-THC-$C_5$

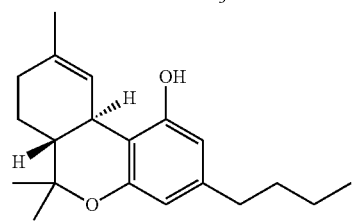

$\Delta^9$-Tetrahydrocannabinol-$C_4$
$\Delta^9$-THC-$C_4$

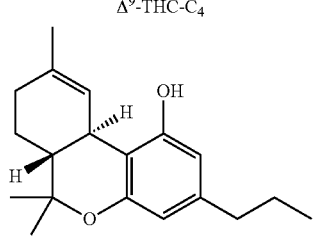

$\Delta^9$-Tetrahydrocannabivarin
$\Delta^9$-THCV-$C_3$

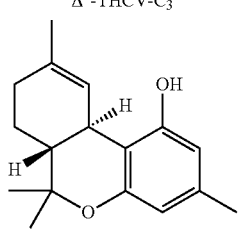

$\Delta^9$-Tetrahydrocannabiorcol
$\Delta^9$-THCO-$C_1$

-continued

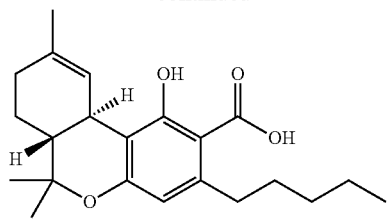

$\Delta^9$-Tetrahydrocannabinolic acid A
$\Delta^9$-THCA-$C_5$ A

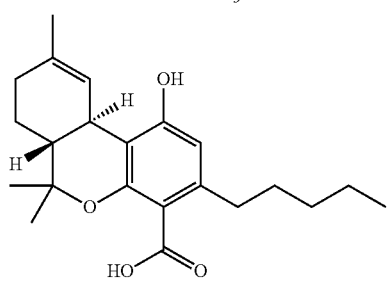

$\Delta^9$-Tetrahydro-cannabinolic acid B
$\Delta^9$-THCA-$C_5$ B

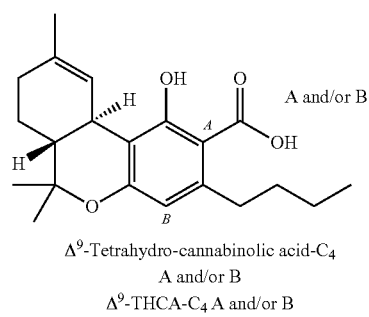

$\Delta^9$-Tetrahydro-cannabinolic acid-$C_4$
A and/or B
$\Delta^9$-THCA-$C_4$ A and/or B

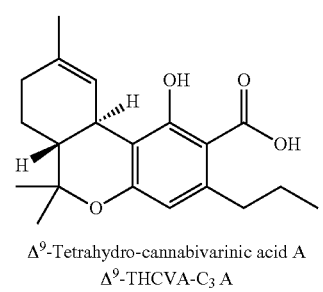

$\Delta^9$-Tetrahydro-cannabivarinic acid A
$\Delta^9$-THCVA-$C_3$ A

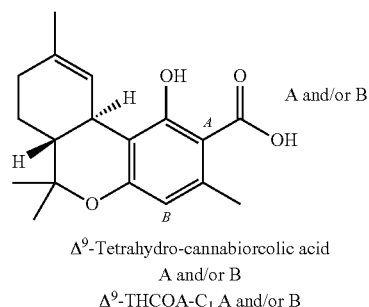

$\Delta^9$-Tetrahydro-cannabiorcolic acid
A and/or B
$\Delta^9$-THCOA-$C_1$ A and/or B

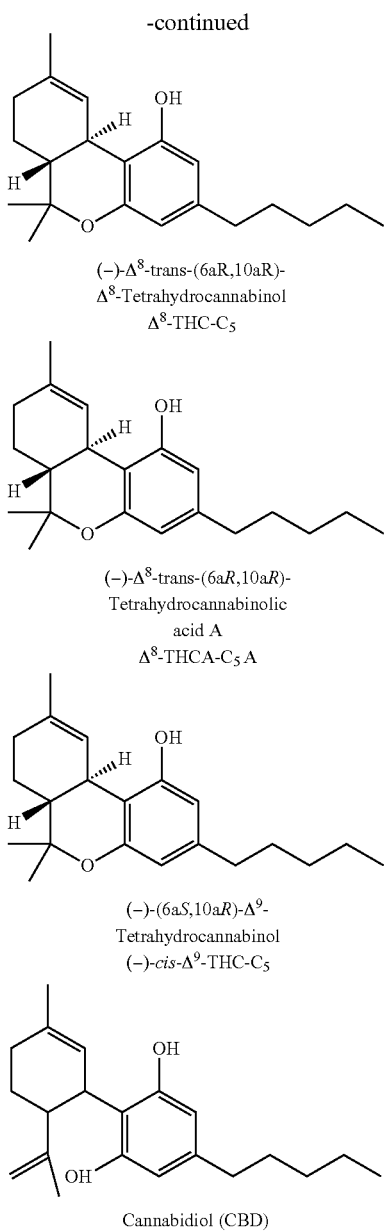

(−)-Δ⁸-trans-(6aR,10aR)-
Δ⁸-Tetrahydrocannabinol
Δ⁸-THC-C₅

(−)-Δ⁸-trans-(6aR,10aR)-
Tetrahydrocannabinolic
acid A
Δ⁸-THCA-C₅A (−)-(6aS,10aR)-Δ⁹-
Tetrahydrocannabinol
(−)-cis-Δ⁹-THC-C₅

Cannabidiol (CBD)

CBD is a cannabinoid found in *cannabis*. Cannabidiol has displayed sedative effects in animal tests (Pickens, 1981, "Sedative activity of *cannabis* in relation to its delta'-trans-tetrahydrocannabinol and cannabidiol content". *Br. J. Pharmacol.* 72 (4): 649-56). Some research, however, indicates that CBD can increase alertness, and attenuate the memory-impairing effect of THC. (Nicholson et al., June 2004, "Effect of Delta-9-tetrahydrocannabinol and cannabidiol on nocturnal sleep and early-morning behavior in young adults" *J Clin Psychopharmacol* 24 (3): 305-13; Morgan et al., 2010, "Impact of cannabidiol on the acute memory and psychotomimetic effects of smoked *cannabis*: naturalistic study, *The British Journal of Psychiatry*, 197:258-290). It may decrease the rate of THC clearance from the body, perhaps by interfering with the metabolism of THC in the liver. Medically, it has been shown to relieve convulsion, inflammation, anxiety, and nausea, as well as inhibit cancer cell growth (Mechoulam, et al., 2007, "Cannabidiol—recent advances". *Chemistry & Biodiversity* 4 (8): 1678-1692.)

Recent studies have shown cannabidiol to be as effective as atypical antipsychotics in treating schizophrenia (Zuardi et al., 2006, "Cannabidiol, a *Cannabis sativa* constituent, as an antipsychotic drug" *Braz. J. Med. Biol. Res.* 39 (4): 421-429.). Studies have also shown that it may relieve symptoms of dystonia (Consroe, 1986, "Open label evaluation of cannabidiol in dystonic movement disorders". *The International journal of neuroscience* 30 (4): 277-282). CBD reduces growth of aggressive human breast cancer cells in vitro and reduces their invasiveness (McAllister et al., 2007, "Cannabidiol as a novel inhibitor of Id-1 gene expression in aggressive breast cancer cells". *Mol. Cancer Ther.* 6 (11): 2921-7.)

Cannabidiol has shown to decrease activity of the limbic system (de Souza Crippa et al., "Effects of Cannabidiol (CBD) on Regional Cerebral Blood Flow", *Neuropsychopharmacology* 29 (2): 417-426.), and to decrease social isolation induced by THC (Malon et al., "Cannabidiol reverses the reduction in social interaction produced by low dose Δ9-tetrahydrocannabinol in rats", Pharmacology Biochemistry and Behavior 93 (2): 91-96.) It's also shown that Cannabidiol reduces anxiety in social anxiety disorder (Bergamaschi et al., 2003, "Cannabidiol Reduces the Anxiety Induced by Simulated Public Speaking in Treatment-Naïve Social Phobia Patients". *Neuropsychopharmacology* 36 (6): 1219-1226). Cannabidiol has also been shown as being effective in treating an often drug-induced set of neurological movement disorders known as dystonia (Snider et al., 1985, "Beneficial and Adverse Effects of Cannabidiol in a Parkinson Patient with Sinemet-Induced Dystonic Dyskinesia", *Neurology*, (Suppl 1): 201.) Morgan et al. reported that strains of *cannabis* which contained higher concentrations of Cannabidiol did not produce short-term memory impairment vs. strains which contained similar concentrations of THC (2010, "Impact of cannabidiol on the acute memory and psychotomimetic effects of smoked *cannabis*: naturalistic study: naturalistic study [corrected."]. *British Journal of Psychiatry* 197 (4): 285-90.)

Cannabidiol acts as an indirect antagonist of cannabinoid agonists. CBD is an antagonist at the putative new cannabinoid receptor, GPR55. Cannabidiol has also been shown to act as a 5-HT1A receptor agonist, an action which is involved in its antidepressant, anxiolytic, and neuroprotective effects. Cannabidiol is also an allosteric modulator at the Mu and Delta opioid receptor sites.

*Cannabis* produces CBD-carboxylic acid through the same metabolic pathway as THC, until the last step, where CBDA synthase performs catalysis instead of THCA synthase. See Marks et al. (2009, "Identification of candidate genes affecting Δ9-tetrahydrocannabinol biosynthesis in *Cannabis sativa*". Journal of Experimental Botany 60 (13): 3715-3726.) and Meijer et al. I, II, III, and IV. Non-limiting examples of CBD variants include:

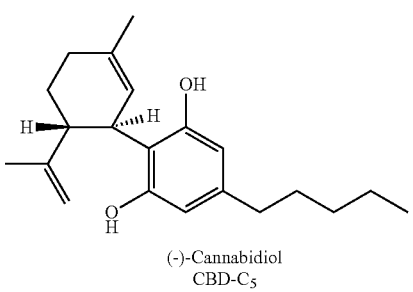

(-)-Cannabidiol
CBD-C₅

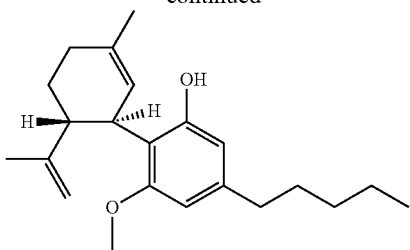

Cannabidiol
momomethyl ether
CBDM-C$_5$

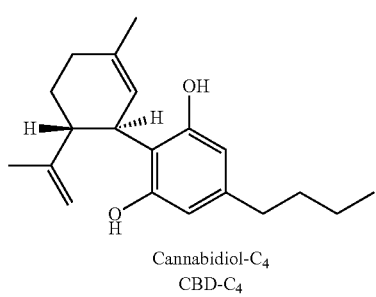

Cannabidiol-C$_4$
CBD-C$_4$

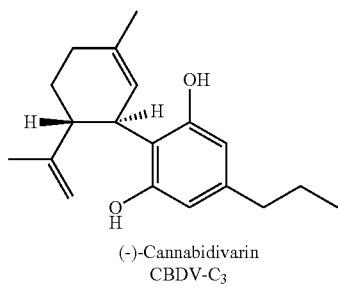

(-)-Cannabidivarin
CBDV-C$_3$

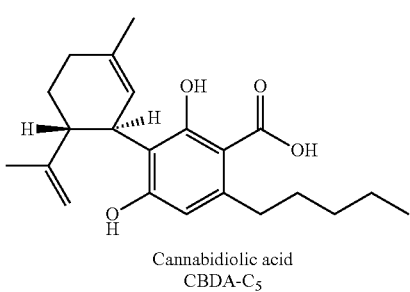

Cannabidivarin
CBD-C$_1$

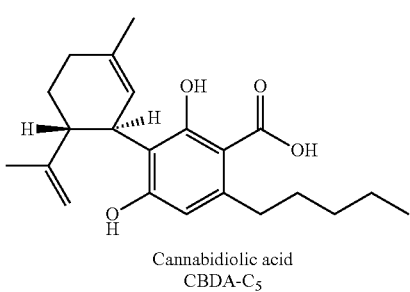

Cannabidiolic acid
CBDA-C$_5$

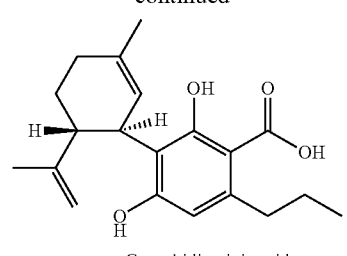

Cannabidivarinic acid
CBDVA-C$_3$

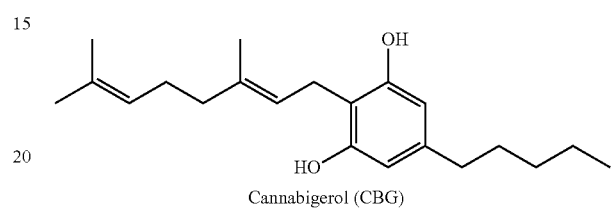

Cannabigerol (CBG)

CBG is a non-psychoactive cannabinoid found in the *Cannabis* genus of plants. Cannabigerol is found in higher concentrations in hemp rather than in varieties of *Cannabis* cultivated for high THC content and their corresponding psychoactive properties. Cannabigerol has been found to act as a high affinity α2-adrenergic receptor agonist, moderate affinity 5-HT1A receptor antagonist, and low affinity CB1 receptor antagonist. It also binds to the CB$_2$ receptor. Cannabigerol has been shown to relieve intraocular pressure, which may be of benefit in the treatment of glaucoma (Craig et al. 1984, "Intraocular pressure, ocular toxicity and neurotoxicity after administration of cannabinol or cannabigerol", Experimental eye research 39 (3):251-259). Cannabigerol has also been shown to reduce depression in animal models (U.S. patent application Ser. No. 11/760,364). Non-limiting examples of CBG variants include:

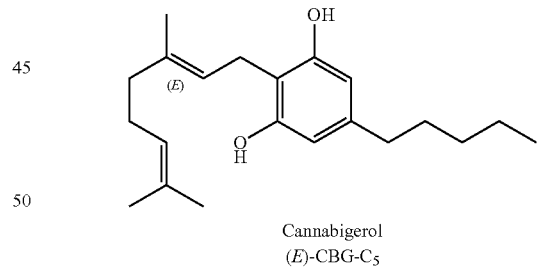

Cannabigerol
(E)-CBG-C$_5$

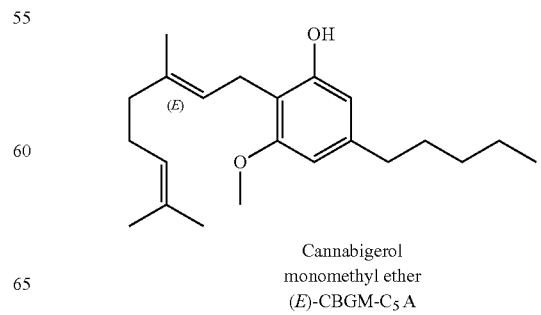

Cannabigerol
monomethyl ether
(E)-CBGM-C$_5$ A

-continued

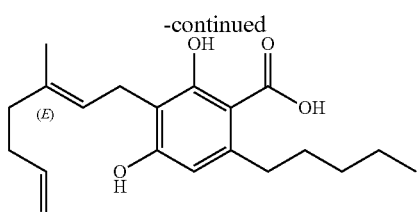

Cannabinerolic acid A
(Z)-CBGA-C$_5$A

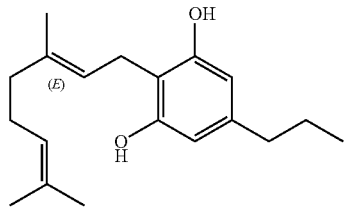

Cannabigervarin
(E)-CBGV-C$_3$

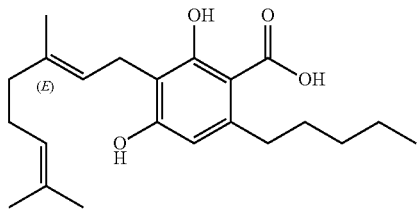

Cannabinerolic acid A
(E)-CBGA-C$_5$A

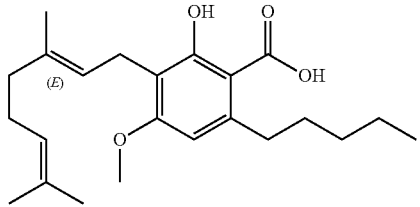

Cannabigerolic acid A
monomethyl ether
(E)-CBGAM-C$_5$A

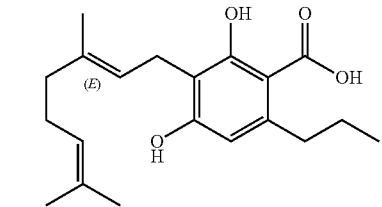

Cannabigerovarinic acid A
(E)-CBGVA-C$_3$A

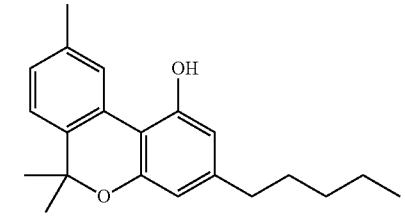

Cannabinol (CBN)

CBN is a psychoactive substance cannabinoid found in *Cannabis sativa* and *Cannabis indica/afghanica*. It is also a metabolite of tetrahydrocannabinol (THC). CBN acts as a weak agonist of the CB1 and CB2 receptors, with lower affinity in comparison to THC. Non-limiting examples of CBN variants include:

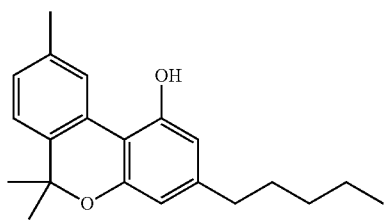

Cannabinol
CBN-C$_5$

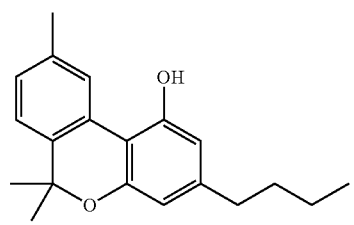

Cannabinol-C$_4$
CBN-C$_4$

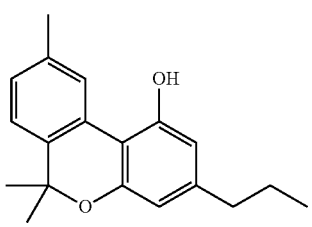

Cannabivarin
CBN-C$_3$

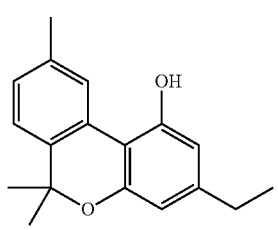

Cannabinol-C$_2$
CBN-C$_2$

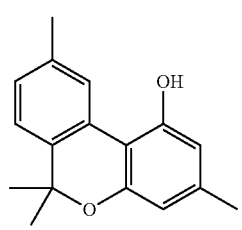

Cannabiorcol
CBN-C$_1$

-continued

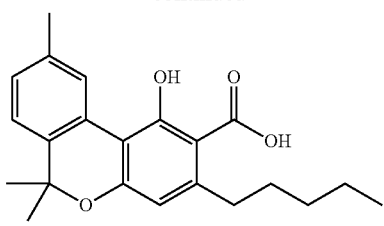

Cannabinolic acid A
CBNA-C5 A

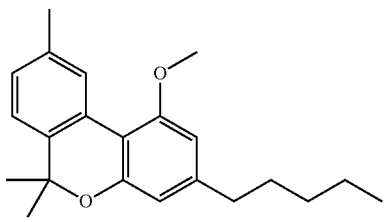

Cannabinol methyl ether
CBNM-C5

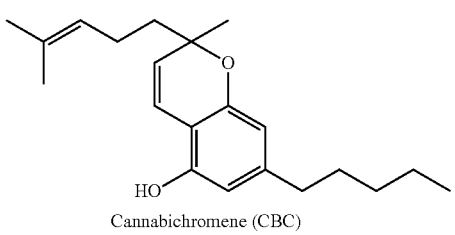

Cannabichromene (CBC)

CBC bears structural similarity to the other natural cannabinoids, including tetrahydrocannabinol, tetrahydrocannabivarin, cannabidiol, and cannabinol, among others. Evidence has suggested that it may play a role in the anti-inflammatory and anti-viral effects of *cannabis*, and may contribute to the overall analgesic effects of *cannabis*. Non-limiting examples of CBC variants include:

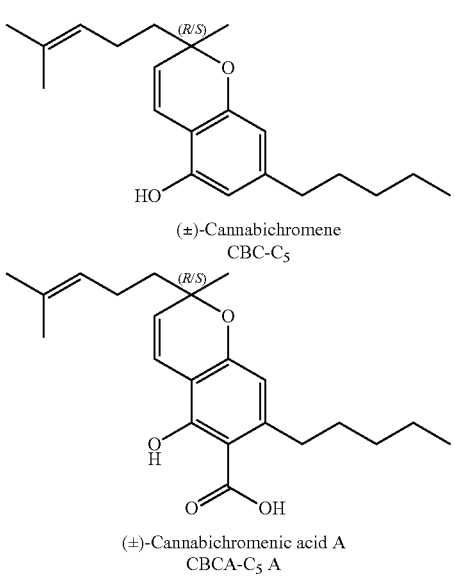

(±)-Cannabichromene
CBC-C5

(±)-Cannabichromenic acid A
CBCA-C5 A

-continued

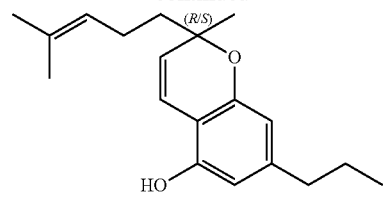

(±)-Cannabivarichromene,
(±)-Cannabivarichromevarin
CBCV-C3

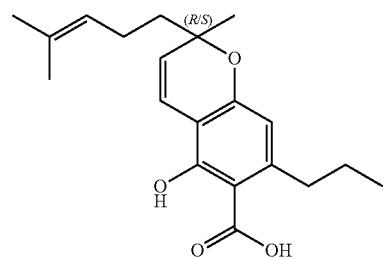

(±)-Cannabichromevarinic
acid A
CBCVA-C3 A

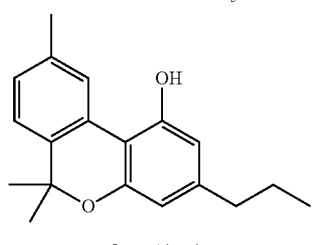

Cannabivarin
(CBV)

Cannabivarin, also known as cannabivarol or CBV, is a non-psychoactive cannabinoid found in minor amounts in the hemp plant *Cannabis sativa*. It is an analog of cannabinol (CBN) with the side chain shortened by two methylene bridges (—CH2-). CBV is an oxidation product of tetrahydrocannabivarin (THCV, THV).

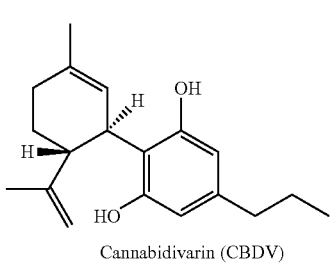 [SMILES: C=C(C)[C@@H]1CCC(C)=C[C@H]1c1c(O)cc(CCC)cc1O]

Cannabidivarin (CBDV)

CBDV is a non-psychoactive cannabinoid found in *Cannabis*. It is a homolog of cannabidiol (CBD), with the side-chain shortened by two methylene bridges (CH2 units). Cannabidivarin has been found reduce the number and severity of seizures in animal models (U.S. patent application Ser. No. 13/075,873). Plants with relatively high levels of CBDV have been reported in feral populations of *C. indica* (=*C. sativa* ssp. *indica* var. *kafiristanica*) from northwest India, and in hashish from Nepal.

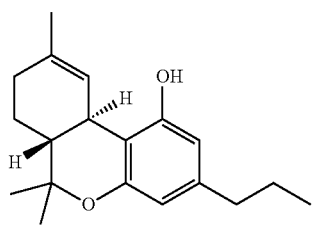

Tetrahydrocannabivarin (THCV, THV)

THCV, or THV is a homologue of tetrahydrocannabinol (THC) having a propyl (3-carbon) side chain. This terpenophenolic compound is found naturally in *Cannabis*, sometimes in significant amounts. Plants with elevated levels of propyl cannabinoids (including THCV) have been found in populations of *Cannabis sativa* L. ssp. *indica* (=*Cannabis indica* Lam.) from China, India, Nepal, Thailand, Afghanistan, and Pakistan, as well as southern and western Africa. THCV has been shown to be a CB1 receptor antagonist, i.e. it blocks the effects of THC. Tetrahydrocannabinol has been shown to increase metabolism, help weight loss and lower cholesterol in animal models (U.S. patent application Ser. No. 11/667,860)

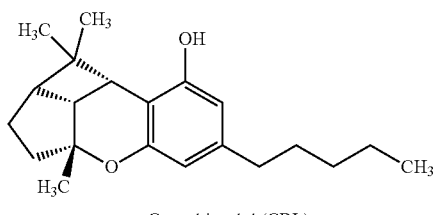

Cannabicyclol (CBL)

Cannabicyclol (CBL) is a non-psychotomimetic cannabinoid found in the *Cannabis* species. CBL is a degradative product like cannabinol. Light converts cannabichromene to CBL. Non-limiting examples of CBL variants include:

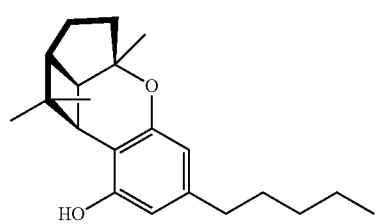

(±)-(1a$S$,3a$R$,8b$R$,8c$R$)-
Cannabicyclol
CBL-$C_5$

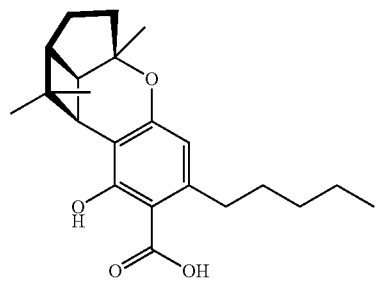

(±)-(1a$S$,3a$R$,8b$R$,8c$R$)-
Cannabicyclolic acid A
CBLA-$C_5$A

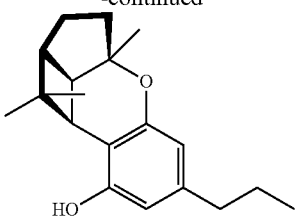

(±)-(1a$S$,3a$R$,8b$R$,8c$R$)-
Cannabicyclovarin
CBLV-$C_3$

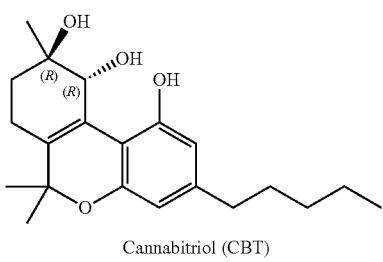

Cannabitriol (CBT)

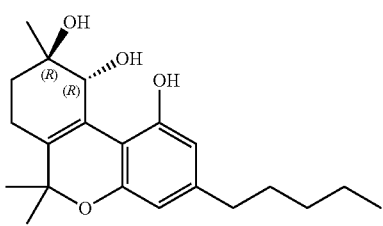

(−)-(9$R$,10$R$)-*trans*-
Cannabitriol
(−)-*trans*-CBT-$C_5$

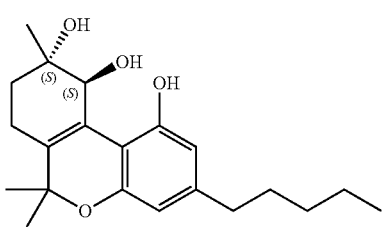

(+)-(9$S$,10$S$)-Cannabitriol
(+)-*trans*-CBT-$C_5$

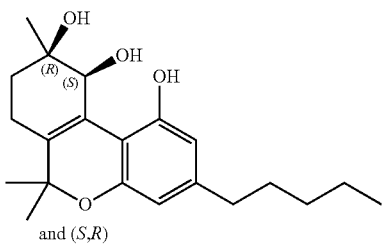

and ($S$,$R$)

(±)-(9$R$,10$S$/9$S$,10$R$)-
Cannabitriol
(±)-*cis*-CBT-$C_5$

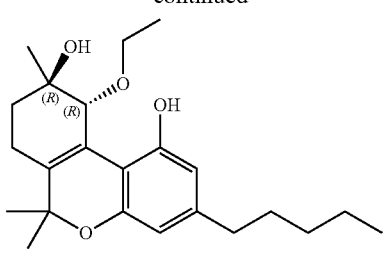

(−)-(9R,10R)-trans-
10-O-Ethyl-cannabitriol
(−)-trans-CBT-OEt-$C_5$

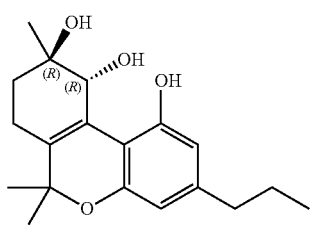

and (S,S)
(±)-(9R,10R/9S,10S)-
Cannabitriol-$C_3$
(±)-trans-CBT-$C_3$

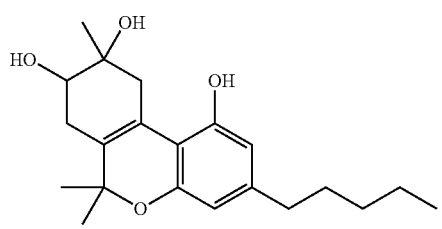

8,9-Dihydroxy-$\Delta^{6a(10a)}$-
tetrahydrocannabinol
8,9-Di-OH-CBT-$C_5$

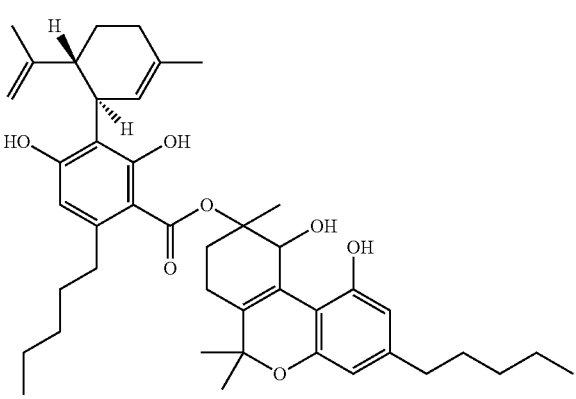

Cannabidiolic acid A
cannabitriol ester
CBDA-$C_5$ 9-OH-CBT-$C_5$ ester

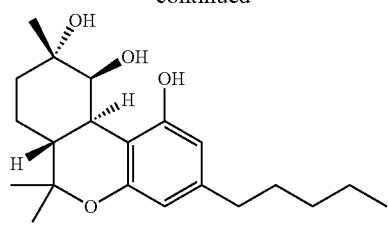

(−)-(6aR,9S,10S,10aR)-
9,10-Dihydroxy-
hexahydrocannabinol,
Cannabiripsol
Cannabiripsol-$C_5$

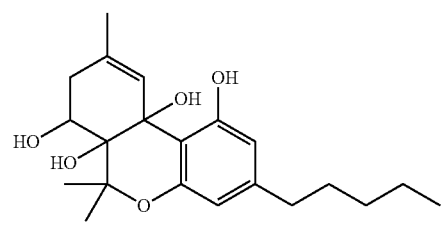

(−)-6a,7,10a-Trihydroxy-
$\Delta^9$-tetrahydrocannabinol
(−)-Cannabitetrol

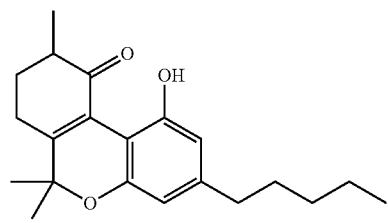

10-Oxo-$\Delta^{6a(10a)}$-
tetrahydrocannabinol
OTHC

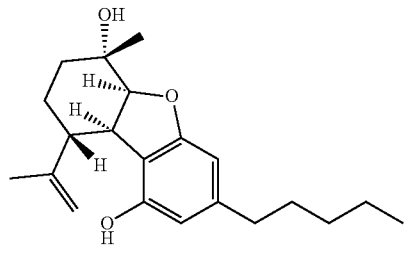

Cannabielsoin-type (CBE)

Non-limiting examples of CBE variants include:

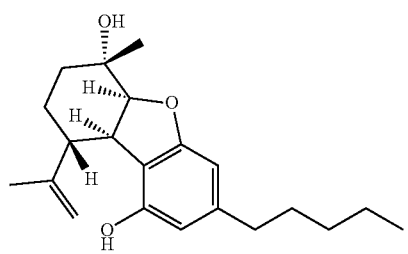

(5aS,6S,9R,9aR)-
Cannabielsoin
CBE-$C_5$

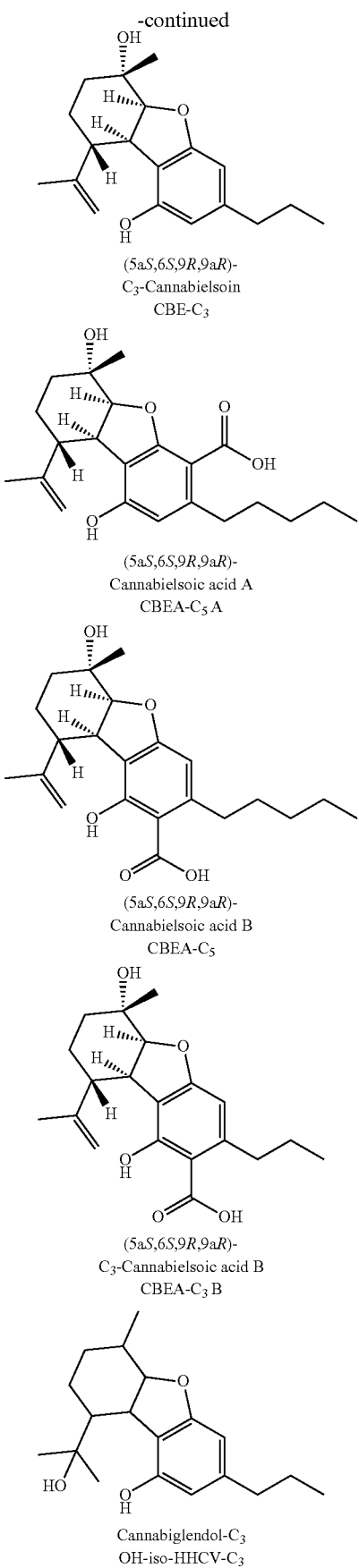
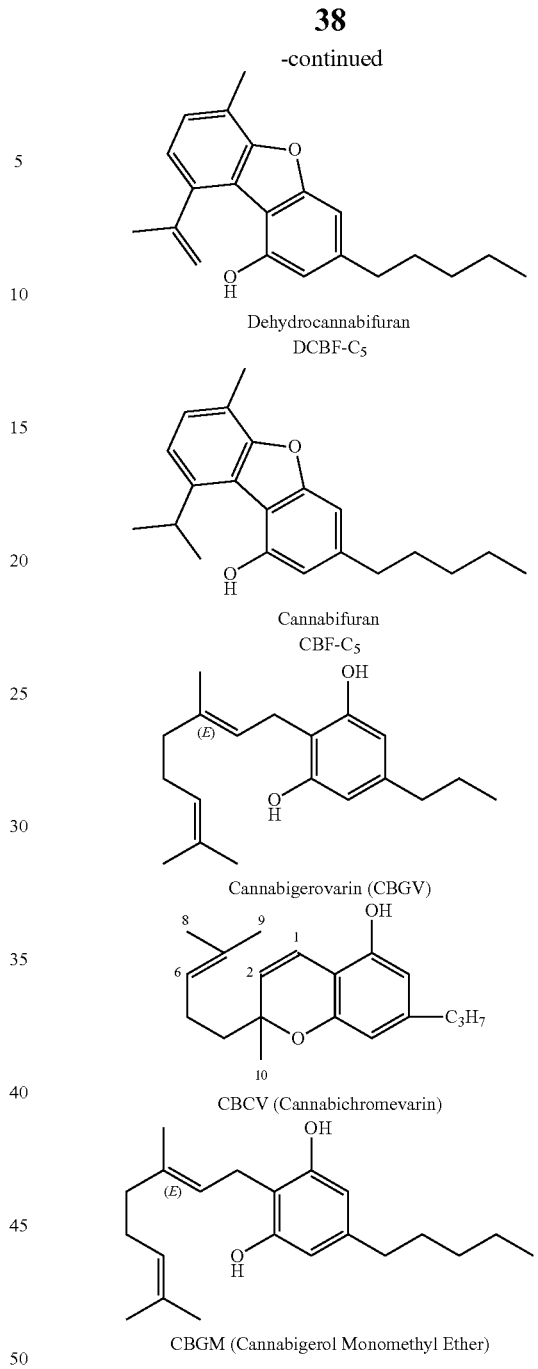

More details of cannabinoids synthesis and the properties and uses of these cannabinoids are described in Russo (2011, Taming THC: potential *cannabis* synergy and phytocannabinoid-terpenoid entourage effects, *British Journal of Pharmacology*, 163:1344-1364), Russo et al. (2006, A tale of two cannabinoids: the therapeutic rationale for combining tetrahydrocannabinol and cannabidiol, *Medical Hypothesis*, 2006, 66:234-246), Celia et al. (Impact of cannabidiol on the acute memory and psychotomimetic effects of smoked *cannabis*: naturalistic study, *The British Journal of Psychiatry*, 201, 197:285-290), de Mello Schier et al., (Cannabidiol, a *Cannabis sativa* constituent, as an anxiolytic drug, *Rev. Bras. Psiquiatr,* 2012, 34(S1):S104-S117), and Zhornitsky et al. (Cannabidiol in Humans—the Quest for Therapeutic Targets, Pharmaceuticals, 2012, 5:529-552), each of which is herein incorporated by reference in its entirety for all purposes. Please see Table 1 for a non-limiting list of medical uses for cannabinoids.

TABLE 1

Non-limiting List of Medical Uses for Cannabinoids

| | MEDICAL USES | CANNABINOID | REFERENCES |
|---|---|---|---|
| 1 | Distonia, Akathisia (Anti convulsant) | CBD | (a) Consroe, 1986, *The International journal of neuroscience* 30 (4): 277-282<br>(b) Snider et al., 1985, *Neurology*, (Suppl 1): 201. |
| 2 | Glaucoma (lowers intraocular pressure) | CBD<br>CBG | (a) Colasanti et al, Exp. Eye Res. 30: 251-259, 1984<br>(b) Gen. Pharmac. 15: 479-484, 1984<br>(c) Craig et al. 1984, Experimental eye research 39 (3): 251-259 |
| 3 | Ischemic disease (Alzheimer's, Parkinson's, Down Syndrome, HIV, Dementia) | CBD | (a) U.S. Pat. No. 6,630,507<br>(b) Snider et al., 1985, "Beneficial and Adverse Effects of Cannabidiol in a Parkinson Patient with Sinemet-Induced Dystonic Dyskinesia". *Neurology*, (Suppl 1): 201. |
| 4 | Good for patients treated with oxidant-inducing agents for chemotherapy, radiation. | CBD | (a) U.S. Pat. No. 6,630,507 |
| 5 | Motion Sickness (Anti- emetic) | CBD | (a) U.S. Pat. No. 8,034,843 GW Pharma experiments on Shrews<br>(b) Mechoulam, et al., 2007, *Chemistry & Biodiversity* 4 (8): 1678-1692. |
| 6 | Pain- Brachial plexus avulsion | THC<br>THC: CBD | (a) US 20060135599 GW Pharma |
| 7 | Pain and inflammation- Arthritis | CBD: THC | (a) US20080139667<br>(b) Mechoulam, et al., 2007, *Chemistry & Biodiversity* 4 (8): 1678-1692. |
| 8 | Anti Cancer- cell movement | CBD: THC<br>CBD | (a) US20080262099<br>(b) Mechoulam, et al., 2007, *Chemistry & Biodiversity* 4 (8): 1678-1692.<br>(c) McAllister et al., 2007, *Mol. Cancer Ther.* 6 (11): 2921-7. |
| 9 | Anti Convulsant (against seizures) | CBDV<br>CBD | (a) US20120004251<br>(b) US20120165402<br>(d) Mechoulam, et al., 2007, *Chemistry & Biodiversity* 4 (8): 1678-1692.<br>(a) Carlini et al., J. Clin. Pharmacol. 21: 417S-427S, 1981<br>(b) Karler et al., J. Clin. Pharmacol. 21: 437S-448S, 1981<br>(c) Consroe et al., J. Clin Pharmacol. 21: 428S-436S, 1981 |
| 10 | Neurological Pain (MS related) | THC: CBD | (a) US20100035978 |
| 11 | Weight loss | THCV | (b) US20090306221<br>(c) US20080119544 |
| 12 | Anti-Depressant | CBG | (a) US20080031977<br>(b) U.S. 60/813,814 |
| 13 | Irritable Bowel Syndrome (Crohns) | THC: CBD | (c) EP 1361864<br>(d) EP 1542657<br>(e) US20100286098 |
| 14 | Type II diabetes | THCV: CBD | (a) US20110082195<br>(b) |
| 15 | Anti-Psychotic | THCV: CBD | (c) US20110038958<br>(d) Zuardi et al., 2006, *Braz. J. Med. Biol. Res.* 39 (4): 421-429. |
| 16 | Cancer Pain | THC: CBD | (e) US20110230549 |
| 17 | Anxiety Reduction | CBD | (a) Mechoulam, et al., 2007, *Chemistry & Biodiversity* 4 (8): 1678-1692.<br>(b) Bergamaschi et al., 2003, *Neuropsychopharmacology* 36 (6): 1219-1226 |

Terpenes

Terpenes are a large and diverse class of organic compounds, produced by a variety of plants. They are often strong smelling and thus may have had a protective function. Terpenes are derived biosynthetically from units of isoprene, which has the molecular formula $C_5H_8$. The basic molecular formulae of terpenes are multiples of that, $(C_5H_8)_n$ where n is the number of linked isoprene units. The isoprene units may be linked together "head to tail" to form linear chains or they may be arranged to form rings. Non-limiting examples of terpenes include Hemiterpenes, Monoterpenes, Sesquiterpenes, Diterpenes, Sesterterpenes, Triterpenes, Sesquarterpenes, Tetraterpenes, Polyterpenes, and Norisoprenoids.

Terpenoids, a.k.a. isoprenoids, are a large and diverse class of naturally occurring organic chemicals similar to terpenes, derived from five-carbon isoprene units assembled and modified in thousands of ways. Most are multicyclic structures that differ from one another not only in functional groups but also in their basic carbon skeletons. Plant terpenoids are used extensively for their aromatic qualities. They play a role in traditional herbal remedies and are under investigation for antibacterial, antineoplastic, and other pharmaceutical functions. The terpene Linalool for example, has been found to have anti-convulsant properties (Elisabetsky et al., Phytomedicine, May 6(2):107-13 1999). Well-known terpenoids include citral, menthol, camphor, salvinorin A in the plant *Salvia divinorum*, and the cannabinoids found in *Cannabis*. Non-limiting examples of terpenoids include, Hemiterpenoids, 1 isoprene unit (5 carbons); Monoterpenoids, 2 isoprene units (10C); Sesquiterpenoids, 3 isoprene units (15C); Diterpenoids, 4 isoprene units (20C) (e.g. ginkgolides); Sesterterpenoids, 5 isoprene units (25C); Triterpenoids, 6 isoprene units (30C) (e.g. sterols); Tetraterpenoids, 8 isoprene units (40C) (e.g. carotenoids); and Polyterpenoid with a larger number of isoprene units.

Terpenoids are mainly synthesized in two metabolic pathways: mevalonic acid pathway (a.k.a. HMG-CoA reductase pathway, which takes place in the cytosol) and MEP/DOXP pathway (a.k.a. The 2-C-methyl-D-erythritol 4-phosphate/1-deoxy-D-xylulose 5-phosphate pathway, non-mevalonate pathway, or mevalonic acid-independent pathway, which takes place in plastids). Geranyl pyrophosphate (GPP), which is used by *cannabis* plants to produce cannabinoids, is formed by condensation of dimethylallyl pyrophosphate (DMAPP) and isopentenyl pyrophosphate (IPP) via the catalysis of GPP synthase. Alternatively, DMAPP and IPP are ligated by FPP synthase to produce farnesyl pyrophosphate (FPP), which can be used to produce sesquiterpenoids. Geranyl pyrophosphate (GPP) can also be converted into monoterpenoids by limonene synthase.

In addition to cannabinoids, *cannabis* also produces over 120 different terpenes (Russo 2011, Taming THC: potential *cannabis* synergy and phytocannabinoid-terpenoid entourage effects, *British Journal of Pharmacology*, 163:1344-1364). Within the context and verbiage of this document the terms 'terpenoid' and 'terpene' are used interchangeably. Cannabinoids are odorless, so terpenoids are responsible for the unique odor of *cannabis*, and each variety has a slightly different profile that can potentially be used as a tool for identification of different varieties or geographical origins of samples (Hillig 2004. "A chemotaxonomic analysis of terpenoid variation in *Cannabis*", Biochem System and Ecology 875-891). It also provides a unique and complex organoleptic profile for each variety that is appreciated by both novice users and connoisseurs. In addition to many circulatory and muscular effects, some terpenes interact with neurological receptors. A few terpenes produced by *cannabis* plants also bind weakly to Cannabinoid receptors. Some terpenes can alter the permeability of cell membranes and allow in either more or less THC, while other terpenes can affect serotonin and dopamine chemistry as neurotransmitters. Terpenoids are lipophilic, and can interact with lipid membranes, ion channels, a variety of different receptors (including both G-protein coupled odorant and neurotransmitter receptors), and enzymes. Some are capable of absorption through human skin and passing the blood brain barrier.

Both experts and consumers believe that there are biochemical and phenomenological differences between different varieties of *cannabis*, which are attributed to their unique relative cannabinoid and terpenoid ratios. This is known as the entourage effect and is generally considered to result in plants providing advantages over only using the natural products that are isolated from them (Russo 2011, Taming THC: potential *cannabis* synergy and phytocannabinoid-terpenoid entourage effects, *British Journal of Pharmacology*, 163:1344-1364).

These advantages include synergy with THC, the primary active ingredient, and also mitigation of side effects from THC (McPartland and Russo 2001 "*Cannabis* and *Cannabis* Extracts: Greater Than the Sum of Their Parts?" Hayworth Press). Terpenoids can be extracted from the plant material by steam distillation (giving you essential oil) or vaporization, however the yield varies greatly by plant tissue, type of extraction, age of material, and other variables (McPartland and Russo 2001 "*Cannabis* and *Cannabis* Extracts: Greater Than the Sum of Their Parts?" Hayworth Press). Typically the yield of terpenoids in *cannabis* is less than 1% by weight on analysis; however it is thought that they may comprise up to 10% of the trichome content. Monoterpenoids are especially volatile, thus decreasing their yield relative to sesquiterpenoids (Russo 2011, Taming THC: potential *cannabis* synergy and phytocannabinoid-terpenoid entourage effects, *British Journal of Pharmacology*, 163:1344-1364).

D-Limonene is a monoterpenoid that is widely distributed in nature and often associated with citrus. It has strong anxiolytic properties in both mice and humans, apparently increasing serotonin and dopamine in mouse brain. D-limonene has potent anti-depressant activity when inhaled. It is also under investigation for a variety of different cancer treatments, with some focus on its hepatic metabolite, perillic acid. There is evidence for activity in the treatment of dermatophytes and gastro-oesophageal reflux, as well as having general radical scavenging properties (Russo 2011, Taming THC: potential *cannabis* synergy and phytocannabinoid-terpenoid entourage effects, *British Journal of Pharmacology*, 163:1344-1364).

β-Myrcene is a monoterpenoid also found in *cannabis*, and has a variety of pharmacological effects. It is often associated with a sweet fruit like taste. It reduces inflammation, aids sleep, and blocks hepatic carcinogenesis, as well as acting as an analgesic and muscle relaxant in mice. When β-myrcene is combined with Δ9-THC it could intensify the sedative effects of Δ9-THC, causing the well-known "couch-lock" effect that some *cannabis* users experience (Russo 2011, Taming THC: potential *cannabis* synergy and phytocannabinoid-terpenoid entourage effects, *British Journal of Pharmacology*, 163:1344-1364).

D-Linalool is a monoterpenoid with very well-known anxiolytic effects. It is often associated with lavender, and frequented used in aromatherapy for its sedative impact. It acts as a local anaesthetic and helps to prevent scarring from burns, is anti-nociceptive in mice, and shows antiglutamatergic and anticonvulsant activity. Its effects on glutamate and GABA neurotransmitter systems are credited with giving it its sedative, anxiolytic, and anticonvulsant activities (Russo 2011, Taming THC: potential *cannabis* synergy and phytocannabinoid-terpenoid entourage effects, *British Journal of Pharmacology*, 163:1344-1364).

α-Pinene is a monoterpene common in nature, also with a plethora of effects on mammals and humans. It acts as an acetylcholinesterase inhibitor which aids memory and counteracts the short-term memory loss associated with $\Delta_9$-THC intoxication, is an effective antibiotic agent, and shows some activity against MRSA. In addition, α-pinene is a bronchodilator in humans and has anti-inflammatory properties via the prostaglandin E-1 pathway (Russo 2011, Taming THC: potential *cannabis* synergy and phytocannabinoid-terpenoid entourage effects, *British Journal of Pharmacology*, 163:1344-1364).

β-Caryophyllene is often the most predominant sesquiterpenoid in *cannabis*. It is less volatile than the monoterpenoids, thus it is found in higher concentrations in material that has been processed by heat to aid in decarboxylation. It is very interesting in that it is a selective full agonist at the $CB_2$ receptor, which makes it the only phytocannabinoid found outside the *cannabis* genus. In addition, it has anti-inflammatory and gastric cytoprotective properties, and may even have anti-malarial activity.

Caryophyllene oxide is another sesquiterpenoid found in *cannabis*, which has antifungal and anti-platelet aggregation properties. As an aside, it is also the molecule that drug-sniffing dogs are trained to find (Russo 2011, Taming THC: potential *cannabis* synergy and phytocannabinoid-terpenoid entourage effects, *British Journal of Pharmacology*, 163:1344-1364).)

Nerolidol is a sesquiterpene that is often found in citrus peels that exhibits a range of interesting properties. It acts as a sedative, inhibits fungal growth, and has potent anti-malarial and antileishmanial activity. It also alleviated colon adenomas in rats (Russo 2011, Taming THC: potential cannabis synergy and phytocannabinoid-terpenoid entourage effects, *British Journal of Pharmacology*, 163:1344-1364). Phytol is a diterpene often found in *cannabis* extracts. It is a degradation product of chlorophyll and tocopherol. It increases GABA expression and therefore could be responsible the relaxing effects of green tea and wild lettuce. It also prevents vitamin-A induced teratogenesis by blocking the conversion of retinol to its dangerous metabolite, all-trans-retinoic acid (Russo 2011, Taming THC: potential *cannabis* synergy and phytocannabinoid-terpenoid entourage effects, *British Journal of Pharmacology*, 163:1344-1364).

Some of the most commonly found terpenoids in *cannabis* are summarized in Table 2, with their individual organoleptic properties as well as their basic pharmacology.

synergy and phytocannabinoid-terpenoid entourage effects, *British Journal of Pharmacology*, 163:1344-1364). Thus in some embodiments, the present invention teaches the classification of *cannabis* based on the terpene compounds which accumulate at levels sufficient to produce a pharmacologically relevant effect. In other embodiments, the present invention teaches the classification of *cannabis* based on the terpenes which accumulate at levels sufficient to produce a detectable flavor or aroma with the user.

In some embodiments, the present invention teaches systems, apparatuses, and methods of classifying *cannabis* based on the highest accumulating terpenes. Thus in some embodiments, the *cannabis* classification scheme of the present invention is based on the content of the highest 1, 2,

TABLE 2

A Non-limiting List of the Medical Effects of Some of the Most Common Terpenes Found in Cannabis

| Terpenoid | Odor Description | Flavor Description | Suggested Pharmacology |
|---|---|---|---|
| $^a$-pinene | Herbal, piney | Woody, piney, camphoraceous | Anti-inflammatory, bronchodilator, stimulant |
| camphene | Woody, piney | Camphoraceous, cooling, minty | Reduces plasma cholesterol and triglycerides, Antioxidant and free radical scavenger |
| $^b$-pinene | Herbal, cooling, piney | Fresh, piney, woody | Strong antimicrobial |
| myrcene | Spicy, herbaceous | Woody, vegetative, citrus | Anti-inflammatory, sedative, antibiotic, analgesic |
| $^a$-phellandrene | Terpenic, citrus | Terpenic, citrus, lime | Antinociceptive |
| carene | Citrus, sweet | None given | CNS depressant, anti-inflamatory |
| $^a$-terpinene | Woody, citrus, medicinal | Terpenic, woody, piney | Antioxidant |
| limonene | Citrus, fresh | Sweet, orange, citrus | Anxiolytic, antidepressant, immunostimulant |
| $^b$-ocimene | Floral, green | Green, tropical, woody | Possible anti-bacterial |
| $^g$-terpinene | Terpenic, woody | Terpenic, citrus, lime-like | Antioxidant |
| terpinolene | Herbal, woody | Sweet, fresh, piney, citrus | Comforting, calming, anti-oxidant, antifungal |
| linalool | Floral, citrus | Citrus, orange, lemon, floral | Sedative, anxiolytic, immunostimulant |
| fenchol | Camphor, piney | Fresh, piney | Possible stimulant |
| $^a$-terpineol | Floral, piney | None given | Sedative, AChE inhibitor, antioxidant |
| $^b$-caryophyllene | Spicy, woody | Spicy, clove, rosemary | Selective agonist of CB2 receptor, anti-inflammatory, antimalarial |
| $^a$-humulene | Woody | None given | Anti-inflammatory |
| caryophyllene oxide | Woody, sweet | None given | Antifungal, stimulant |

Modern *Cannabis* Classification
New Chemistry-Based Classification of *Cannabis*
Classification Based on Terpene Profiles In some embodiments, the present invention teaches systems, apparatuses, and methods of classification based on chemical analysis, and particularly classifying *cannabis* based on terpene profiles. The terpene profiles of *cannabis* are responsible for producing both the physiological entourage effects as well as the organoleptic properties of a sample. Thus, *cannabis* terpene profiles provide a unique property that can be both measured in the lab (by a Gas Chromatography), and can be recognized in the field by consumers (by smell or taste).

*Cannabis* can produce an estimated 120 different terpenes compounds, each of which may be capable of imparting the *cannabis* sample with a distinctive flavor/aroma, and produce its own individual or entourage (synergistic) physiological effects. Generally speaking however, terpenes are considered to be pharmacologically relevant only when present in concentrations of at least 0.05% within the plant material (Russo 2011, Taming THC: potential *cannabis*

3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 accumulating terpenes. In other embodiments, the *cannabis* classification scheme of the present invention is based on the content of the highest 5 accumulating terpenes. In some embodiments, the *cannabis* classification scheme of the present invention is based on the content of the highest 3 accumulating terpenes.

In other embodiments, the present invention teaches systems, apparatuses, and methods of classifying *cannabis* based on absolute value cutoffs of terpene accumulations in *cannabis* samples. In some embodiments, the *cannabis* classification scheme of the present invention is calculated based on the quantity of terpenes with absolute amounts greater than 0.01%, 0.02%, 0.03%, 0.04%, 0.05%, 0.06%, 0.07%, 0.08%, 0.09%, 0.1%, 0.11%, 0.12%, 0.13%, 0.14%, 0.15%, 0.16%, 0.17%, 0.18%, 0.19%, 0.2%, 0.21%, 0.22%, 0.23%, 0.24%, 0.25%, 0.26%, 0.27%, 0.28%, 0.29%, 0.3%, 0.31%, 0.32%, 0.33%, 0.34%, 0.35%, 0.36%, 0.37%, 0.38%, 0.39%, 0.4%, 0.41%, 0.42%, 0.43%, 0.44%, 0.45%, 0.46%, 0.47%, 0.48%, 0.49%, 0.5%, 0.51%, 0.52%, 0.53%, 0.54%, 0.55%, 0.56%, 0.57%, 0.58%, 0.59%, 0.6%, 0.61%, 0.62%, 0.63%, 0.64%, 0.65%, 0.66%, 0.67%, 0.68%, 0.69%, 0.7%, 0.71%, 0.72%, 0.73%, 0.74%, 0.75%, 0.76%, 0.77%, 0.78%, 0.79%, 0.8%, 0.81%, 0.82%, 0.83%, 0.84%, 0.85%, 0.86%, 0.87%, 0.88%, 0.89%, 0.9%, 0.91%, 0.92%, 0.93%, 0.94%, 0.95%, 0.96%, 0.97%, 0.98%, 0.99%, 1%, 1.01%, 1.02%, 1.03%, 1.04%, 1.05%, 1.06%, 1.07%, 1.08%, 1.09%, 1.1%, 1.11%, 1.12%, 1.13%, 1.14%, 1.15%, 1.16%, 1.17%, 1.18%, 1.19%, 1.2%, 1.21%, 1.22%, 1.23%, 1.24%, 1.25%, 1.26%, 1.27%, 1.28%, 1.29%, 1.3%, 1.31%, 1.32%, 1.33%, 1.34%, 1.35%, 1.36%, 1.37%, 1.38%, 1.39%, 1.4%, 1.41%, 1.42%, 1.43%, 1.44%, 1.45%, 1.46%, 1.47%, 1.48%, 1.49%, 1.5%, 1.51%, 1.52%, 1.53%, 1.54%, 1.55%, 1.56%, 1.57%, 1.58%, 1.59%, 1.6%, 1.61%, 1.62%, 1.63%, 1.64%, 1.65%, 1.66%, 1.67%, 1.68%, 1.69%, 1.7%, 1.71%, 1.72%, 1.73%, 1.74%, 1.75%, 1.76%, 1.77%, 1.78%, 1.79%, 1.8%, 1.81%, 1.82%, 1.83%, 1.84%, 1.85%, 1.86%, 1.87%, 1.88%, 1.89%, 1.9%, 1.91%, 1.92%, 1.93%, 1.94%, 1.95%, 1.96%, 1.97%, 1.98%, 1.99%, 2%, 2.01%, 2.02%, 2.03%, 2.04%, 2.05%, 2.06%, 2.07%, 2.08%, 2.09%, 2.1%, 2.11%, 2.12%, 2.13%, 2.14%, 2.15%, 2.16%, 2.17%, 2.18%, 2.19%, 2.2%, 2.21%, 2.22%, 2.23%, 2.24%, 2.25%, 2.26%, 2.27%, 2.28%, 2.29%, 2.3%, 2.31%, 2.32%, 2.33%, 2.34%, 2.35%, 2.36%, 2.37%, 2.38%, 2.39%, 2.4%, 2.41%, 2.42%, 2.43%, 2.44%, 2.45%, 2.46%, 2.47%, 2.48%, 2.49%, 2.5%, 2.51%, 2.52%, 2.53%, 2.54%, 2.55%, 2.56%, 2.57%, 2.58%, 2.59%, 2.6%, 2.61%, 2.62%, 2.63%, 2.64%, 2.65%, 2.66%, 2.67%, 2.68%, 2.69%, 2.7%, 2.71%, 2.72%, 2.73%, 2.74%, 2.75%, 2.76%, 2.77%, 2.78%, 2.79%, 2.8%, 2.81%, 2.82%, 2.83%, 2.84%, 2.85%, 2.86%, 2.87%, 2.88%, 2.89%, 2.9%, 2.91%, 2.92%, 2.93%, 2.94%, 2.95%, 2.96%, 2.97%, 2.98%, 2.99%, 3%, 3.01%, 3.02%, 3.03%, 3.04%, 3.05%, 3.06%, 3.07%, 3.08%, 3.09%, 3.1%, 3.11%, 3.12%, 3.13%, 3.14%, 3.15%, 3.16%, 3.17%, 3.18%, 3.19%, 3.2%, 3.21%, 3.22%, 3.23%, 3.24%, 3.25%, 3.26%, 3.27%, 3.28%, 3.29%, 3.3%, 3.31%, 3.32%, 3.33%, 3.34%, 3.35%, 3.36%, 3.37%, 3.38%, 3.39%, 3.4%, 3.41%, 3.42%, 3.43%, 3.44%, 3.45%, 3.46%, 3.47%, 3.48%, 3.49%, 3.5%, 3.51%, 3.52%, 3.53%, 3.54%, 3.55%, 3.56%, 3.57%, 3.58%, 3.59%, 3.6%, 3.61%, 3.62%, 3.63%, 3.64%, 3.65%, 3.66%, 3.67%, 3.68%, 3.69%, 3.7%, 3.71%, 3.72%, 3.73%, 3.74%, 3.75%, 3.76%, 3.77%, 3.78%, 3.79%, 3.8%, 3.81%, 3.82%, 3.83%, 3.84%, 3.85%, 3.86%, 3.87%, 3.88%, 3.89%, 3.9%, 3.91%, 3.92%, 3.93%, 3.94%, 3.95%, 3.96%, 3.97%, 3.98%, 3.99%, 4%, or more, wt/wt content as determined by dividing the weight of the terpene by the weight of the dried *cannabis* flower from which the sample derives.

Thus in some embodiments, systems, apparatuses, and methods as disclosed herein can define a sample's profile, such as a *cannabis* plant's terpene profile, in absolute or relative contents of 17 key terpenes: terpinolene, alpha phellandrene, beta ocimene, carene, limonene, gamma terpinene, alpha pinene, alpha terpinene, beta pinene, fenchol, camphene, alpha terpineol, alpha humulene, beta caryophyllene, linalool, caryophyllene oxide, and myrcene.

In some embodiments, the present invention will reference to a terpene profile which is dominated by a specific terpene. For example, a myrcene dominant terpene profile is used to refer to terpene profiles in which myrcene is the most abundant terpene in the terpene profile (i.e., myrcene relative or absolute content is greater than the content of any single one of the 16 other terpenes in the terpene profile).

While the terpene profile is meant to indicate that all 17 of the terpenes are assayed, one or more of the terpenes may not be present at detectable levels. The systems, apparatuses, and methods as disclosed herein can calculate terpene essential oil contents by adding the absolute contents by weight of the 17 terpenes from the terpene profile as defined above. The absolute terpene content is measured as w/w % value based on dry inflorescences. In some embodiments the terpene contents are measured via Gas Chromatography Flame Ionization Detection (GC-FID) (e.g., the chemical analyzer 110).

In other embodiments, systems, apparatuses, and methods as disclosed herein can define *cannabis*' expanded terpene profile in absolute or relative contents of 34 detectable terpenes: terpinolene, alpha phellandrene, trans-ocimine, carene, limonene, gamma terpinene, alpha pinene, alpha terpinene, beta pinene, fenchol, camphene, alpha terpineol, alpha humulene, beta caryophyllene, linalool, caryophyllene-oxide, myrcene, sabinene, cymene, cineole, cis-ocimene, (–)borneol, methyl-chavicol, nerol, neral, geraniol, gerinal, eugenol, geranyl-acetate, methyl-eugenol, cis-nerolidol, trans-nerolidol, pellitorine, phytol. While the expanded terpene profile is meant to indicate that all 34 of the terpenes are assayed, one or more of the terpenes may not be present at detectable levels. Expanded terpene essential oil contents are measured by adding the absolute contents by weight of the 34 terpenes from the terpene profile as defined above. The absolute terpene content is measured as w/w % value based on dry inflorescences. In some embodiments the terpene contents are measured via Gas Chromatography Flame Ionization Detection (GC-FID).

Classification Using Agglomerative Hierarchical Clustering (AHC) of Terpenes

In some embodiments, the present invention teaches classification of *cannabis* by subjecting terpene absolute or relative values to AHC analysis (e.g., employing aspects of the apparatus 120, such as the classifier 132). In some embodiments, the present invention teaches classification of *cannabis* by subjecting terpene relative values to AHC analysis.

AHC is a bottom-up classification approach in which a set of initially individual *cannabis* plants are placed into increasingly smaller hierarchical groups based on the similarity of observations provided to the analysis algorithm. Decomposition of data objects into a several levels of nested partitioning (i.e., a tree of clusters) is called a dendogram. A clustering of the data objects is obtained by cutting the dendogram at the desired level, where each connected component at that level forms a cluster.

Various techniques may be used to implement agglomerative hierarchical clustering. Typical algorithms for agglomerative hierarchical clustering include (a) average linkage clustering, (b) complete linkage clustering, (c) single linkage clustering, and (d) Ward's linkage clustering, among others. Guidance on implementing each of the linkage clustering techniques can be found in U.S. Pat. No. 8,402,027.

The tree of clusters that results from agglomerative hierarchical clustering can be pruned at any desired level, which may be determined based on the desired level of distinction between *cannabis* groups. In some embodiments, the AHC analysis is pruned after 1, 2, 3, 4, 5, 6, 7, 8, 9, 10, 11, 12, 13, 14, or 15 levels.

In some embodiments, the AHC analysis is pruned after 5%, 10%, 15%, 20%, 25%, 30%, 35%, 40%, 45%, 50%, 55%, 60%, 65%, 70%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% similarity between the members of the group.

A representative AHC analysis of *cannabis* samples based on can be seen in Example 4 of this disclosure. In some embodiments, the classification of *cannabis* samples using AHC analysis may not be stable, and can result in different classifications as determined by the terpene composition of the initial data set. That is, in some embodiments, the classification of a *cannabis* sample can be different, depending on the number, and type of *cannabis* which is included in the analysis.

Classification of *Cannabis* Using Fixed Absolute or Relative Terpene Level Analysis In some embodiments, the present invention teaches systems, apparatuses, and methods of classifying *cannabis* that are stable, and are independent from changes in the initial *cannabis* data set. In some embodiments, the present invention teaches the classification of *cannabis* samples based on the fixed classification of the absolute or relative terpene levels of the terpene profile, e.g., employing aspects of the apparatus 120 as described herein.

In some embodiments the terpene content of the *cannabis* of the present invention is described in relative terms as a % composition of the total terpene profile or expanded terpene profile. Thus for example a *cannabis* sample with 1.2% absolute terpinolene content and 1.2% myrcene content and no other terpenes would be said to have 50% terpinolene and 50% myrcene relative content. In some embodiments, the *cannabis* samples of the present invention have a relative content of any one of the 17 terpenes in the terpene profile (or 34 terpenes in the expanded terpene profile) that is about 0%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 79%, 79%, 80%, 81%, 82%, 83%, 84%, 85%, 86%, 87%, 88%, 89%, 90%, 91%, 92%, 93%, 94%, 95%, 96%, 97%, 98%, 99%, or 100%. Thus in some embodiments the relative content of any one of the terpenes is between 0% and 100%.

In some embodiments, the inventors of the present application have discovered that *cannabis* users can only accurately distinguish samples based on the highest 1, 2, 3, 4, or 5 terpenes accumulating in the sample. That is in some embodiments, "cannasseurs" are only able to distinguish *cannabis* samples based on the most prevalent terpenes. In some embodiments, the present invention teaches classification of terpenes based on the highest 3 accumulating terpenes as determined by relative terpene levels of the terpene profile or extended terpene profile.

A— Sequential Classification Method

In some embodiments, the present invention teaches systems, apparatuses, and methods as disclosed herein of classifying *cannabis* based on the absolute or relative *cannabis* terpene profiles. In some embodiments such a "sequential classification" scheme comprises the steps of:

1) Placing the *cannabis* sample into a primary category based on the highest accumulating terpene in the terpene profile;

2) Placing the *cannabis* samples into a secondary category based on the second-highest accumulating terpene in the terpene profile;

3) Placing the *cannabis* sample into a tertiary category based on the third-highest accumulating terpene in the terpene profile.

Thus in some embodiments, a *cannabis* sample with 70% myrcene, 20% limonene, and 10% carene will belong to the myrcene-limonene-carene group. In some embodiments, a second *cannabis* sample with 55% myrcene, 10% limonene, 9% carene, 7% fenchol, 7% beta caryophyllene, 7% gamma terpinene, and 5% alpha humulene would also be in the myrcene-limonene-carene group.

In some embodiments, the present invention teaches that the group name in a "sequential method" classification scheme is indicative of the relative accumulation of each terpene, with the highest accumulating terpene appearing first, the second highest accumulating terpene appearing second, etc. . . . .

In some embodiments, the disadvantage of the sequential classification method is that small variations in terpene contents can lead to samples with very similar physiological and organoleptic profiles to be in highly different categories. For example, under the sequential method of the present invention, a *cannabis* sample with 32% myrcene, 31% beta ocimene, 30% beta caryophyllene, and 7% linalool would be classified into a myrcene-beta ocimene-beta caryophyllene groups, while a highly similar sample containing 28% myrcene, 33% beta ocimene, and 32% beta caryophyllene, and 7% linalool would be classified into a completely different category of beta ocimene-beta caryophyllene-myrcene.

B— Grouping Classification Method

In other embodiments, the present invention teaches systems, apparatuses, and methods of classifying *cannabis* based on the relative *cannabis* terpene profiles. In some embodiments such a "grouping classification" scheme comprises the steps of:

1) Placing the *cannabis* sample into a classification group based on the highest accumulating group of terpenes in the terpene profile.

In some embodiments the grouping classification method of the present invention uses the 3 highest accumulating terpenes to classify *cannabis* samples. Thus, in some embodiments, a *cannabis* sample with 70% myrcene, 20% limonene, and 10% carene will belong to the carene-limonene-myrcene group. In some embodiments, a second *cannabis* samples with 60% limonene, 20% myrcene, and 20% carene will also belong the same carene-limonene-myrcene group.

In some embodiments, the grouping classification method classifies *cannabis* according to the terpenes which accumulate at highest levels, but does not distinguish between the differences in terpenes within the selected group. That is, in some embodiments, the order of the terpenes as presented in the group name is not indicative of the relative accumulation levels of each terpene.

In some embodiments, the order of the terpenes in the group name is determined by the order in which the terpenes pass through a GC-FID column. In other embodiments, the order of the terpenes in the group name is determined by a predetermined order based on other selected reasons. For example, in some embodiments, the order of the terpenes in the group name can reflect the strength of each terpene's aroma/flavor. In other embodiments, the order of the terpenes in the group name can reflect the strength of each terpene's known entourage or medical effects.

In some some embodiments, the order of the terpenes in the group classification method is as shown in Table 4.

In some embodiments, the disadvantage of the grouping classification method is that, while it is resistant to the sensitive re-categorization of samples demonstrated in the sequential method, it is not distinguish between large fluctuations in terpene profiles, so long as the top selected terpenes remain the same. That is in some embodiments, a *cannabis* sample with 70% myrcene, 20% limonene, and 10% carene will belong to the carene-limonene-myrcene group, while a second sample with potentially different organoleptic and physiological effects with 60% limonene, 20% myrcene, and 20% carene will also belong the same carene-limonene-myrcene group.

In some embodiments, the present invention addresses the shortfalls of both the sequential and group methods by utilizing the primary ethnobotanical method of classifying *cannabis* described below.

C— Primary Ethnobotanical Classification Method

In some embodiments, the present invention teaches systems, apparatuses, and methods a of classifying *cannabis* based on the relative *cannabis* terpene profiles. In some embodiments, this primary ethnobotanical method reflects the interaction between the *cannabis* samples and man, and encompasses both "effect" and "organoleptics." In some embodiments, primary ethnobotanical method classifies *cannabis* samples based on the primary terpene, and only distinguishes the sample into sub categories if the secondary, or tertiary terpenes are present at a sufficient level to significantly modify the aroma and/or physiological effects of the primary terpene.

Thus in some embodiments the primary ethnobotanical classification scheme comprises the steps of:

1) Determining the relative content level of the highest (primary) accumulating terpene of the *cannabis* sample (e.g., using the chemical analyzer 110). This primary terpene is associated a pre-determined "contribution factor".

2) Determining the relative content level of the second highest (secondary) accumulating terpene in the *cannabis* sample, and dividing it by the relative content level of the primary terpene. This number is the "secondary modulating factor."

3) Optionally, further determining the relative content level of the third highest (tertiary) accumulating terpene in the *cannabis* sample, and dividing it by the relative content level of the primary terpene. This number is the "tertiary modulating factor."

4) Wherein the classification group of said *cannabis* sample is the primary terpene (e.g., as determined by the classifier 132), and a secondary and tertiary terpene if each of the secondary and tertiary modulating factors are greater than or equal to the pre-assigned "contribution factor" for the primary terpene.

In some embodiments, the "contribution factor" for all terpenes is 50%. In other embodiments, the contribution factors can be modified based on experimental data showing stronger or weaker effects for various primary terpenes. In some embodiments the terpene contribution factors can be adjusted based on consumer studies or feedback.

In some embodiments, the order of the terpenes in the group name of samples classified by the primary ethnobotanical method is determined by the order in which the terpenes pass through a GC-FID column, such as of the chemical analyzer 110. In other embodiments, the order of the terpenes in the primary ethnobotanical method name is determined by a predetermined order based on other selected reasons. For example, in some embodiments, the order of the terpenes in the primary ethnobotanical method name can reflect the strength of each terpene's aroma/flavor. In other embodiments, the order of the terpenes in the group name can reflect the strength of each terpene's known entourage or medical effects.

In some some embodiments, the order of the terpenes in the primary ethnobotanical method classification method is as shown in Table 4.

Thus in an example classification using the "primary ethnobotanical method," a *cannabis* sample with 48% myrcene, 27% carene, and 25% limonene, the primary terpene is myrcene, the secondary terpene is carene, and the tertiary terpene is limonene. In this example embodiment, the contribution factor for myrcene is 50%, and the calculated secondary modulating factor for carene is 56.25% (27% carene divided by 48% myrcene, multiplied by 100), and the calculated tertiary modulating factor for limonene is 52.08% (25% limonene divided by 48% myrcene, multiplied by 100). In this example embodiment the secondary and tertiary factors are equal to, or greater than the primary terpene's contribution factor of 50%. As such, the example *cannabis* sample would be classified by the classifier 132 into the carene-limonene-myrcene group.

In another example classification using the "primary ethnobotanical method," a *cannabis* sample with 67% myrcene, 25% limonene, and 8% fenchol would have myrcene as the primary terpene, limonene as the secondary terpene, and fenchol as the tertiary terpene. In this example embodiment, the contribution factor for myrcene is still 50%, and the calculated secondary modulating factor for limonene is 37.3% (25% limonene divided by 67% myrcene, multiplied by 100), and the calculated tertiary modulating factor for fenchol is 11.9% (8% fenchol divided by 67% myrcene, multiplied by 100). In this example embodiment, neither the secondary, nor tertiary factors are equal to, or greater than the primary terpene's contribution factor of 50%. As such, the example *cannabis* sample would be classified by the classifier 132 into a myrcene group, without inclusion of the secondary or tertiary terpenes.

In some embodiments, the pre-set category grouping order of the primary ethnobotanical method prevents very small fluctuations in the relative terpene content of a sample from creating artificially distinct groups. For example, under the primary ethnobotanical method of the present invention, a *cannabis* sample with 31% myrcene, 30% beta ocimene, 30% beta caryophyllene, and 9% linalool would be classified by the classifier 132 into the same group as a *cannabis* sample with 28% myrcene, 33% beta ocimene, and 32% beta caryophyllene, and 7% linalool (the beta ocimene-beta caryophyllene-myrcene group).

In some embodiments, the primary ethnobotanical method of the present invention can distinguish between *cannabis* samples with the same highest accumulating terpene group, with large shifts in their relative levels that would produce different organoleptic and physiological effects. For example, in another example classification using the "primary ethnobotanical method," a *cannabis* sample with 67% myrcene, 25% limonene, and 8% fenchol would be classified by the classifier 132 into a myrcene group, while a 40% myrcene, 25% limonene, and 35% fenchol sample would be classified into a limonene-fenchol-myrcene group.

In some embodiments the determining steps of the classification schemes of the present invention can describe the actual measuring and recording of terpene or cannabinoid absolute or relative values. In other embodiments, the determining steps of the classification schemes of the present invention can simply involve the use of pre-calculated values for the absolute or relative values of the present invention. Thus in some embodiments, the determining steps can be considered to be part of the subsequent calculations steps if the values are already known to the person computer, or other object classifying the *cannabis* samples.

D— Comparison of Selected Classification Methods of the Present Invention

Table 3 below compares selected classification methods of the present invention, each of which can be carried out by the system 100 as described herein. In some embodiments, the "primary ethnobotanical" method of the present invention avoids the over-sensitivity of the serial method, while also being more representative than the grouping method which does not account for large disparities in the levels of terpenes among the highest accumulating terpenes. The table below shows example groupings limited to 3 terpenes. Persons having skill in the art will recognize that the methods of the present invention can be expanded to include 4, 5, or more terpenes.

TABLE 3

Grouping Method Comparison

| | Cannabis Sample | Serial Method | Grouping Method | Primary Ethnobotanical Method | Comments |
|---|---|---|---|---|---|
| 1 | 67% myrcene, 25% limonene, and 8% fenchol | myrcene-limonene-fenchol | limonene-fenchol-myrcene | myrcene | Only the primary ethnobotanical classification method distinguishes between samples with highly dominant terpenes (1) vs. terpenes in relatively equal amounts (2). |
| 2 | 40% myrcene, 35% limonene, and 25% fenchol | myrcene-limonene-fenchol | limonene-fenchol-myrcene | limonene-fenchol-myrcene | |
| 3 | 31% myrcene, 30.5% beta ocimene, 29.5% beta caryophyllene and 9% linalool | myrcene-beta ocimine-beta caryophyllene | beta ocimene-beta caryophylle-myrcene | beta ocimene-beta caryophylle-myrcene | The serial method is overly sensitive, and separates samples (3) and (4) based on very minor differences in their relative terpene levels. |
| 4 | 28% myrcene, 33% beta ocimene, and 32% beta caryophyllene, and myrcene 7% linalool | beta ocimene-beta caryophyllene-myrcene | beta ocimene-beta caryophylle- | beta ocimene-beta caryophylle-myrcene | |

E— Letter Code for Terpene Profiles

In some embodiments, the present invention teaches the use of alphanumeric sequences, including single letter codes, to represent the most prevalent terpenes found in *cannabis* plants. Thus, in some embodiments, the primary ethnobotanical classification method can be described in a string of letters according to the code designations presented in Table 4. In some embodiments, Table 4 also includes the order in which the code designations should be presented for the classification schemes of the present invention.

In some embodiments, persons having skill in the art will recognize that the classification method of the present invention can be used with a terpene different from the one presented in Table 4. For example, in some embodiments, the order can be based on known consumer preferences, or for any perceived aesthetics of the coding system.

TABLE 4

Example Code Designations for Terpenes

| Order | Abbrev. | Terpene |
|---|---|---|
| 1 | T | terpinolene |
| 2 | α | alpha phellandrene |
| 3 | O | trans-ocimine |
| 4 | χ | carene |
| 5 | L | limonene |
| 6 | γ | gamma terpinene |
| 7 | P | alpha pinene |
| 8 | τ | alpha terpinene |
| 9 | P | beta pinene |
| 10 | F | fenchol |
| 11 | D | camphene |
| 12 | I | alpha terpineol |
| 13 | H | alpha humulene |
| 14 | C | beta caryophyllene |
| 15 | U | linalool |
| 16 | ρ | caryophyllene-oxide |
| 17 | M | myrcene |
| 18 | S | sabinene |
| 19 | Y | cymene |
| 20 | ε | cineole |
| 21 | O | cis-ocimene |
| 22 | B | (-)borneol |
| 23 | V | methyl-chavicol |
| 24 | R | nerol |
| 25 | R | neral |
| 26 | G | geraniol |
| 27 | G | gerinal |
| 28 | E | eugenol |
| 29 | ψ | geranyl-acetate |
| 30 | υ | methyl-eugenol |
| 31 | N | cis-nerolidol |
| 32 | N | trans-nerolidol |
| 33 | λ | pellitorine |
| 34 | ω | phytol |

Thus for example, in some embodiments, primary ethnobotanical group classifications for limonene-fenchol-myrcene can be represented as LFM, L F M, or L-F-M. Persons having skill in the art will recognize that the code designations of Table 4, represent but one example of letter code designations that would be compatible with the present invention. In other embodiments, terpenes may be represented by any characters, colors, shapes, bar codes, etc.

In some embodiments the present invention teaches that code designations can be shared between one or more terpenes. In some embodiments, the use of the same designation for more than one terpene can be indicative of the chemical, organoleptic, or physiological effect similarities of the terpenes.

Classification Based on Cannabinoid Profiles

In some embodiments, the present invention also teaches systems, apparatuses, and methods of classifying *cannabis* based on the cannabinoid profiles of *cannabis* samples.

The present disclosure describes the vast array of at least 85 cannabinoids that have been detected in the *cannabis* plant. In some embodiments the most prevalent of these cannabinoids include THC, CBD, CBC, CBN, CBG, THCv, and CBDv.

Thus in some embodiments, the *cannabis* classification scheme of the present invention is based on the content of the highest 1, 2, 3, 4, 5, 6, 7, 8, 9, or 10 accumulating cannabinoids. In other some embodiments, the highest 3 accumulating cannabinoids.

In some embodiments, the present invention teaches that absolute cannabinoid levels in *cannabis* samples can vary based on environmental effects. Thus in some embodiments, the present invention teaches the classification of *cannabis* samples based on relative levels of cannabinoids.

In some embodiments, the present invention teaches the quantification of cannabinoids by high performance liquid chromatography (HPLC) or gas chromatography flame ionization detection (GC-FID) techniques, such as by the chemical analyzer 110. Example quantifications of cannabinoids can be seen in Example 9 of the disclosure. In some embodiments, cannabinoids are referred to by their absolute wt/wt % content values which are obtain by calculating the weight of the cannabinoid by the weight of the sample.

In some embodiments, the present invention teaches the classification of *cannabis* samples (e.g., by the classifier 132) by using a number to indicate the chemotype (i.e. 1, 2, 3, 4, etc.), followed by a letter to indicate the second most prevalent cannabinoid. Thus in some embodiments, the present invention teaches that the most prevalent cannabinoid is implicit in the chemotype designation, and the letter indicated the second minor cannabinoid that had the potential to modulate the effects of the major one.

In some embodiments, alphanumeric sequences, including single letter codes, were assigned to the most prevalent cannabinoids (e.g., by the sequence generator 140) found in *cannabis* plants in order to simplify the classification designations. In some embodiments, the cannabinoid-letter codes were: THCA=T, CBDA=D, CBCA=C, CBGA=G, THCVA=V, CBDVA=W, and CBGVA=Z.

Thus in some embodiments, example *cannabis* classifications using the methods of the present invention include:

1D=THCA>>CBDA>other cannabinoids
1G=THCA>CBGA>other cannabinoids
1V=THCA>THCVA>other cannabinoids
2T=CBDA>THCA>other cannabinoids
2D=THCA>CBDA>other cannabinoids
3T=CBDA>>THCA>other cannabinoids
3G=CBDA>CBGA>other cannabinoids
4T=CBGA>>THCA>other cannabinoids In some embodiments, the present invention provides a cannabinoid classification system that provides the most critical information to the user. For instance, under the traditional system a "2" designation (chemotype II) would imply the presence of both THCA and CBDA, but would not necessarily indicate the relative levels of each cannabinoid. That is the traditional classification would not distinguish between an 8% THCA, 4% CBDA sample, and a 8% CBDA, 4% THCA sample.

In some embodiments, the present cannabinoids classification system provides additional information regarding the ratio of THCA:CBDA ratio via "T" or "D" designations such that a 1:2 THCA:CBDA ratio sample would be 2T and a 2:1 THCA:CBDA ratio sample would be designated as 2D. Likewise, a 2T designation suggests closer amounts of THCA and CBDA while a 3T suggests only trace amounts of THCA.

In some embodiments, the present invention teaches new chemotype numbering. For example In some embodiments chemotype 6 represents a *cannabis* sample with a $B_T/B_T$ genotype with at least one copy of the $A_{pr}$ allele such that THCVA accumulates. In some embodiments chemotype 7 represents a *cannabis* sample with a $B_T/B_D$ genotype with at least one copy of the $A_p r$ allele such that THCVA and CBDVA accumulate. In some embodiments, chemotype 8 represents a *cannabis* sample with accumulating dominant levels of CBCA. In other embodiments, the present invention teaches the use of additional chemotype numberings as necessary.

*Cannabis* Classification Based on Both Cannabinoids and Terpenes

In some embodiments, the present invention also teaches an improved nomenclature system for describing the present classification groups of *cannabis* cultivars, conveying recognizable information pertinent to cultivators, dispensary managers, and patients. In some embodiments the improved classification and nomenclature of the present invention includes information related to the expected aroma and flavor of the *cannabis* group. In some embodiments the improved classification and nomenclature of the present invention includes information related to the expected physiological entourage effects of the *cannabis* group.

A— Letter Codes Indicating *Cannabis* Classification

In some embodiments, the present invention teaches systems, apparatuses, and methods for the classification of *cannabis* based on both its cannabinoid and terpene profiles. Thus in some embodiments, the classification of a *cannabis* sample can be represented by an alphanumeric string of letters or numbers representing the cannabinoid classification followed by a second string of letters or numbers representing the terpene classification. In other embodiments, the classification of a *cannabis* sample can be represented by a string of letters or numbers representing the terpene classification (e.g., a first subsequence) followed by a second string of letters or numbers (e.g., a second subsequence) representing the cannabinoid classification.

Below are some example *cannabis* group classification names based on the cannabinoid and primary ethnobotanical terpene classification methods of the present invention. In some embodiments, an "X" character or other spacer can be included where the terpene classification occupies less than all 3 characters.

3T LCM or LCM 3T=Code used for a sample with CBDA as the primary cannabinoid, with trace amounts of THCA as the secondary cannabinoid. This sample accumulates limonene, beta caryophyllene, and myrcene. The physiological and organoleptic effects of this sample will likely be a combination of the effects of all three terpenes.

1D MXX or MXX 1D=Code used for a sample with THCA as the primary cannabinoid with trace amounts of CBDA as the secondary cannabinoid. This sample contains a myrcene-dominant terpene profile, with no other terpene reaching at least 50% of the relative levels of myrcene in the sample. The physiological and organoleptics effects of this sample will likely be dominated by myrcene.

In some embodiments there is no space between the first subsequence and the second subsequence. In other embodiments there is a space between the first subsequence and the second subsequence.

A person having skill in the art will recognize that the *cannabis* classification codes of the present invention can be arranged in convenient ways to improve visibility or understanding of the intended audience. In some embodiments, the present invention teaches placing a space, a dash, a period, and/or another distinguishable character between the 2-letter code for the cannabinoids and the 3-letter code for the terpenes. In other embodiments no separating characters are added between the 5 characters.

B. Use of Subscripts and Superscripts

In some embodiments, the present invention teaches the use of subscripts or superscripts in the *cannabis* classification codes/alphanumeric sequences. In some embodiments these subscripts and/or superscripts can indicate additional information. In some embodiments, subscripts and/or superscripts can be used to indicate the relative content of each terpene or cannabinoid in a sample.

$3_{12}T_{0.5} L_{33}C_{33}M_{33}$=This code is used for a sample with CBDA as the primary cannabinoid, with trace amounts of THCA as the secondary cannabinoid. This sample accumulates limonene, beta caryophyllene, and myrcene. The subscripts indicate that the sample has 12% absolute CBDA content and 0.5% absolute THCA content. The subscripts further indicate that there is an equal amount of each of limonene, beta caryophyllene, and myrcene (33% each).

Persons having skill in the art will recognize the various other uses for subscripts and superscripts including the indication of low/medium/high levels of absolute cannabinoids and/or terpenes.

C. Indications of Terpene to Cannabinoid Ratio

In some embodiments, the present invention teaches that the pharmacology of *cannabis* is largely driven by the cannabinoids, while the terpenes provide the modulating entourage effects that are "superimposed" upon the more dominant effects from the cannabinoids. In some embodiments, the present invention also teaches that the terpenes provide the aroma and flavor properties of the *cannabis* sample. This suggests that at the cannabinoid content increases relative to the terpene content, the pharmacology is mainly driven by the cannabinoids and the terpenes play a smaller role.

Thus, a cultivar with 1% absolute total terpene content and 10% absolute total cannabinoid content may provide a different effect than one with the same relative chemotype profile but accumulating only 0.5% absolute total terpene content and 30% absolute cannabinoid content.

In some embodiments, the present invention teaches that there is a critical ratio of absolute cannabinoid levels to total absolute terpene contents after which the physiological modulating effects of terpenes become irrelevant when compared against the overwhelming effect of the cannabinoids.

Thus in some embodiments, the present invention teaches that once the ratio of absolute cannabinoid contents to absolute terpene contents meets or exceeds the critical ratio, the terpene portion of the *cannabis* categorization becomes unimportant and is designated as an "XXX" alphanumeric sequence.)

In some embodiments, the present invention teaches that the critical ratio of absolute cannabinoid levels to total absolute terpene contents is 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99, or 100. In other embodiments, the present invention teaches that the critical ratio of absolute cannabinoid levels to total absolute terpene contents is 60. In yet other embodiments, the present invention teaches that the critical ratio of absolute cannabinoid levels to total absolute terpene contents can be adjusted based on consumer trials or user feedback.

An example code designation for a variety exceeding the critical ratio is shown below.

1D XXX=This is an example code used for a sample with THCA as the primary cannabinoid with trace amounts of CBDA as the secondary cannabinoid, wherein the critical ratio of absolute cannabinoid levels to total absolute terpene contents as been exceed. Recreational consumers or patients are unlikely to nice any terpene modulatory effects from this sample.

C. Exemplary Uses of the 5-Digit Code of the Present Invention

In some embodiments, the resulting 5 letter/digit designation/alphanumeric sequence of the present invention can be used as a Price-Look up (PLU) code that could be used with point of sale and PLU systems that are currently used in retail markets. Thus for example, in some embodiments, the 3TLCM code described above for the *cannabis* sample with CBDA as the primary cannabinoid with trace amounts of THCA as the secondary cannabinoid with limonene, beta caryophyllene, and myrcene could be used with a PLU system.

In some embodiments the code could be used to track sales of particular types of *cannabis*, or to pull up additional medical or recreational information regarding the type of *cannabis* that was purchased.

A non-limiting list of the envisioned uses for the classification methods and nomenclature schemes of the present invention are listed below:

Consistent Consumer Experience—

In some embodiments, a consumer will be able to use the classification and nomenclature methods of the present invention to readily identify his or her preferred *cannabis* type. This will allow consumers to purchase *cannabis* of the same category from the same or different sources (as identified by the code of the sample) while still obtaining experiencing similar organoleptic and physiological effects. This will also allow for product substitutions when a particular cultivar is not in stock.

Market Research—

In some embodiments, the methods of the present invention will allow individuals to track the most popular combinations of cannabinoids and terpenes via point of sale reports based on the use of PLU codes. This will allow producers to identify areas of consumer interest and produce additional *cannabis* lines with similar properties.

Medical Consistency—

In some embodiments, the methods of the present invention will allow doctors to prescribe *cannabis* based on expected effects. Doctors will likely get feedback from patients regarding which cannabinoids/terpene combinations yielded the best results, and will be able to apply that knowledge to future prescriptions. As research results become available, each *cannabis* category will become associated with a particular medical benefit. A list of expected medical benefits for each cannabinoid and terpene combination is included in this application.

Research Consistency—

In some embodiments, the methods of the present invention will allow laboratories to obtain similar *cannabis* samples associated with experimental results. Thus laboratories will be able to continually source equivalent samples for long term projects from the same different sources. In some embodiments, this will also allow laboratories to replicate research performed by other laboratories without having to replicate their source of *cannabis* material.

Inventory Tracking—

In some embodiments, the methods of the present invention will allow dispensaries and producers to track production and sales of different types of *cannabis*, which will increase the security of seed to sale verification.

Price Tracking/Matching—

In some embodiments, the methods of the present invention will allow dispensaries to compare prices for similar products across different varieties. This will also encourage consumers to pay premium prices for premium product, or get discounts on less-desirable product (with the assurance that they are getting exactly what they paid for).

Thus in some embodiments, the present invention teaches methods of classifying, identifying, selling, managing, prescribing, and marketing *cannabis* based on objective scientific basis independent of the traditional "name" or "species" designation, in order to provided consistency, can be measured objectively, and dictate the organoleptic and therapeutic experience of the patient. Persons having skill in the art will recognize the almost limitless applications for a stable and representative classification system and nomenclature for *cannabis*. The examples listed above are only presented as example embodiments, but should not be construed as a limiting or exhaustive list.

In some embodiments, the present invention teaches classification methods which are based on the contributions from both terpene and cannabinoid contents. In other embodiments, the present invention teaches classification methods that avoid the use of sensitive clustering algorithms, and maintain relatively stable categories. In yet other embodiments, the present invention teaches classification methods which produce intuitive category clusters that "cannasseurs" could recognize by their organoleptic properties. Correlation between objective and subjective assays would further verify the utility of this system.

Aroma/Flavor and Entourage *Cannabis* Reports

In some embodiments, the present invention teaches that terpene profiles contribute to the organoleptic properties, and physiological entourage properties of a *cannabis* sample. While some analytical laboratories have begun to analyze the terpene and cannabinoid contents of cultivars, current reporting systems are simply "data dumps" that present raw data regarding the absolute or relative contents of terpenes and cannabinoids, but make no attempt to correlate it to the properties they supposedly dictate. Moreover, most analytical laboratories still employ incorrect detection techniques for terpenes, and none provide reports on the complete terpene profile or extended terpene profile as taught in the present invention.

In some cases, analytical *cannabis* reports have included references to certain published discoveries describing, for example, the expected binding properties of a terpene to a receptor. This information however, is not quantitatively tied to the analytical results from a specific cultivar, nor is an attempt made to present contributions from different analytes to the overall properties.

For instance, a cultivar that is limonene dominant may be "citrusy", but myrcene, pinene, and camphene are all described as "woody," "terpy," and "herbaceous" and these minor components may sum to an "herbal" aroma that dominates the "citrusy" component. Similarly, while a cultivar that is high in myrcene may be a good analgesic, one with moderate amounts of myrcene, linalool, caryophyllene, and alpha phellandrene may have even stronger analgesic properties due to the contributions from each of these components to the anti-inflammatory and analgesic properties.

Thus in some embodiments, the present invention teaches an improved reporting system that not only presents raw data from analytical assays, but also transforms that raw data into information that connoisseurs, patients, and physicians could find useful. In some embodiments, the present invention transforms raw cannabinoid and terpene data into organoleptic properties and provides information that can be useful for cultivar identification and patient preferences. In other embodiments, the present invention transforms raw cannabinoid and terpene data suggested entourage effects and provides information that can be useful for therapeutic indications.

A— Aroma and Flavor Reports

In some embodiments, the present invention teaches systems, apparatuses, and methods of preparing aroma and flavor reports based on a *cannabis* sample's terpene profile. In some embodiments, the present invention teaches the following steps for creating an aroma report (e.g., using aspects of the system/kit 100):

1) Determining the absolute or relative terpene contents of the terpenes in the terpene profile or extended terpene profile of a *cannabis* sample.

2) Multiplying the absolute or relative content value of each of the terpenes against that terpene's aroma descriptor loading factors and recording the resulting number.

3) Adding each of the values that have been recorded under each aroma category and recording the final value.

4) Optionally, the values for each aroma category may be compiled into a visual aid that can be presented to consumers, or other target audience.

Thus in some embodiments the formula for calculating a single terpene's contribution to one of the aroma categories is:

$$[T_{C1}] \times [T_{LF1}] = \text{Aroma 1 Value for Terpene 1}$$

where $T_{C1}$ is the relative or absolute content of terpene 1, $T_{LF1}$ is the terpene loading factor for that terpene and that aroma. In some embodiments, the contributions of each terpene can then be added for each of the aroma categories to generate to final aroma values for the *cannabis* sample.

In some embodiments, the present invention teaches the following steps towards creating a flavor report:

1) Determining the absolute or relative terpene contents of the terpenes in the terpene profile or extended terpene profile.

2) Multiplying the absolute or relative content value of each of the terpenes against that terpene's flavor descriptor loading factors and recording the resulting number.

3) Adding each of the values that have been recorded under each flavor category and recording the final value.

4) Optionally, the values for each flavor category may be compiled into a visual aid that can be presented to consumers, or other target audience.

Thus in some embodiments the formula for calculating a single terpene's contribution to one of the flavor categories is:

$$[T_{C1}] \times [T_{LF1}] = \text{Flavor 1 Value for Terpene 1}$$

where $T_{C1}$ is the relative or absolute content of terpene 1, $T_{LF1}$ is the terpene loading factor for that terpene and that flavor. In some embodiments, the contributions of each terpene can then be added for each of the flavor categories to generate to final aroma values for the *cannabis* sample.

In some embodiments, the flavor and/or aroma descriptor loading factors for each terpene can be 0.05, 0.06, 0.07, 0.08, 0.09, 0.1, 0.11, 0.12, 0.13, 0.14, 0.15, 0.16, 0.17, 0.18, 0.19, 0.2, 0.21, 0.22, 0.23, 0.24, 0.25, 0.26, 0.27, 0.28, 0.29, 0.3, 0.31, 0.32, 0.33, 0.34, 0.35, 0.36, 0.37, 0.38, 0.39, 0.4, 0.41, 0.42, 0.43, 0.44, 0.45, 0.46, 0.47, 0.48, 0.49, 0.5, 0.51, 0.52, 0.53, 0.54, 0.55, 0.56, 0.57, 0.58, 0.59, 0.6, 0.61, 0.62, 0.63, 0.64, 0.65, 0.66, 0.67, 0.68, 0.69, 0.7, 0.71, 0.72, 0.73, 0.74, 0.75, 0.76, 0.77, 0.78, 0.79, 0.8, 0.81, 0.82, 0.83, 0.84, 0.85, 0.86, 0.87, 0.88, 0.89, 0.9, 0.91, 0.92, 0.93, 0.94, 0.95, 0.96, 0.97, 0.98, 0.99, 1, 1.01, 1.02, 1.03, 1.04, 1.05, 1.06, 1.07, 1.08, 1.09, 1.1, 1.11, 1.12, 1.13, 1.14, 1.15, 1.16, 1.17, 1.18, 1.19, 1.2, 1.21, 1.22, 1.23, 1.24, 1.25, 1.26, 1.27, 1.28, 1.29, 1.3, 1.31, 1.32, 1.33, 1.34, 1.35, 1.36, 1.37, 1.38, 1.39, 1.4, 1.41, 1.42, 1.43, 1.44, 1.45, 1.46, 1.47, 1.48, 1.49, 1.5, 1.51, 1.52, 1.53, 1.54, 1.55, 1.56, 1.57, 1.58, 1.59, 1.6, 1.61, 1.62, 1.63, 1.64, 1.65, 1.66, 1.67, 1.68, 1.69, 1.7, 1.71, 1.72, 1.73, 1.74, 1.75, 1.76, 1.77, 1.78, 1.79, 1.8, 1.81, 1.82, 1.83, 1.84, 1.85, 1.86, 1.87, 1.88, 1.89, 1.9, 1.91, 1.92, 1.93, 1.94, 1.95, 1.96, 1.97, 1.98, 1.99, 2, 2.01, 2.02, 2.03, 2.04, 2.05, 2.06, 2.07, 2.08, 2.09, 2.1, 2.11, 2.12, 2.13, 2.14, 2.15, 2.16, 2.17, 2.18, 2.19, 2.2, 2.21, 2.22, 2.23, 2.24, 2.25, 2.26, 2.27, 2.28, 2.29, 2.3, 2.31, 2.32, 2.33, 2.34, 2.35, 2.36, 2.37, 2.38, 2.39, 2.4, 2.41, 2.42, 2.43, 2.44, 2.45, 2.46, 2.47, 2.48, 2.49, 2.5, 2.51, 2.52, 2.53, 2.54, 2.55, 2.56, 2.57, 2.58, 2.59, 2.6, 2.61, 2.62, 2.63, 2.64, 2.65, 2.66, 2.67, 2.68, 2.69, 2.7, 2.71, 2.72, 2.73, 2.74, 2.75, 2.76, 2.77, 2.78, 2.79, 2.8, 2.81, 2.82, 2.83, 2.84, 2.85, 2.86, 2.87, 2.88, 2.89, 2.9, 2.91, 2.92, 2.93, 2.94, 2.95, 2.96, 2.97, 2.98, 2.99, 3.0, or more.

In some embodiments, the flavor and aroma descriptor loading factors are obtained by surveying literature and using descriptors given by "The Good Scents Company" (www.thegoodscentscompany.com) for each of the terpenes. In some embodiments the flavor and aroma descriptor loading factors are obtained by similar services to The Good Scents Company." In some embodiments, the reports surveyed in the creation of the loading factors differentiated between aroma and flavor.

In some embodiments, aroma and flavor categories comprise, but are not limited to: sweet, fruity, citrusy, floral, herbal, piney, earthy, camphor, spicy, tropical. In other embodiments the aroma categories of the present invention comprise the aromas listed in the 1983 version of the Fragrance Chart. In some embodiments, the aroma categories of the present invention comprise, but are not limited to: floral, soft floral, floral oriental, soft oriental, oriental, woody oriental, mossy woods, dry woods, citrus, green, and water.

In other embodiments the aroma categories of the present invention comprise the aromas listed in the 2008 version of the Fragrance Chart, including: loral, soft floral, floral oriental, soft oriental, oriental, woody oriental, woods, mossy woods, dry woods, citrus, fruity, green, and water (Edwards, Michael (2008), *Fragrances of the world* 2008, Michael Edwards & Co, ISBN 978-0-9756097-3-6).

In other embodiments the aroma categories of the present invention comprise the aromas listed in the 2010 version of the Fragrance Chart, including: loral, soft floral, floral oriental, soft oriental, oriental, woody oriental, woods, mossy woods, dry woods, aromatic, citrus, fruity, green, and water. In other embodiments, the aroma and flavor categories will comprise the complete list of aromas in the flavor charts. In other embodiments, partial lists tailored to the aromas generally produced by *cannabis* are used.

In some embodiments, the loading factors for each flavor category are created by converting qualitative descriptions found in the literature into quantitative flavor and aroma values. For example, in some embodiments, if the language used suggested a dominant characteristic of a terpene, then a higher value was used, and if it suggested "nuances" or "undertones" then smaller values were used.

In some embodiments, the descriptor loading factors of the present invention for aroma and flavor are those shown in Table 5 and 6.

TABLE 5

Example Aroma Descriptor Loading Factors
Aroma Descriptor Loading Factors

| # | Analyte | Sweet | Fruity | Citrusy | Floral | Herbal | Piney | Earthy | Camphor | Spicey | Tropical |
|---|---|---|---|---|---|---|---|---|---|---|---|
| 1 | myrcene | | | | 0.25 | 1 | 0.5 | 0.25 | | | |
| 2 | caryophyllene oxide | 0.25 | | | | | | 0.5 | | 0.5 | |
| 3 | linalool | 1 | 0.5 | 1 | 1 | | | | | | 0.25 |
| 4 | b-caryophyllene | 0.5 | | | | | | 0.5 | 0.5 | 1 | |
| 5 | a-humilene | | | | | | | 0.5 | | | |
| 6 | a-terpineol | | | 0.5 | 1 | | 1 | 0.25 | | | |
| 7 | camphene | | | 0.25 | | | 0.5 | 0.25 | 1 | 0.25 | |
| 8 | fenchol | 0.25 | 0.25 | | | | 1 | 0.25 | 1 | | |
| 9 | b-pinene | | | | | | 1 | 0.5 | 1 | | |
| 10 | a-terpinene | | 0.25 | 1 | | | 0.5 | 0.5 | 0.25 | 0.25 | |
| 11 | a-pinene | | | | | 0.25 | 1 | 0.5 | 1 | | |
| 12 | g-terpinene | 1 | 0.25 | 0.5 | | | 0.5 | 0.25 | | | 0.25 |
| 13 | limonene | 0.5 | 1 | 1 | | | | | | | 0.5 |
| 14 | carene | 1 | | 1 | | | | | | | |
| 15 | b-ocimene | 0.5 | | | 1 | 1 | | | | | 1.5 |
| 16 | a-phellandrene | | 1 | | 1 | | | 0.25 | | 0.25 | 0.5 |
| 17 | terpinolene | 1 | | 0.5 | | | 0.5 | 0.25 | 0.5 | | |

TABLE 6

Example Flavor Descriptor Loading Factors

| # | Analyte | Sweet | Fruity | Citrusy | Floral | Herbal | Piney | Earthy | Camphor | Spicy | Tropical |
|---|---|---|---|---|---|---|---|---|---|---|---|
| 1 | myrcene | | 0.5 | 0.5 | | 1 | | 0.5 | | | |
| 2 | Caryophyllene oxide | | | | | | | | | 1 | |
| 3 | linalool | | 1 | 0.5 | 1 | | | 0.25 | | | 0.5 |
| 4 | b-caryophyllene | | | 0.25 | | | | 0.5 | 1 | 1 | |
| 5 | a-humulene | | | | | | | 1 | | | |
| 6 | a-terpineol | | | | 1 | | | | | | |
| 7 | camphene | | | 0.25 | | | | | 1 | 0.25 | |
| 8 | fenchol | | | 0.5 | | | | | | | |
| 9 | b-pinene | | | | | | 1 | | 0.5 | | |
| 10 | a-terpinene | | 0.5 | 0.5 | | | 1 | 0.25 | | 0.25 | |
| 11 | a-pinene | | 0.25 | | | 0.25 | 1 | 0.5 | 0.5 | 0.25 | |
| 12 | g-terpinene | | 1 | 1 | | | 1 | | | | |
| 13 | limonene | 1 | 0.5 | 1 | | | | | | | 0.5 |
| 14 | carene | | | 1 | | | | | | | |
| 15 | b-ocimene | | | | 1 | | | | | | 1.5 |
| 16 | a-phellandrene | | 0.5 | 0.5 | | | 1 | | | | 0.25 |
| 17 | terpinolene | | 0.5 | | 0.25 | 0.25 | 1 | 0.5 | | | |

In some embodiments the aroma and flavor loading factors can be modified to account for vapor pressures, volatility, experimental headspace data, and/or additional information related to human sensitivity (detectability) for each of the terpenes. In some embodiments, the present invention teaches methods of fine tuning the descriptor loading factors via patient or recreational user input. In some embodiments, the aroma and loading factors of the present invention include contributions from *cannabis* breeder previous knowledge and experience.

In some embodiments, the present invention teaches the presentation of aroma and flavor values in alternative formats tailored to the intended audience. Thus in some embodiments, the aroma and flavor values of the present invention can be displayed in charts, as representative images, as color schemes, descriptions, or other presentation methods known to those with skill in the art.

In some embodiments, the present invention teaches the presentation of aroma and flavor values in radar charts (also known as spider charts). In other embodiments, aroma and flavor values can be represented by images. For example, in some embodiments, each aroma and flavor category is associated with a stock image, which can be used to represent the expected organoleptic properties of the *cannabis* sample. In some embodiments, the aroma and flavor values of a sample are ranked, and the top 1, 2, 3, 4, 5, 6, 7, 8, 9, or 10 images are displayed on the report for fast recognition and association by the patient. In some embodiments only the top 2 images are displayed.

In some embodiments, dispensaries utilizing the presentation formats of the present invention will also have accompanying displays explaining how to interpret the results. Thus in some embodiments, dispensaries would explain the meaning of any color, picture, chart, or other presentation scheme used to represent the aroma and flavor values of the present invention.

A— Entourage Reports

In some embodiments, the present invention teaches systems, apparatuses, and methods of preparing entourage effect reports based on a *cannabis* sample's terpene and cannabinoid profile. In some embodiments, the present invention teaches the following steps for creating an entourage effect report (e.g., using aspects of the system/kit 100):

1) Determining the absolute terpene contents of the terpenes in the terpene profile or extended terpene profile of a *cannabis* sample.

2) Determining the absolute cannabinoid contents in of the *cannabis* sample of step 1.

3) Multiplying the absolute content value of each of the cannabinoids of the *cannabis* sample against each terpene-cannabinoid combination's synergy factor to produce a weighted entourage loading factors for each terpene.

4) Multiplying the absolute content value of each of the terpenes of the *cannabis* sample against that terpene's weighted entourage loading factors and recording the resulting number.

5) Adding each of the values that have been recorded under each entourage effect category and recording the final value.

6) Optionally, the values for each aroma category may be compiled into a visual aid that can be presented to consumers, or other target audience.

Thus in some embodiments the formula for calculating a single terpene's contribution to one of the entourage effects categories is:

$$[T_{C1}] \times [T_{WEF1}] = \text{Entourage Effect 1 Value for Terpene 1}$$

where $T_{C1}$ is the absolute content of terpene 1, $T_{WLF1}$ is the terpene weighted entourage factor for that terpene and that entourage effect. In some embodiments, the contributions of each terpene can then be added for each of the entourage effect categories to generate to final entourage effect values for the *cannabis* sample.

In some embodiments, the process for preparing entourage effect reports is similar to that of generating aroma and flavor reports, in that the absolute values of terpenes are multiplied by loading factors which transform chemical content values into expected effects on a user (whether organoleptic or physiological). In some embodiments however, the entourage reports include additional synergy factors to describe the entourage or synergistic effects between terpene and cannabinoid combinations. That is, the present invention teaches methods of quantifying the modulating effects that terpenes can have on the general physiological effects of cannabinoids, and vice versa.

In practical terms, this is done in some embodiments by increasing each terpene's base entourage loading factors, by the percent amount calculated by multiplying the absolute or relative values of each cannabinoid by each cannabinoid-terpene combination's synergy factor. An example formula for calculating a specific weighted entourage factor for a single terpene is shown below:

$$(([C_{C1}] \times [T_{SF1}] + 100) \times [T_{B1}]) = \text{Weighted Entourage Factor for Terpene1 and Cannabinoid1}$$

where $C_{C1}$ is a cannabinoid's absolute content, $T_{SF1}$ is a terpene synergy factor for a first terpene, and Tb1 is the terpene base entourage factor.

In some embodiments, the base entourage factors for each terpene and entourage effect can be 0.05, 0.06, 0.07, 0.08, 0.09, 0.1, 0.11, 0.12, 0.13, 0.14, 0.15, 0.16, 0.17, 0.18, 0.19, 0.2, 0.21, 0.22, 0.23, 0.24, 0.25, 0.26, 0.27, 0.28, 0.29, 0.3, 0.31, 0.32, 0.33, 0.34, 0.35, 0.36, 0.37, 0.38, 0.39, 0.4, 0.41, 0.42, 0.43, 0.44, 0.45, 0.46, 0.47, 0.48, 0.49, 0.5, 0.51, 0.52, 0.53, 0.54, 0.55, 0.56, 0.57, 0.58, 0.59, 0.6, 0.61, 0.62, 0.63, 0.64, 0.65, 0.66, 0.67, 0.68, 0.69, 0.7, 0.71, 0.72, 0.73, 0.74, 0.75, 0.76, 0.77, 0.78, 0.79, 0.8, 0.81, 0.82, 0.83, 0.84, 0.85, 0.86, 0.87, 0.88, 0.89, 0.9, 0.91, 0.92, 0.93, 0.94, 0.95, 0.96, 0.97, 0.98, 0.99, 1, 1.01, 1.02, 1.03, 1.04, 1.05, 1.06, 1.07, 1.08, 1.09, 1.1, 1.11, 1.12, 1.13, 1.14, 1.15, 1.16, 1.17, 1.18, 1.19, 1.2, 1.21, 1.22, 1.23, 1.24, 1.25, 1.26, 1.27, 1.28, 1.29, 1.3, 1.31, 1.32, 1.33, 1.34, 1.35, 1.36, 1.37, 1.38, 1.39, 1.4, 1.41, 1.42, 1.43, 1.44, 1.45, 1.46, 1.47, 1.48, 1.49, 1.5, 1.51, 1.52, 1.53, 1.54, 1.55, 1.56, 1.57, 1.58, 1.59, 1.6, 1.61, 1.62, 1.63, 1.64, 1.65, 1.66, 1.67, 1.68, 1.69, 1.7, 1.71, 1.72, 1.73, 1.74, 1.75, 1.76, 1.77, 1.78, 1.79, 1.8, 1.81, 1.82, 1.83, 1.84, 1.85, 1.86, 1.87, 1.88, 1.89, 1.9, 1.91, 1.92, 1.93, 1.94, 1.95, 1.96, 1.97, 1.98, 1.99, 2, 2.01, 2.02, 2.03, 2.04, 2.05, 2.06, 2.07, 2.08, 2.09, 2.1, 2.11, 2.12, 2.13, 2.14, 2.15, 2.16, 2.17, 2.18, 2.19, 2.2, 2.21, 2.22, 2.23, 2.24, 2.25, 2.26, 2.27, 2.28, 2.29, 2.3, 2.31, 2.32, 2.33, 2.34, 2.35, 2.36, 2.37, 2.38, 2.39, 2.4, 2.41, 2.42, 2.43, 2.44, 2.45, 2.46, 2.47, 2.48, 2.49, 2.5, 2.51, 2.52, 2.53, 2.54, 2.55, 2.56, 2.57, 2.58, 2.59, 2.6, 2.61, 2.62, 2.63, 2.64, 2.65, 2.66, 2.67, 2.68, 2.69, 2.7, 2.71, 2.72, 2.73, 2.74, 2.75, 2.76, 2.77, 2.78, 2.79, 2.8, 2.81, 2.82, 2.83, 2.84, 2.85, 2.86, 2.87, 2.88, 2.89, 2.9, 2.91, 2.92, 2.93, 2.94, 2.95, 2.96, 2.97, 2.98, 2.99, or 3.0.

In some embodiments, the base entourage factors of the present invention are shown in Table 7.

TABLE 7

Example Base Entourage Factors for Each Terpene

| | | Based Entourage Loading Factors | | | | | |
| --- | --- | --- | --- | --- | --- | --- | --- |
| # | Analyte | AChE Inh Focus | Stimulant Energy | Antidepressant Inspiration | Anxiolytic Calm | Analgesic Comfort | Sedative Relaxation |
| 1 | myrcene | | | | 0.25 | 0.5 | 1 |
| 2 | Caryophyllene oxide | | 1 | | | | |
| 3 | linalool | | | 0.5 | 1 | 0.25 | 0.5 |
| 4 | b-caryophyllene | | | | 0.5 | 1 | |
| 5 | a-humulene | | | | | 0.25 | |
| 6 | a-terpineol | 0.25 | 0.5 | | | | 0.25 |
| 7 | camphene | | | | | | |
| 8 | fenchol | | 0.5 | | | | |
| 9 | b-pinene | 1 | | 0.25 | | 0.25 | |
| 10 | a-terpinene | | | | | | |
| 11 | a-pinene | 1 | 0.25 | | | 0.25 | |
| 12 | g-terpinene | | | | | | |
| 13 | limonene | 0.25 | 1 | 1.5 | 0.5 | | |
| 14 | carene | | | | 0.5 | 0.25 | |
| 15 | b-ocimene | | | 0.5 | 1 | | |
| 16 | a-phellandrene | | | | | 0.25 | |
| 17 | terpinolene | | 1.5 | | 0.5 | | |

In some embodiments, the terpene synergy factors can be 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9, or 10.0 for each terpene/cannabinoid combination. In some embodiments, the terpene synergy factors for CBD are 3.0 for all terpenes. In some embodiments, the terpene synergy factors for THC are 3.0 for all terpenes.

In some embodiments, the terpene base entourage factors and terpene synergy factors are obtained by surveying literature for each of the terpenes and cannabinoids. In some embodiments, a non-limiting list of the reports surveyed in the creation of the loading factors is included in Table 8.

TABLE 8

Non-limiting Compilation of the Sources Used to Develop Terpene Base Entourage Factors and Terpene Synergy Factors

| Terpene | Effect | Article title | First Author | Journal ref |
|---|---|---|---|---|
| 1,8-cineole | AChE Inh<br>Increases cerebral blood flow<br>stimulant<br>antibioitc<br>anti-inflammatory<br>antinociceptive | Cannabis and Cannabis Extracts: Greater Than the Sum of Their Parts | McPartland | Journal of Cannabis Therapeutics (The Haworth Integrative Healing Press, an imprint of The Haworth Press, Inc.) Vol. 1, No. 3/4, 2001, pp. 103-132 |
| a-phellandrene | antinociceptive | Antinociceptive activity of the monoterpene a-phellandrene in rodents: possible mechanisms of action | Lima et al | J Pharm Pharmacol. 2012 Feb;64(2):283-92. doi: 10.1111/j.2042-7158.2011.01401.x. Epub 2011 Dec. 8 |
| a-pinene | anti-inflammatory<br>bronchodilator<br>stimulant<br>AChE inhibitor<br>antimicrobial | Biological activities of a-pinene and b-pinene enantiomers | Rivas da Silva, A.C. | Molecules, 2012, 17(6): 6305-16 |
| | analgesic | A Review on Anti-Inflammatory Activity of Monoterpenes | da Silveira e Sá, R.C. | Molecules 2013, 18: 1227-1254; doi:10.3390/molecules18011227 |
| a-terpineol | antiasthmatic | A Review on Anti-Inflammatory Activity of Monoterpenes | da Silveira e Sá, R.C. | Molecules 2013, 18: 1227-1254; doi:10.3390/molecules18011227 |
| | sedative<br>antibiotic<br>AChE inhibitor<br>(bradychardia,<br>hypotension<br>bronchoconstriction focus)<br>antioxidant<br>antimalarial | Cannabis and Cannabis Extracts: Greater Than the Sum of Their Parts | McPartland | Journal of Cannabis Therapeutics (The Haworth Integrative Healing Press, an imprint of The Haworth Press, Inc.) Vol. 1, No. 3/4, 2001, pp. 103-132 |
| | antimicrobial | Antimicrobial activity of the major components of the essential oil of Melaleuca alternifolia | Carson, C.F. | The Journal of applied bacteriology, 1995, 78(3): 264-9 |
| a-terpinene | antioxidant | Unusual Antioxidant Behavior of α- and γ-Terpinene in Protecting Methyl Linoleate, DNA, and Erythrocyte | Li, G.X. | Journal of Agricultural and Food Chemistry, 2009, 57(9): 3943-3948 |
| b-ocimene | anxiolytic<br>sedative | Identification of a Novel GABAA Receptor Channel Ligand Derived from Melissa officinalis and Lavandula angustifolia Essential Oils | Mahita | European Journal of Medicinal Plants 4(7): 810-818, 2014 |
| b-pinene | strong antimicrobial | Biological activities of a-pinene and b-pinene enantiomers | Rivas da Silva, A.C. | Molecules, 2012, 17(6): 6305-16 |
| | antidepressaant | Antidepressant activity of Litsea glaucescens essential oil: identification of β-pinene and linalool as active principles | Guzmán-Gutiérrez, S.L. | Journal of ethnopharmacology, 2012 Sep. 28; 143(2): 673-9 |
| | AChE inhibitor | The essential oil of Eucalyptus tereticornis, and its constituents α- and β-pinene, potentiate acetylcholine-induced contractions in isolated rat trachea | Lima, J.B.F. | Fitoterapia, 2010, 81(6): 649-55 |
| camphene | reduces plasma cholesterol and triglycerides | Camphene, a plant-derived monoterpene, reduces plasma cholesterol and triglycerides in hyperlipidemic rats indepedently of HMG-CoA reductase activity | Vallianou, I. | PLoS ONE, 2011, 6(11) e20516, doi:10.1371/journal.pone.0020516 |
| | antioxidant and free radical scavenger | Antinociceptive activity and redox profile of the monoterpenes (+)-Camphene, p-Cymene, and geranyl acetate in experimental models | Quintans-Junior, L. | ISRN Toxicology 2012. vol 2013, Article ID 459530 |
| carene | CNS depressant, anti-inflammatory | Pharmacological activity of the essential oil of Bupleurum Gibraltaricum: Anti-inflammatory activity and effects on isolated rat uteri | Ocete, M.A. | J. Ethnopharmacology, 1989, 25(3):305-13 |
| | anti-inflammatory | Cannabis and Cannabis Extracts: Greater Than the Sum of Their Parts | McPartland | Journal of Cannabis Therapeutics (The Haworth Integrative Healing Press, an imprint of The Haworth Press, Inc.) Vol. 1, No. 3/4, 2001, pp. 103-132 |

TABLE 8-continued

Non-limiting Compilation of the Sources Used to Develop Terpene Base Entourage Factors and Terpene Synergy Factors

| Terpene | Effect | Article title | First Author | Journal ref |
|---|---|---|---|---|
| carvacrol | antimicrobial | Interaction of four monoterpenes contained in essential oils with model membranes: implications for their antibacterial activity | D'Arrigo, M. | Journal of agricultural and food chemistry, 2007, 55(15): 6300-8 |
| | | The antibacterial mechanism of carvacrol and thymol against *Echerichia coli* | Zhou, F. | Letters in applied microbiology, 2008, 47(3): 174-9 |
| | anti-inflammatory | Anti-inflammatory effects of carvacrol: evidence for a key role of interleukin-10 | Quintans-Junior, L.J. | European journal of pharmacology, 2013, 699(1-3): 112-7 |
| | antinociceptive | Antinociceptive activity of carvacrol (5-isopropyl-2-methylphenol) in mice | Rios, E.R. | The Journal of pharmacy and pharmacology, 2012, 64(12): 1722-9 |
| | antidepressant | Antidepressant-like effect of carvacrol (5-Isopropyl-2-methylphenol) in mice: involvement of dopaminergic system | Moura, B.A. | Fundamental & clinical pharmacology, 2011, 25(3): 362-7 |
| | anxiolytic | Anxiolytic-like effect of Carvacrol (5-isopropyl-2-methylphenol) in mice: involvement with GABAergic transmission | Venancio, E.T. | Fundamental & clinical pharmacology, 2010, 24(4): 437-43 |
| | antitumor antimutagenic antigenotoxic antispasmodic angiogenic antiplatelet AChE inhibitor antielastase antihepatotoxic insecticidal | Biological and pharmacological activities of carvacrol and carvacrol bearing essential oils | Baser, K.H. | Current pharmaceutical design, 2008; 14(29): 3106-19 |
| citral | anti-inflammatory | A Review on Anti-Inflammatory Activity of Monoterpenes | da Silveira e Sá, R.C. | Molecules 2013, 18: 1227-1254; doi:10.3390/molecules18011227 |
| | antimicrobial antiadipogenic | Effects of citral, a naturally occurring antiadipogenic molecule, on an energy-intense diet model of obesity | Modak, T. | Indian journal of pharmacology, 2011, 43(3): 300-5 |
| | hemolytic | The hemolytic activity of citral: evidence for free radical participation | Tamir, I. | Biochemical pharmacology, 1984, 33(19): 2945-50 |
| fenchol | Antibacterial | Screening of Antibacterial Activities of Twenty-One Oxygenated Monoterpenes | Kotan, R. | Zeitschrift für Naturforschung. Section C, Biosciences, 62 (7-8): 507. |
| g-terpinene | antioxidant | Unusual Antioxidant Behavior of α- and γ-Terpinene in Protecting Methyl Linoleate, DNA, and Erythrocyte | Li, G.X. | Journal of Agricultural and Food Chemistry, 2009, 57(9): 3943-3948 |
| | reduces serum cholesterol and triglycerides | Effects of gamma-terpinene on lipid concentrations in serum using Triton WR1339-treated rats | Inaba, N. | Bioscience, biotechnology, and biochemistry, 2003, 67(11): 2448-50 |
| | antifungal (dermatophyte) | In vitro susceptibility of dermatophytes to conventional and alternative antifungal agents | Silvestri, C. | Medical mycology, 2009, 47(3): 321-6 |
| limonene | antimicrobial anti-inflammatory antimutagenic | Interaction of four monoterpenes contained in essential oils with model membranes: implications for their antibacterial activity | D'Arrigo, M. | Journal of agricultural and food chemistry, 2007, 55(15): 6300-8 |
| | | A Review on Anti-Inflammatory Activity of Monoterpenes | da Silveira e Sá, R.C. | Molecules 2013, 18: 1227-1254; doi:10.3390/molecules18011227 |
| | anxiolytic | Anxiolytic-like activity and GC-MS analysis of (R)-(+)-limonene fragrance, a natural compound found in foods and plants. | Lima, N.G.P.B. | Pharmacology Biochemistry and Behavior, 2013, 103(3): 450-454 |
| | antinociceptive | Antinociceptive effect of the monoterpene R-(+)-limonene in mice. | de Melo, N. | Biological & pharmaceutical bulletin, 2007, 30(7):1217 |
| | inhibits adipocyte differentiation prevents hyperglycemia and dyslipidemia | Preventive and ameliorating effects of citrus d-limonene on dyslipidemia and hyperglycemia in mice with high-fat diet-induced obesity | Jing, L. | European Journal of Pharmacology, 2013, 715(1-3):46-55 |
| | anticancer | Limonene-induced regression of mammary carcinomas | Lindstrom, M.J. | Cancer Research, 1992, 52(14):4021-6 |
| | antioxidant | Antioxidant activity of limonene on normal murine lymphocytes: relation to H2O2 modulation and cell proliferation | Micucci, P. | Basic and clinical pharmacology and toxicology, 2010, 106(1): 38-44 |
| | anti-inflammatory immunosuppressant | d-Limonene modulates T lymphocyte activity and viability | Lappas, C.M. | Cellular Immunology, 2012, 279(1):30-41 |
| linalool | anti-inflammatory | A Review on Anti-Inflammatory Activity of Monoterpenes | da Silveira e Sá, R.C. | Molecules 2013, 18: 1227-1254; doi:10.3390/molecules18011227 |
| | local anesthetic | Taming THC: Potential cannabis synergy and phytocannabinoid-terpenoid entourage effects | Russo | British Journal of Pharmacology, 2011, 163(7):1344 |

TABLE 8-continued

Non-limiting Compilation of the Sources Used to Develop Terpene Base Entourage Factors and Terpene Synergy Factors

| Terpene | Effect | Article title | First Author | Journal ref |
|---|---|---|---|---|
| | anti-inflammatory analgesic | Anti-inflammatory activity of linalool and linalyl acetate constituents of essential oils | | Phytomedicine, 2002, 9, 721-726 |
| | sedative antidepressant anxiolytic | Cannabis and Cannabis Extracts: Greater Than the Sum of Their Parts | McPartland | Journal of Cannabis Therapeutics (The Haworth Integrative Healing Press, an imprint of The Haworth Press, Inc.) Vol. 1, No. 3/4, 2001, pp. 103-132 |
| | antimicrobial | Antimicrobial activity of the major components of the essential oil of Melaleuca alternifolia | Carson, C.F. | The Journal of applied bacteriology, 1995, 78(3): 264-9 |
| linalool oxide | anxiolytic | Anxiolytic-like effects of inhaled linalool oxide in experimental mouse anxiety models | Souto-Maior, F.N. | Pharmacology Biochemistry and Behavior, 2011, 100(2): 259-263 |
| Myrcene | analgesic | Myrcene mimics the peripheral analgesic activity of lemongrass tea | Lorenzetti, B.B. | Journal of Ethnopharmacology, 1991. 34(1): 43-48 |
| | antinociceptive | Effect of myrcene on nociception in mice | Rao, V.S.N. | Journal of Pharmacy and Pharmacology, 1990. 42(12): 877-878 |
| | antimutagenic | Evaluation of the mutagenicity of beta-myrcene in mammalian cells in vitro. | Zamith, H. | Environmental and molecular mutagenesis, 1991. 18(1): 28-34 |
| | sedative/motor relaxant | Central effects of citral, myrcene and limonene, constituents of essential oil chemotypes from *Lippia alba* (Mill.) N.E. Brown | Gurgel do Vale, T. | Phytomedicine, 2002. 9: 709-714 |
| | antioxidant | Antioxidative effects of curcumin, β-myrcene and 1,8-cineole against 2,3,7,8-tetrachlorodibenzo-p-dioxin-induced oxidative stress in rats liver | Ozdemir, I | Toxicology and industrial health, 2011 Jun; 27(5): 447-53 |
| p-cymene | antibiotic | Cannabis and Cannabis Extracts: Greater Than the Sum of Their Parts | McPartland | Journal of Cannabis Therapeutics (The Haworth Integrative Healing Press, an imprint of The Haworth Press, Inc.) Vol. 1, No. 3/4, 2001, pp. 103-132 |
| | antimicrobial | Interaction of four monoterpenes contained in essential oils with model membranes: implications for their antibacterial activity | D'Arrigo, M. | Journal of agricultural and food chemistry, 2007, 55(15): 6300-8 |
| | anti-inflammatory antinociceptive | Evaluation of the anti-inflammatory and antinociceptive properties of p-cymene in mice | Bonjardim, L.R. | Zeitschrift für Naturforschung. C, Journal of biosciences, 2012, 67(1-2): 15-21 |
| terpinolene | sedative | The sedative effect of inhaled terpinolene in mice and its structure-activity relationships | Ito | J Nat Med. 2013 Oct;67(4):833-7. doi: 10.1007/s11418-012-0732-1. Epub 2013 Jan 22. |
| | comforting, calming, sedative | The monoterpene terpinolene from the oil of Pinus mugo L. in concert with a-tocopherol and b-carotene effectively prevents oxidation of LDL | Grassman | Phytomedicine, 2005, 12(6-7): 416-23 |
| | antifungal | Detoxification of Terpinolene by Plant Pathogenic Fungus Botrytis cinerea | Farooq | Z Naturforsch C. 2002, 57(9-10): 863-6 |
| | anticancer antiproliferative antioxidant | Anticancer and antioxidant properties of terpinolene in rat brain cells | Aydin, E. | Arhiv za higijenu rada i toksikologiju, 2013, 64(3): 415-24 |
| thymol | antimicrobial | Interaction of four monoterpenes contained in essential oils with model membranes: implications for their antibacterial activity | D'Arrigo, M. | Journal of agricultural and food chemistry, 2007, 55(15): 6300-8 |
| | | The antibacterial mechanism of carvacrol and thymol against *Echerichia coli* | Zhou, F. | Letters in applied microbiology, 2008, 47(3): 174-9 |
| | anti-inflammatory | Anti-Inflammatory Activity of Thymol: Inhibitory Effect on the Release of Human Neutrophil Elastase | Culici, M. | Pharmacology, 2006, 77(3): 130-136 |
| | antioxidant antifungal | Antioxidant Potential of Thymol Determined by Chemiluminescence Inhibition in Human Neutrophils and Cell-Free Systems | Culici, M. | Pharmacology, 2006, 76(2): 61-68 |
| | disinfectant | Silver nitrate and thymol; two disinfectants effective against *Legionella pneumophila* | | The Journal of hospital infection, 1990, 15(4): 395-6 |
| caryophyllene | anti-inflammatory cytoprotective antimalarial | Cannabis and Cannabis Extracts: Greater Than the Sum of Their Parts | McPartland | Journal of Cannabis Therapeutics (The Haworth Integrative Healing Press, an imprint of The Haworth Press, Inc.) Vol. 1, No. 3/4, 2001, pp. 103-132 |
| | anti-inflammatory via PGE1 CB2 agonist | Taming THC: potential cannabis synergy and phytocannabinoid-terpenoid entourage effects, also Beta caryophyllene is a dietary cannabinoid | Russo, Gertsch, J. | British Journal of Pharmacology (2011) 163 1344-1364, also PNAS 105(26):9099-104 |

TABLE 8-continued

Non-limiting Compilation of the Sources Used to Develop Terpene Base Entourage Factors and Terpene Synergy Factors

| Terpene | Effect | Article title | First Author | Journal ref |
|---|---|---|---|---|
| | anti-inflammatory | Anti-inflammatory effects of compounds alpha-humulene and (?)-trans-caryophyllene isolated from the essential oil of Cordia verbenacea | Fernandes et al | European Journal of Pharmacology (2007), 569(3), 228-236 |
| | anxiolytic | The anxiolytic-like effect of an essential oil derived from Spiranthera odoratissima A. St. Hil. leaves and its major component, -caryophyllene, in male mice | Galdino et al | Progress in Neuro-Psychopharmacology & Biological Psychiatry 38 (2012) 276-284 |
| caryophyllene oxide | decreases platelet aggregation antifungal insecticidal stimulant | Taming THC: potential cannabis synergy and phytocannabinoid-terpenoid entourage effects | Russo, | British Journal of Pharmacology (2011) 163 1344-1364 |
| a-humulene | anti-inflammatory | Anti-inflammatory effects of compounds alpha-humulene and (?)-trans-caryophyllene isolated from the essential oil of Cordia verbenacea | Fernandes et al | European Journal of Pharmacology (2007), 569(3), 228-236 |
| | antiasthmatic | Preventive and therapeutic anti-inflammatory properties of the sesquiterpene α-humulene in experimental airways allergic inflammation | Rogerio, AP. | British Journal of Pharmacology, 2009, 158(4): 1074-1087 |
| | antiproliverative | Assessment of the antioxidant and antiproliferative effects of sesquiterpenic compounds in in vitro Caco-2 cell models | Vinholes, J. | Food Chemistry, 2014, 156): 204-211 |

In some embodiments, if it appeared that there were more publications or studies referencing a specific effect, or if it appeared the effect was "stronger", the assigned terpene base entourage factor and/or terpene synergy factor was larger.

In some embodiments, the terpene synergy factors were further based on the tables of entourage combinations in British Journal of Pharmacology, 2011, 163(7):1344 (Russo, Taming THC: Potential *cannabis* synergy and phytocannabinoid—terpenoid entourage effects). In some embodiments, terpene base entourage factors and/or terpene synergy factors were also assigned based on Russo, Ethan, "Aromatherapy and Essential Oils" Handbook of Psychotropic Herbs, The Hayworth Press, 2001; and K. Hüsnü Can Başer and Gerhard Buchbauer, Handbook of Essential Oils: Science, Technology and Applications, CRC Press 2010.

In some embodiments, terpene synergy factors terpene base entourage factors can be adjusted based improved data regarding the physiological effects of each of the terpenes and cannabinoids. For example, in some embodiments, the factors can be updated in response to newer publications describing physiological responses to various terpene combinations, or kinetic binding data to certain human receptors. In other embodiments, the factors can be adjusted based on patient surveys or feedback.

In some embodiments the present invention teaches that the final weighted entourage loading factors can be further modified by synergistic interactions between the terpenes within the sample's terpene profile. Thus in some embodiments, the final weighted entourage loading factors would be modified depending on the presence of particular analyte combinations that were expected to produce various forms of antagonism, agonism, modulation, etc.

For instance, in some embodiments an initial terpene base factor for limonene contribution to "energy" could be cancelled out through the terpene base factor of myrcene and/or linalool which have sedative effects. In some embodiments, these types of complex inter-terpene synergistic effects are calculated via an interaction matrix. For instance, while linalool itself is not known to increase focus it can reduce anxiety and if there is already increased focus from the presence of pinenes it may have an additive effect, while by itself it would do nothing. It also takes into account negative interactions. Myrcene does not contribute to "Energy" by itself, but it can possibly detract from any energy component resulting from the presence of limonene. In some embodiments, each entourage effect would have to be calculated with a separate matrix. An example interaction matrix for the focus entourage effect is shown below in Table 9. Values for each terpene-terpene combination, and terpene-cannabinoid interaction are presented in the corresponding cell.

TABLE 9

Example Terpene Interaction Matrix for Focus Entourage Effect

AChE Inh

Focus

Loading Matrix

| | myrcene | caryophyllene oxide | linalool | b-caryophyllene | a-humulene | a-terpineol | camphene | fenchol | b-pinene | a-terpinene | a-pinene | g-terpinene |
|---|---|---|---|---|---|---|---|---|---|---|---|---|
| myrcene | 0 | 0 | 0 | 0 | 0 | -1 | 0 | 0 | -1 | 0 | -1 | 0 |
| caryophyllene oxide | 0 | 0 | 0 | 0 | 0 | 0 | 0 | 0 | 0 | 0 | 0 | 0 |

TABLE 9-continued

Example Terpene Interaction Matrix for Focus Entourage Effect

AChE Inh

Focus

Loading Matrix

|  | | | | | | | | | | | | |
|---|---|---|---|---|---|---|---|---|---|---|---|---|
| linalool | 0 | 0 | 0 | 0 | 0 | −1 | 0 | 0 | −1 | 0 | −1 | 0 |
| b-caryophyllene | 0 | 0 | 0 | 0 | 0 | 0 | 0 | 0 | 0 | 0 | 0 | 0 |
| a-humulene | 0 | 0 | 0 | 0 | 0 | 0 | 0 | 0 | 0 | 0 | 0 | 0 |
| a-terpineol | −1 | 0 | −1 | 0 | 0 | 1 | 0 | 0 | 1 | 0 | 1 | 0 |
| camphene | 0 | 0 | 0 | 0 | 0 | 0 | 0 | 0 | 0 | 0 | 0 | 0 |
| fenchol | 0 | 0 | 0 | 0 | 0 | 0 | 0 | 0 | 0 | 0 | 0 | 0 |
| b-pinene | −1 | 0 | −1 | 0 | 0 | 1 | 0 | 0 | 4 | 0 | 2 | 0 |
| a-terpinene | 0 | 0 | 0 | 0 | 0 | 0 | 0 | 0 | 0 | 0 | 0 | 0 |
| a-pinene | −1 | 0 | −1 | 0 | 0 | 1 | 0 | 0 | 2 | 0 | 4 | 0 |
| g-terpinene | 0 | 0 | 0 | 0 | 0 | 0 | 0 | 0 | 0 | 0 | 0 | 0 |
| limonene | −1 | 0 | −1 | 0 | 0 | 0.5 | 0 | 0 | 1 | 0 | 1 | 0 |
| carene | 0 | 0 | 0 | 0 | 0 | 0 | 0 | 0 | 0 | 0 | 0 | 0 |
| b-ocimene | 0 | 0 | 0 | 0 | 0 | −1 | 0 | 0 | −1 | 0 | −1 | 0 |
| a-phellandrene | 0 | 0 | 0 | 0 | 0 | 0 | 0 | 0 | 0 | 0 | 0 | 0 |
| terpinolene | 0 | 0 | 0 | 0 | 0 | −1 | 0 | 0 | 0 | 0 | 0 | 0 |
| Total THC | 0 | 0 | 0 | 0 | 0 | −1 | 0 | 0 | −3 | 0 | −1 | 0 |
| Total CBD | −2 | 0 | 0 | 0 | 0 | 0.5 | 0 | 0 | 1 | 0 | 1 | 0 |
| Total CBG | 0 | 0 | 0 | 0 | 0 | 0 | 0 | 0 | 0 | 0 | 0 | 0 |
| Total THCV | 0 | 0 | 0 | 0 | 0 | 0 | 0 | 0 | 0 | 0 | 0 | 0 |
| Total CBDV | 0 | 0 | 0 | 0 | 0 | 0 | 0 | 0 | 0 | 0 | 0 | 0 |

|  | limonene | carene | b-ocimene | a-phellandrene | terpinolene | Total THC | Total CBD | Total CBG | Total THCV | Total CBDV | EE Score | EE Score Filtered for Mass |
|---|---|---|---|---|---|---|---|---|---|---|---|---|
| myrcene | −1 | 0 | 0 | 0 | 0 | 0 | −2 | 0 | 0 | 0 | −0.01 | 0 |
| caryophyllene oxide | 0 | 0 | 0 | 0 | 0 | 0 | 0 | 0 | 0 | 0 | 0 | 0 |
| linalool | −1 | 0 | 0 | 0 | 0 | 0 | 0 | 0 | 0 | 0 | −0.01 | 0 |
| b-caryophyllene | 0 | 0 | 0 | 0 | 0 | 0 | 0 | 0 | 0 | 0 | 0 | 0 |
| a-humulene | 0 | 0 | 0 | 0 | 0 | 0 | 0 | 0 | 0 | 0 | 0 | 0 |
| a-terpineol | 0.5 | 0 | −1 | 0 | −1 | −1 | 0.5 | 0 | 0 | 0 | 0.008 | 0 |
| camphene | 0 | 0 | 0 | 0 | 0 | 0 | 0 | 0 | 0 | 0 | 0 | 0 |
| fenchol | 0 | 0 | 0 | 0 | 0 | 0 | 0 | 0 | 0 | 0 | 0 | 0 |
| b-pinene | 1 | 0 | −1 | 0 | 0 | −3 | 1 | 0 | 0 | 0 | 0.028 | 0 |
| a-terpinene | 0 | 0 | 0 | 0 | 0 | 0 | 0 | 0 | 0 | 0 | 0 | 0 |
| a-pinene | 1 | 0 | −1 | 0 | 0 | −1 | 1 | 0 | 0 | 0 | 0.028 | 0 |
| g-terpinene | 0 | 0 | 0 | 0 | 0 | 0 | 0 | 0 | 0 | 0 | 0 | 0 |
| limonene | 1 | 0 | −1 | 0 | −1 | −1 | 0 | 0 | 0 | 0 | 0.008 | 0 |
| carene | 0 | 0 | 0 | 0 | 0 | 0 | 0 | 0 | 0 | 0 | 0 | 0 |
| b-ocimene | −1 | 0 | 0 | 0 | 0 | 0 | 0 | 0 | 0 | 0 | −0.01 | 0 |
| a-phellandrene | 0 | 0 | 0 | 0 | 0 | 0 | 0 | 0 | 0 | 0 | 0 | 0 |
| terpinolene | −1 | 0 | 0 | 0 | 0 | 0 | 0 | 0 | 0 | 0 | 0 | 0 |
| Total THC | −1 | 0 | 0 | 0 | 0 | 0 | 0 | 0 | 0 | 0 | −0.02 | 0 |
| Total CBD | 0 | 0 | 0 | 0 | 0 | 0 | 2 | 0 | 0 | 0 | 0.06 | 0 |
| Total CBG | 0 | 0 | 0 | 0 | 0 | 0 | 0 | 0 | 0 | 0 | 0 | 0 |
| Total THCV | 0 | 0 | 0 | 0 | 0 | 0 | 0 | 0 | 0 | 0 | 0 | 0 |
| Total CBDV | 0 | 0 | 0 | 0 | 0 | 0 | 0 | 0 | 0 | 0 | 0 | 0 |
| Total | | | | | | | | | | | 0.028 | 0.05 |

In some embodiments, the present invention teaches the presentation of entourage effects in alternative formats tailored to the intended audience. Thus in some embodiments, the entourage effect values of the present invention can be displayed in charts, as representative images, as color schemes, descriptions, or other presentation methods known to those with skill in the art.

In some embodiments, the present invention teaches the presentation of entourage effects values in pie charts, bar charts, line charts, or other applicable chart. In other embodiments, entourage effects values can be represented by images. For example, in some embodiments, each entourage effect category is associated with a stock image, which can be used to represent the expected physiological properties of the *cannabis* sample. In some embodiments, the aroma and flavor values of a sample are ranked, and the top 1, 2, 3, 4, 5, 6, 7, 8, 9, or 10 images are displayed on the report for fast recognition and association by the patient. In some embodiments only the top 2 images are displayed.

In some embodiments, dispensaries utilizing the presentation formats of the present invention will also have accompanying displays explaining how to interpret the results. Thus in some embodiments, dispensaries would explain the meaning of any color, picture, chart, or other presentation scheme used to represent the aroma and flavor values of the present invention.

In some embodiments, the reports of the present invention are meant to provide patients with information to assist them in determining if a particular *cannabis* sample satisfies certain organoleptic preferences, and/or conforms to desired therapeutic needs. In other embodiments however, the reports of the present can also influence the user's perception of the organoleptic properties and entourage effects. Aromas, flavors, and effects are very complicated perceptions, especially when dealing with the "polypharmacy" of *cannabis*, so these are only meant to be suggestions and they can vary depending on the person, the dose, and the time course of administration.

Incorporation of Patient Feedback and Studies into Classification and Reporting Schemes In some embodiments, the present invention teaches fixed aroma, flavor, and entourage loading factors developed through the analysis and interpretation of published organoleptic and physiological effects studies for *cannabis* terpenes. In other embodiments, the present invention teaches a feedback system by which the aroma, flavor, and entourage loading factors used in the classification and reporting schemes of the present invention are subject to adjustments based on the review of additional research publications and/or *cannabis* user studies or feedback.

In some embodiments the loading factors can be adjusted based on patient surveys or feedback at the dispensary, distributor, or online level. A third option would be an app for a mobile device that used a number of simple questions and/or "games" that could be used to assess the level of relaxation, creativity, reflexes, attention, time courses, etc. In some embodiments, these results could then be interpreted and fed directly to the database. The results of the surveys and apps could then be used to try to de convolute the complex superposition of properties and alter the loading matrices, which may provide even more accurate representations of the cultivars.

In some embodiments the data from patient feedback could be subjected to a principal component analysis to determine which terpene classes and which effects are correlated. Based on the known terpene and cannabinoid profiles of the different classes it may be possible to correlate the trait complexes with effects.

Example 1. Quantifying Variation in Absolute Terpene Contents

Figure 4A:
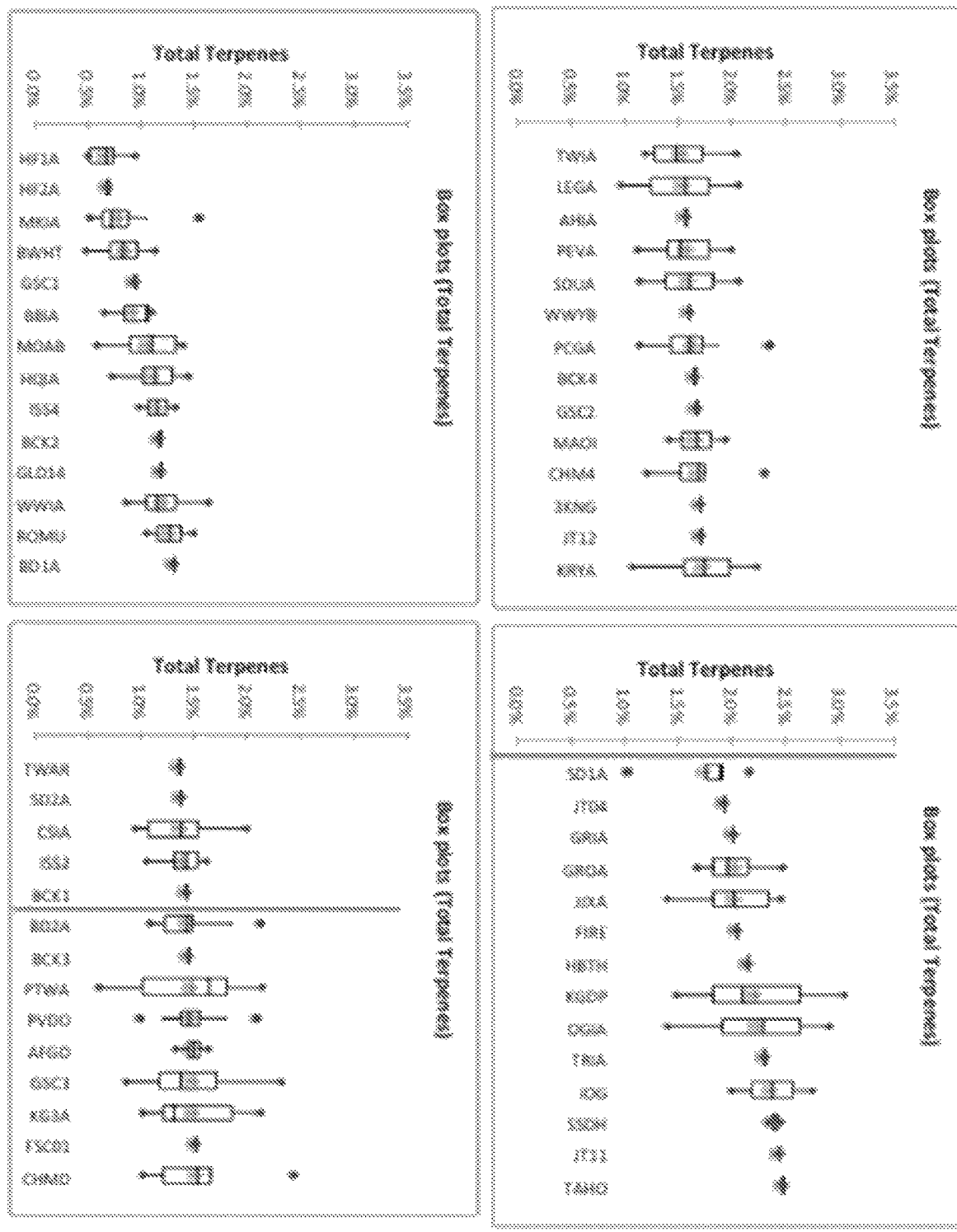
FIG. 4 (A)—Depicts box plots of the absolute total terpene content measurements of several genetically identical *cannabis* samples. (B)—Depicts box plots of the absolute total cannabinoid content measurements of several genetically identical *cannabis* samples. Cross near the center of each box plot represents the average terpene or cannabinoid content for that sample. Whiskers represent the minimum and maximum of the data set, with dots outside of this range representing outliers. Even genetically identical plants show some variability in the total absolute terpene contents and cannabinoid contents.
Figure 4B:
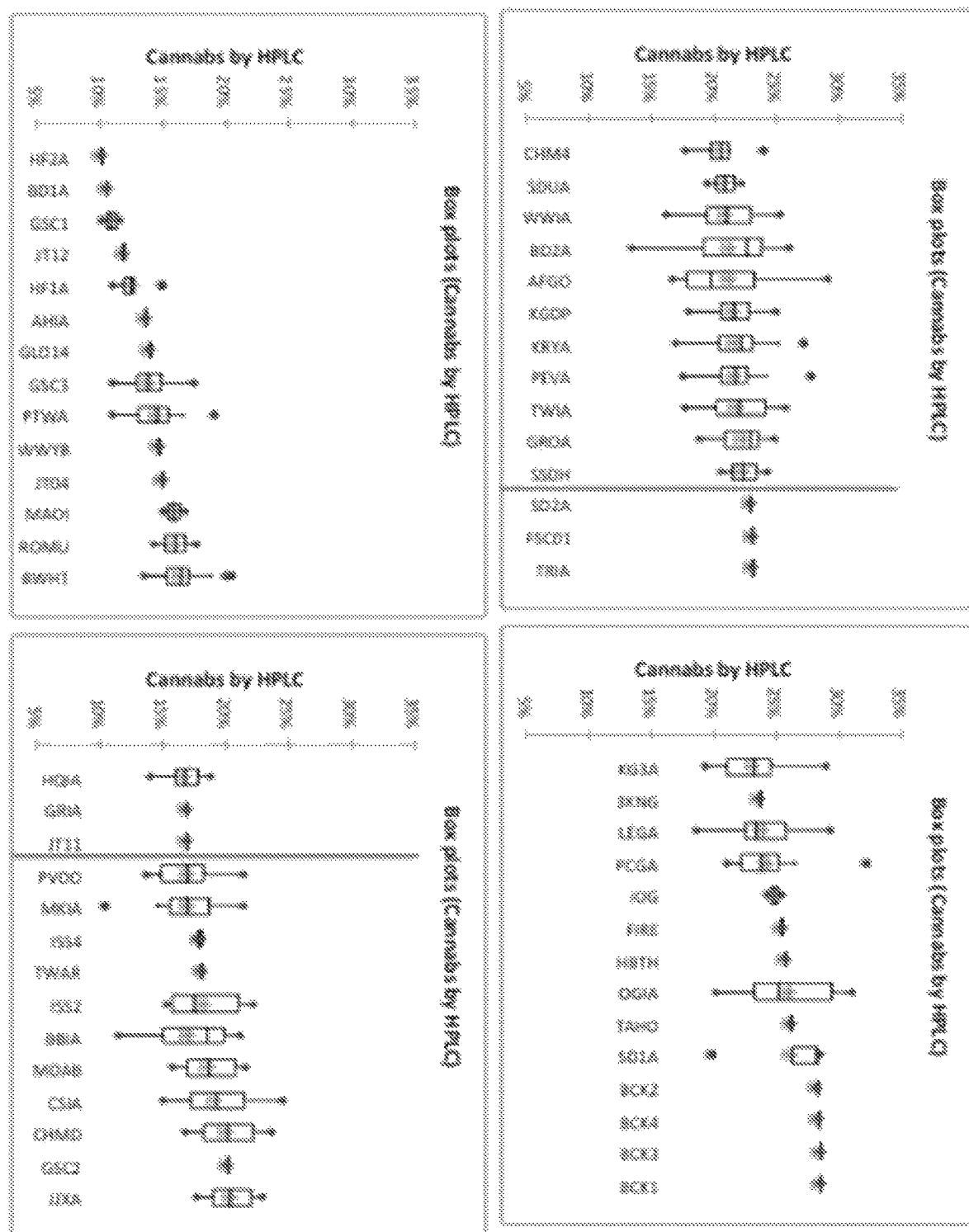

A total of 333 different lots of material covering 56 different cultivars were analyzed for cannabinoid and terpene content using Gas Chromatography with Flame Ionization Detectors. FIG. 4 shows the amount of total terpene content variation that could be measured within samples taken from plants with identical genetic background.

The most highly sampled cultivars included TWIA, LEGA, PCGA, OGIA, MOAB, and PEVA while some, such as BCK04, TAHO, and TWAR had only a single replicate and test results should be regarded with caution. The box plots in FIG. 4 are arranged from lowest to highest terpene content. Even the most highly sampled cultivars have lot-to-lot variation from 20% to 30%. The red cross on the box plots represents the average terpene accumulation value for each data set. The whiskers represent the minimum and maximum of the data set.

The cultivars with smaller spreads may have smaller GxE interactions and thus be more stable and better suited to a production environment. Blue dots outside the whiskers represent outliers. The box represents the middle half of the data set. Cultivars such as TWIA and CSIA are skewed towards the lower end of their range, cultivars such as MCA and MOAB are skewed towards the high end, and cultivars such as ROMU and KRYA are more of a typical Gaussian distribution.

Example 2. Survey of Existing Terpene Profile Diversities

A total of 333 different lots of material covering 56 different cultivars were analyzed for cannabinoid and terpene content using Gas Chromatography with Flame Ionization Detectors as described in Example 1.

A review of the measured accumulation values of all detectable terpenes in the *cannabis* samples produced a list of the 34 most common terpenes. Table 10 below lists the terpenes with the highest accumulation profiles, including the highest 17 accumulating terpenes (*), which are listed first, and are further distinguished by a star in the first column.

TABLE 10

| Most Common Terpenes in Cultivated Cannabis | |
|---|---|
| * | terpinolene |
| * | alpha phellandrene |
| * | beta-ocimine |
| * | carene |
| * | limonene |
| * | gamma terpinene |
| * | alpha pinene |
| * | alpha terpinene |
| * | beta pinene |
| * | fenchol |
| * | camphene |
| * | alpha terpineol |
| * | alpha humulene |
| * | beta caryophyllene |
| * | linalool |
| * | caryophyllene-oxide |
| * | myrcene |
|  | sabinene |
|  | cymene |
|  | cineole |
|  | cis-ocimene |
|  | (-)borneol |
|  | methyl-chavicol |
|  | nerol |
|  | neral |
|  | geraniol |
|  | gerinal |
|  | eugenol |
|  | geranyl-acetate |
|  | methyl-eugenol |
|  | cis-nerolidol |
|  | trans-nerolidol |
|  | pellitorine |
|  | phytol |

Example 3. Quantifying Variation in Relative Terpene Contents

A total of 333 different lots of material covering 56 different cultivars were analyzed for cannabinoid and terpene content using Gas Chromatography with Flame Ionization Detectors as described in Example 1.

The resulting absolute terpene contents were then converted to relative terpene contents by first adding the absolute contents of each of the terpenes in the extended terpene profile as defined in Example 2, and listed in Table 10. This value was called the total terpene oil content. The absolute content of each of the terpenes was then individually divided by the total terpene oil content and multiplied by 100 to obtain the relative terpene content. Thus a *cannabis* plant with 1.2% myrcene, 0.5% carene, and 0.8% fenchol was determined to have a total terpene oil content of 2.5% and a relative terpene content of 48% myrcene, 20% carene, and 32% fenchol.

Figure 5A:
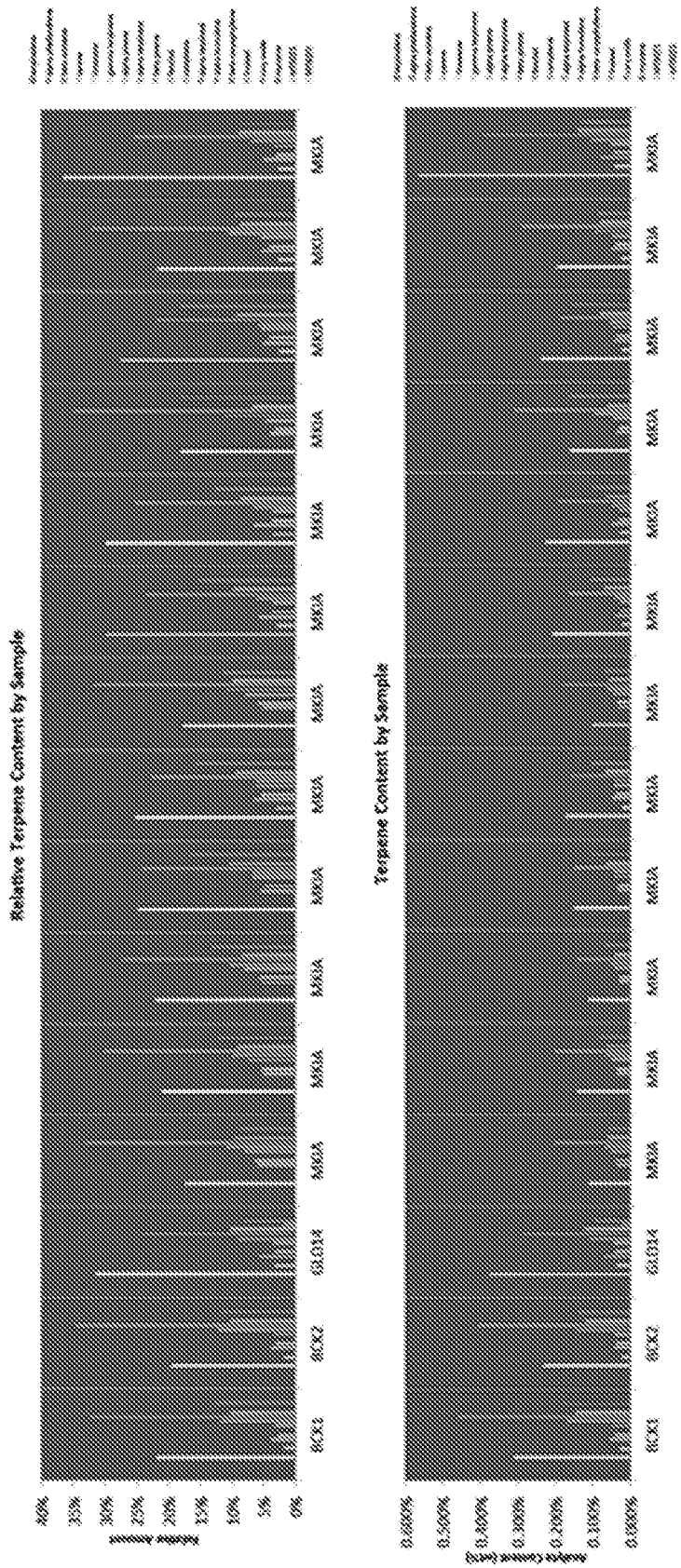
FIG. 5 (A)—Depicts bar charts for the relative (top) and absolute (bottom) terpene contents of 15 *cannabis* samples in the limonene-beta caryophyllene (LC) primary ethnobotanical classification group. (B)—Depicts a principal component analysis of the absolute (dots within larger oval) and relative (dots within smaller oval) terpene contents of the LC classification group samples. Both figures show reduced variation in relative terpene contents of samples as opposed to absolute contents which can vary greatly.
Figure 5B:
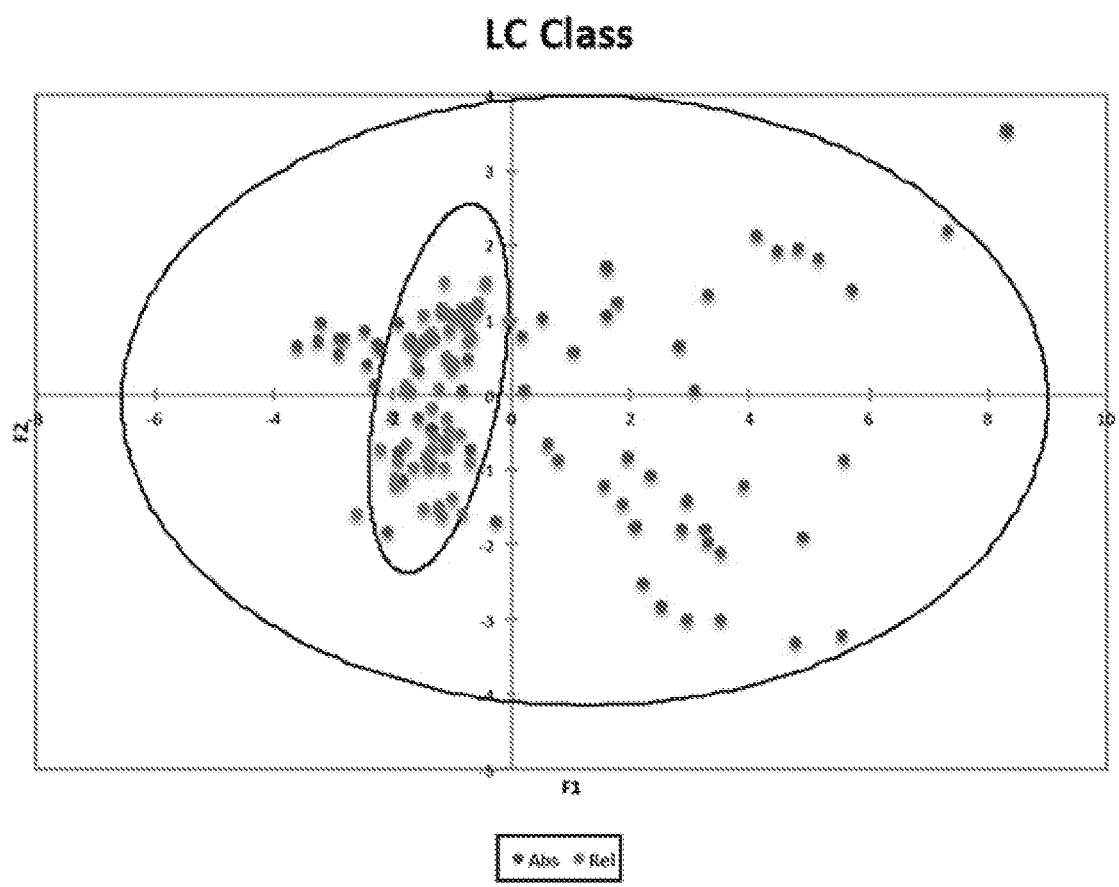

FIG. 5 shows the distribution of the relative values of the three highest accumulating terpenes in each variety. The results show that the relative contents values of terpenes exhibit less variation than that of the absolute values.

This result suggests that subsequent classification schemes are likely to be more reliable if they rely on relative terpene values for their categorizations, as these will be less vulnerable to variation due to environmental/growth differences.

Example 4. Classification of Cannabis Using Agglomerative Hierarchical Clustering (AHC)

A total of 333 different lots of material covering 56 different cultivars were analyzed for cannabinoid and terpene content using Gas Chromatography with Flame Ionization Detectors as described in Example 1.

Figure 6:
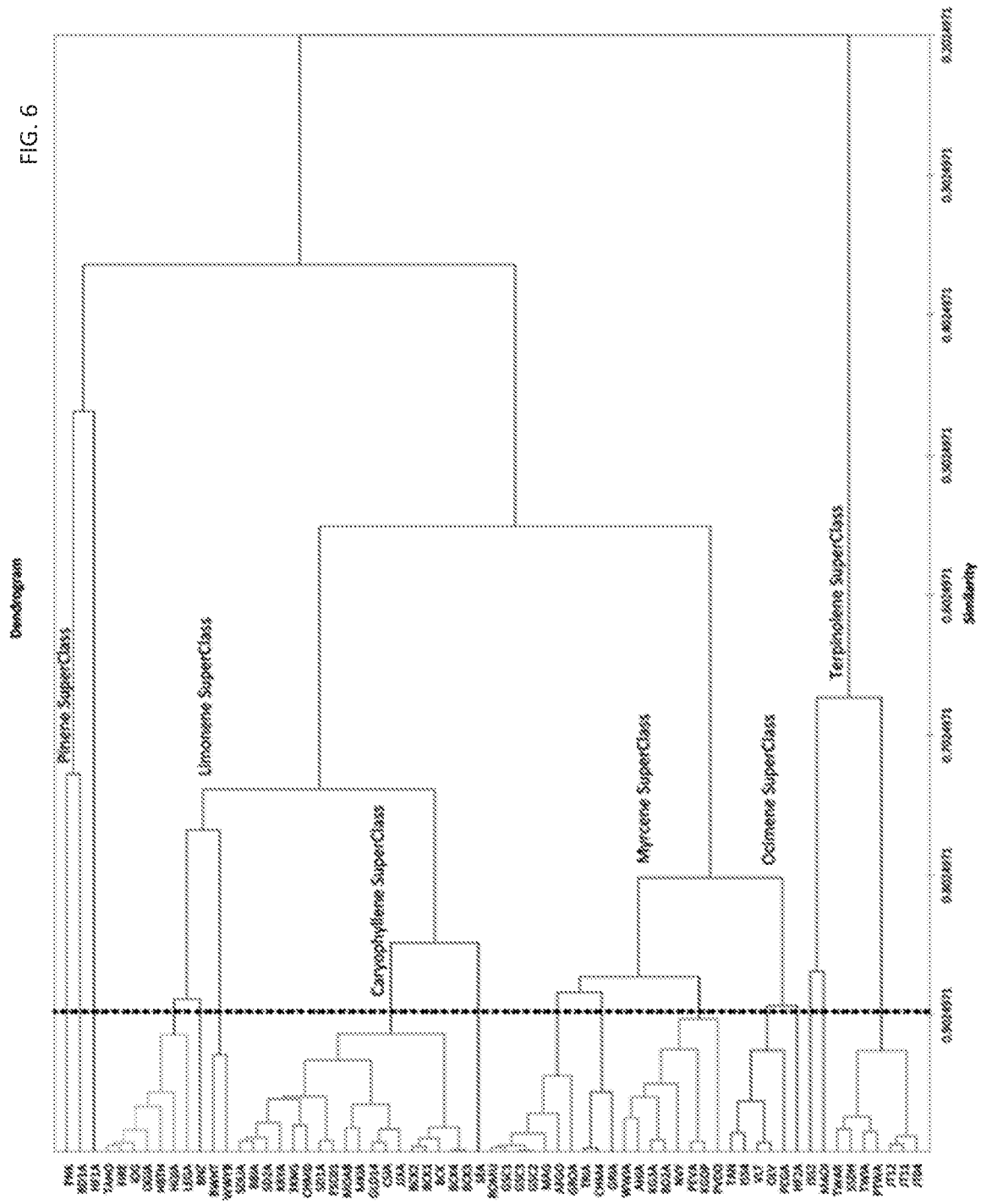
FIG. 6 Depicts a dendogram of agglomerative hierarchical clustering of 56 distinct *cannabis* cultivars based on each sample's average relative terpene contents. Variety names shown on the left with super class names labeled within the figure. Dotted line represents group truncation at 90% similarity cut offs as determined by Pearson's correlation distance measure.

The relative terpene contents of the extended terpene profile were calculated for each variety as described in Example 3. An AHC analysis was conducted using Pearson's correlation coefficient as the distance measure and weighted pair—group averaging as the agglomeration method with truncation at 90% similarity. The AHC analysis was conducted in XL Stat software (www.xlstate.com/en). The AHC the clusters are shown in FIG. 6.

Example 5. Classification of Cannabis Using Fixed Relative Terpene Level Analysis A total of 333 different lots of material covering 56 different cultivars were analyzed for cannabinoid and terpene content using Gas Chromatography with Flame Ionization Detectors as described in Example 1.

The relative terpene contents of the extended terpene profile were calculated for each variety as described in Example 3. The relative terpene contents of the top 3 highest accumulating terpenes were then used to categorize the cannabis samples into categories using the primary ethnobotanical method, which included the following steps:

1) Determining the relative content level of the highest (primary) accumulating terpene of the cannabis sample. This primary terpene is given a pre-determined "contribution factor".

2) Determining the relative content level of the second highest (secondary) accumulating terpene in the cannabis sample, and dividing it by the relative content level of the primary terpene. This number is the "secondary modulating factor."

3) Determining the relative content level of the third highest (tertiary) accumulating terpene in the cannabis sample, and dividing it by the relative content level of the primary terpene. This number is the "tertiary modulating factor."

4) Wherein the classification group of said cannabis sample is the primary terpene, and a secondary and tertiary terpene only if each of the secondary and tertiary modulating factors are greater than or equal to the pre-assigned "contribution factor" for the primary terpene.

The "contribution factor" for all terpenes is was 50%. All calculations were conducted using an excel-based macro which conducted the analysis steps as above. Letters for each of the groups was assigned according to Table 4 of the present disclosure.

Example 6. Comparison of the Fixed Factor and AHC Classifications

Figure 7A:
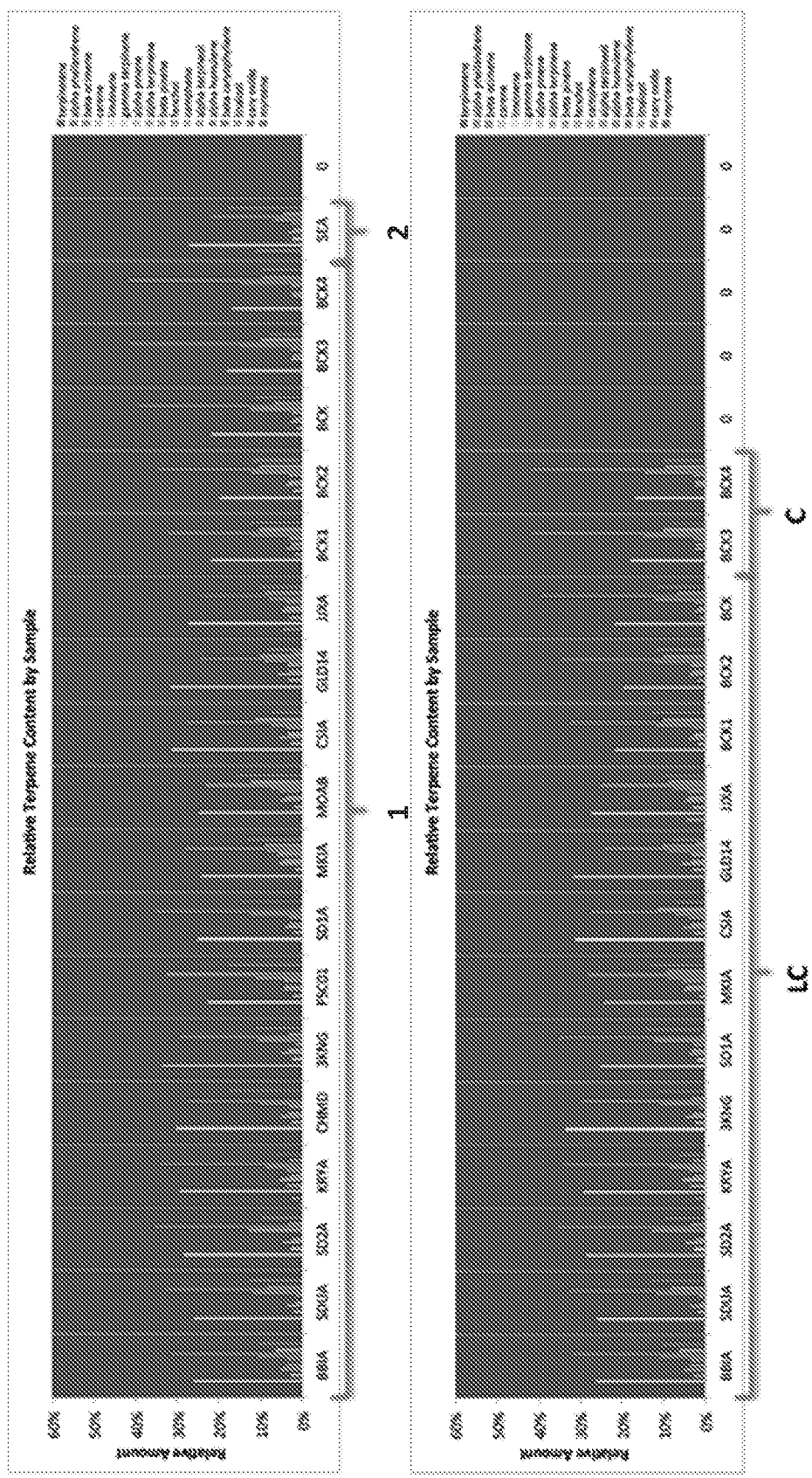
FIG. 7 Depicts a comparison of the *cannabis* classification achieved by agglomerative hierarchical clustering (AHC) and the primary ethnobotanical fixed value method of the present invention. The stacked bar charts show the relative terpene values of *cannabis* samples grouped by brackets according to their grouping in the AHC method (top), and the primary ethnobotanical fixed value method bottom. Numbers or letters below each bracket represent group names. (A)—Depicts bracket groups 1 and 2 for AHC. (B)—Depicts groups 3, 4, and 5 for AHC.
Figure 7B:
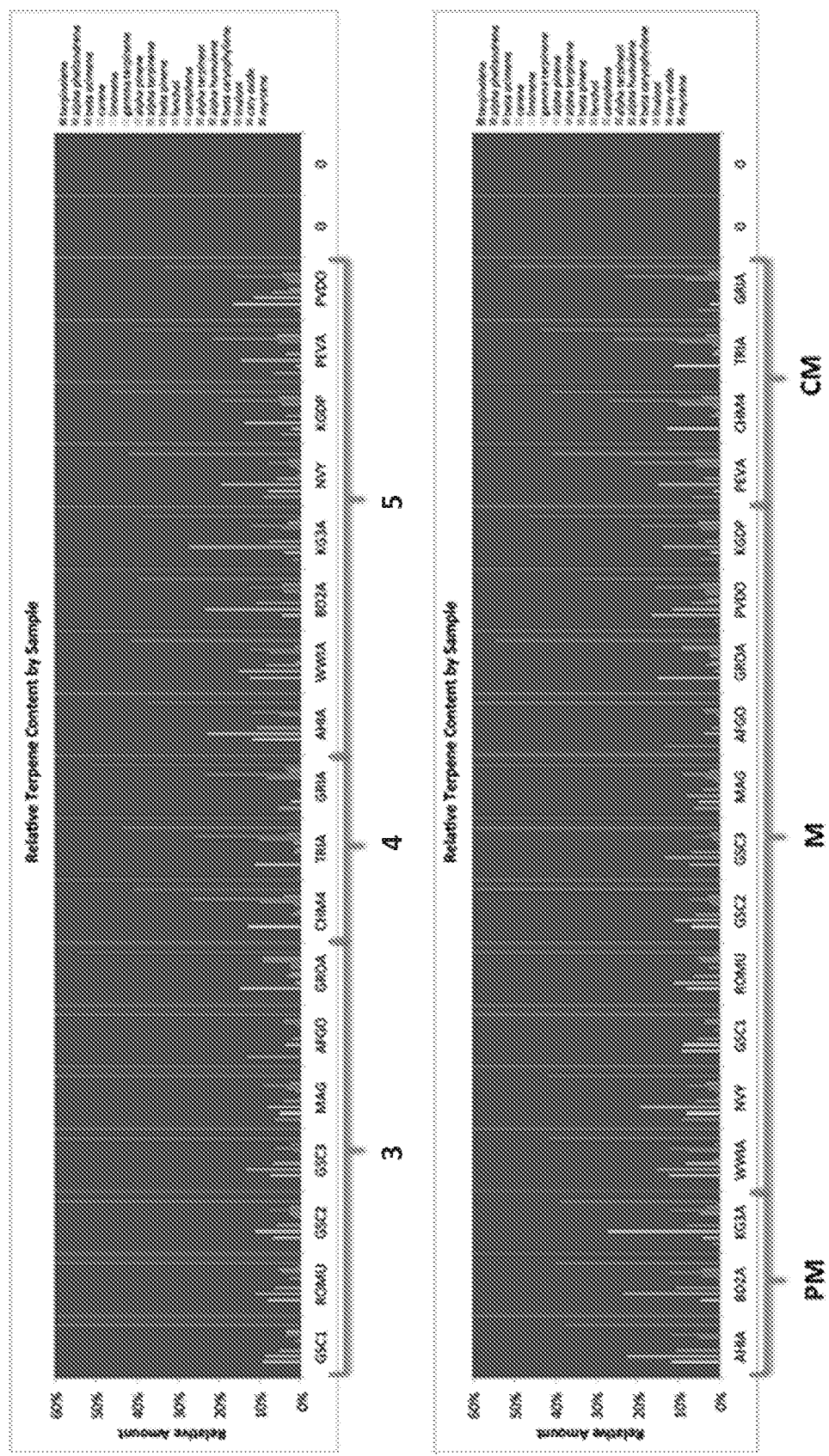

The cannabis classifications of the 333 samples conducted via the AHC methods of Example 4, and the fixed factor primary ethnobotanical method ("PE method") of Example 5 were compared. FIGS. 7A and 7B.

The groupings of the primary ethnobotanical method of the present invention showed some similarity to the groupings of the more traditional AHC analysis. For example, group 1 of the AHC analysis was largely replicated in the LC (limonene-beta caryophyllene) group of the PE method analysis (see FIG. 7A). Similarly, several of the heavily myrcene-dominant samples such as GSC1, ROMU, GSC2, GSC3, MAG, AFGO, and GROA were grouped together in both the AHC analysis and the PE method analysis (see FIG. 7B).

The PE method analysis however showed several marked improvements over the AHC analysis grouping. For example, the PE method analysis was able to distinguish between samples such as BBIA, SDUA, SD2A, and KRYA, with relatively similar limonene and beta caryophyllene levels (LC group), and samples such as BCK3, and BCK4, with dominant beta caryophyllene levels, and severely reduced limonene levels (C group, see FIG. 7A). In contrast, the AHC analysis grouped all the varieties into a single category, without distinguishing between the BBIA sample (with ~32% beta caryophyllene and 26% limonene), and the BCK4 sample (with 42% beta caryophyllene, and 17% limonene, see FIG. 7A).

Overall, the results from this comparison demonstrated the benefits of using the PE method classification scheme over that of traditional AHC analysis methods.

Example 7. Testing the Stability of Fixed Factor Classifications

One of the downsides of the sequential method classification scheme was its instability in grouping samples with minor differences in terpene content. The inventors of the present invention recognized the importance of a classification scheme that could accommodate small fluctuations in relative contents without shifting classes, while also recognizing large changes that could shift the classification of a specific cultivar without changing the "name" of the cultivar.

Figure 8:
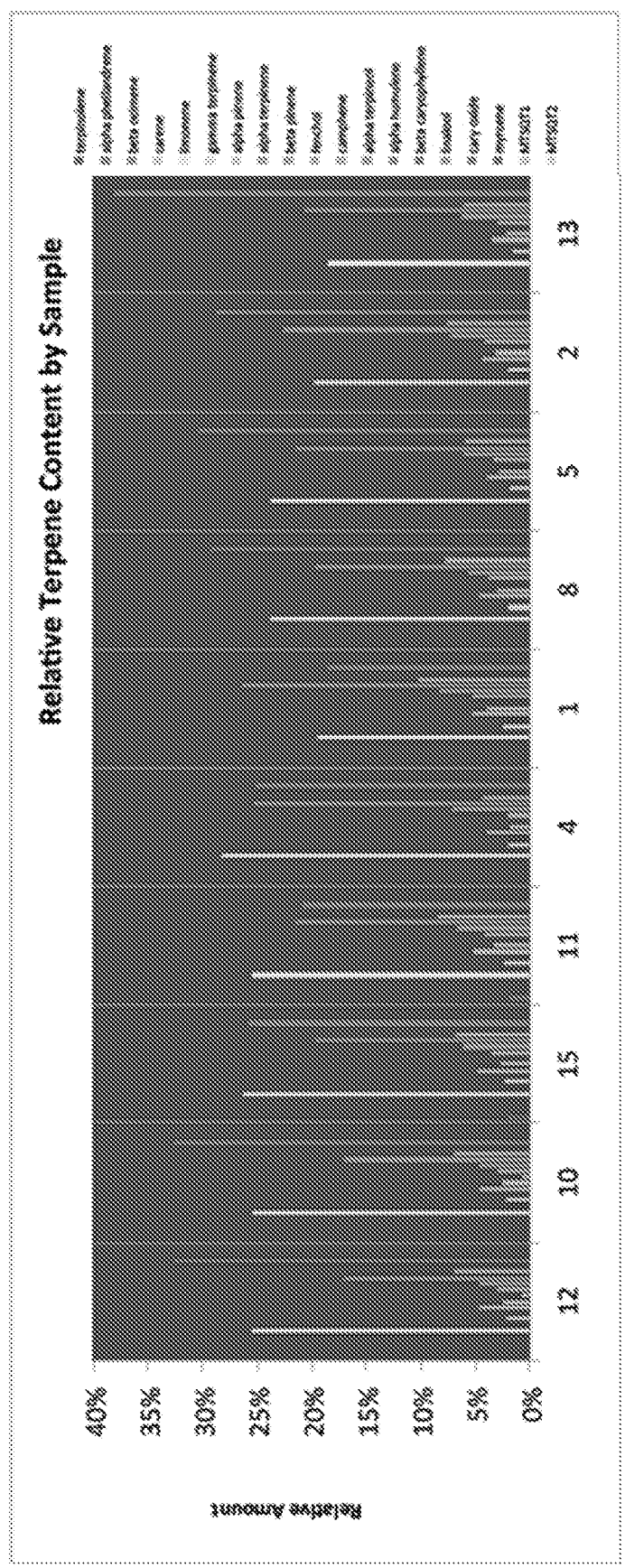
FIG. 8 Depicts bar charts of the relative terpene contents of 10 samples of a "Classic OG" *cannabis* variety.

The importance of stability is even more apparent with the current sensitivity of secondary metabolite profiles to environmental conditions and handling. In order to test whether the primary ethnobotanical method of classification could distinguish between minor and major fluctuations in terpene contents, 10 samples of a "Classic OG" variety were analyzed and tested as described in Example 7, and converted to relative terpene contents as described in Example 3. The relative terpene contents of the terpene profile are shown in FIG. 8.

In this comparison, sample numbers 12, 10, 15, 11, 4, 1, 8, 5, 2, and 13 are all essentially the same, with only minor differences in the terpene profile due to environmental effects. Under the PE method, these samples were classified together as LCM (FIG. 8).

In contrast, when these samples were classified under the sequential method, the slight variations in the relative content of myrcene caused the samples from the same variety to be reclassified. Under the sequential method, samples 12 and 13 are classified into a MLC category, samples 11 and 4 are classified into a LCM category, and sample 1 is reclassified into a CLM category. These small natural fluctuations in the terpene profile would not be expected to produce different organoleptic or physiological effects, thus making these additional categorizations artificial.

Thus the results of this example demonstrate the classification stability benefits offered by the PE method of classifying *cannabis*.

Example 8. Comparison of the Fixed Factor and Aroma-Based Classifications

In order to obtain further verification that the PE method was a utilitarian methodology, a number of cultivars from different classes (AFGO, KGDP, TWIA, PTWA, OGIA, CHMD, CHM4, LEGA, KRYA, JJXA, and PCGA) were given to experienced and blinded volunteers, who were asked to place the samples into aroma and flavor groups.

The volunteer-generated groupings were then compared to the PE method assigned group name for each sample. The results showed that samples analyzed based on organoleptic properties as determined by experienced and blinded volunteers, were placed in the same groups as the PE method the vast majority of the time. Despite similar names such as OG Legend and Classic OG, or Chem Four and Chem Dawg, the samples were correctly distinguished by both the classing system and organoleptic properties detected by volunteers.

The results of this initial experiment suggested that the PE method correlated with the real organoleptic properties experienced by the consumer.

Example 9. Chemical Analysis of Cannabinoids and Terpenes

Chemical analyses of the *cannabis* samples of the present invention was carried out using standard chemical separation techniques well known to those skilled in the arts. Qualitative identification of cannabinoids and terpenes was carried out by GCMS, while quantitative analysis was done by GC-FID and/or HPLC-PDA (Photo Diode Array). Initial field analyses of cannabinoids was performed using thin layer chromatography as described in ("*Cannabis* Inflorescence & Leaf QC" from The American Herbal Pharmacopeia 2013). The in-house assays for cannabinoids included orthogonal methods of GC-FID and HPLC for the highest level of accuracy.

Samples were prepared by grinding ~5 g of dried *cannabis* flower material in a coffee grinder. From this homogenized material, 500±20 mg was placed in a bead beater vial with ~1 g of 2 mm beads and 5 mL of working solution. Each sample was placed in the bead beater (BioSpec Products Inc.) and homogenized on high for 3 minutes. The vials were centrifuged at 1350×g, decanted into 50 mL falcon tubes, and the process was repeated with fresh working solution. After the second extraction the caps were removed, the vials were decanted into the appropriate falcon tubes, and the vials were rinsed into the falcon tubes with an additional 5 mL of working solution. For samples suspected of having lower concentrations of analytes (i.e. <10% THC or total terpene content ~0.5%), 3 mL portions of working solution could be employed. Approximately 2 mL of the extracts were placed in 2 mL centrifuge tubes, and the vials were centrifuged at 9500×g for 5 minutes. The supernatant was placed in a GC vial for terpene analysis without dilution. The supernatant was also diluted with working solution for GC and HPLC analysis. A 1:40 dilution provided the appropriate concentration for analysis of cannabinoids present at concentrations above 1.5%, while a 1:3 dilution allowed for analysis of cannabinoids below this level.

Terpenoids by Gas Chromatography-Flame Ionization Detector (GC-FID)

Terpenes were quantified by a method developed on a GC-FID instrument from Perkin Elmer™ (Waltham, Mass.). This method separates and quantifies 17 different terpenoids commonly found in *cannabis* plant tissue. The terpenoids are each quantified by their own individual calibration curves generated with analytical reference standards (Sigma Aldrich) and all use n-nonane as the internal standard.

The instrumentation includes a Clarus 680 gas chromatograph (GC) equipped with an autosampler, an Elite-5 column (Perkin Elmer™ (Waltham, Mass.), 30 m length, 0.25 mm internal diameter, 0.25 µm thickness film diameter) and a flame ionization detector (FID). Instrument control and data acquisition and analyses was accomplished by Total-Chrom software version 1.2.3.4 (Perkin Elmer™, Waltham, Mass.).

Calibration curves were generated by injecting each standard in triplicate and the RSDs provided the measure of precision while the absolute accuracy was determined by comparing the concentrations of the standards predicted by the calibration curve to their "known" values determined by dilution ratios. AOAC International standards for accuracy and precision were used as quality guidelines for every calibration. Check standards were run at the start, middle, and end of every analysis, and recalibration was performed when they varied more than +/−5% of their initial average response. Levels that failed the acceptance criteria and analytes were not quantified at those levels until recalibration of the instrument corrected the deficiency. Most of the curves were linear to nearly two orders of magnitude and based on the sample mass extracted (500 mg) and the two possible extraction volumes (3×3 mL or 3×5 mL), this provided quantitation of terpene levels from 0.01-0.9% or 0.02-1.5% (typical) in the plant matrix. In some embodiments, GC-FID measurements for terpenes were conducted in triplicate so as to provide 95% confidence intervals for each terpene measurement. In some embodiments, only a single measurement was made, and the confidence intervals were designated as N/A.

Cannabinoids by GC-FID

Cannabinoids were quantified by an analytical method developed and run on a Perkin Elmer™ (Waltham, Mass.) GC-FID instrument also. This method was developed to separate six neutral cannabinoids, CBD, CBG, CBN, THC, Δ8-THC, and CBC. The cannabinoids are each quantified by their own individual calibration curves generated with analytical reference standards (Restek) and all use tricosane as the internal standard. The retention time of THCV was determined by analyzing THV01 (vide infra) by GCMS, however since analytical standards were not available it was "quantified" by referencing the calibration curve for THC.

There was no need to consider chromatographic separation of acidic forms of the cannabinoids due to their immediate conversion to neutral form in the heated injector of the instrument, although a thorough study of the conversion efficiency of THCA was performed and is discussed in section iv. (orthogonal analyses of all samples).

The instrumentation includes a Clarus 680 gas chromatograph (GC) equipped with an autosampler, an Elite-1column (Perkin Elmer™ (Waltham, Mass.), 30 m length, 0.25 mm internal diameter, 0.25 µm thickness film diameter) and a flame ionization detector (FID). Instrument control and data acquisition and analyses was accomplished by TotalChrom software version 1.2.3.4 (Perkin Elmer™, Waltham, Mass.).

Calibration curves were generated by injecting each standard in triplicate and the RSDs provided the measure of precision while the absolute accuracy was determined by comparing the concentrations of the standards predicted by the calibration curve to their "known" values determined by dilution ratios. AOAC International standards for accuracy and precision were used as quality guidelines for every calibration. Check standards were run at the start, middle, and end of every analysis, and recalibration was performed when they varied more than +/−5% of their initial average response. Levels that failed the acceptance criteria and analytes were not quantified at those levels until recalibration of the instrument corrected the deficiency. Due to the very linear nature of the FID detector, the GC-FID cannabinoid assay generally provided satisfactory results over nearly two orders of magnitude (up to 1.0 mg/mL), however in order to use the same calibration solutions and "validation" procedures for both GC and HPLC the range was reduced to that of the HPLC method. Based on the sample mass extracted (500 mg) and a 3×3 mL extraction (low oil samples), a 1:3 dilution provided quantitation of cannabinoid levels from 0.09-1.35% and the 1:40 dilution from 1.15-18% in the plant matrix. A 3×5 mL extraction (high oil samples, typical), a 1:3 dilution provided quantitation of cannabinoid levels from 0.14-2.25% and the 1:40 dilution from 1.9-30% in the plant matrix.

In some embodiments, GC-FID measurements for cannabinoids were conducted in triplicate so as to provide 95% confidence intervals for each cannabinoid measurement. In some embodiments, only a single measurement was made, and the confidence intervals were designated as N/A.

Cannabinoids by High Performance Liquid Chromatography-Photo Diode Array Detector (HPLC-PDA))

An HPLC-PDA (also known as HPLC-DAD, or simply HPLC) assay was developed as an orthogonal method to GC-FED for cannabinoid analyses. This method quantifies six neutral cannabinoids (CBD, CBG, CBN, THC, $\Delta$8-THC, and CBC) as well as THCA based on calibration curves generated with analytical standards and an internal reference standard (ibuprofen). The only acidic cannabinoid that is readily available as an analytical standard in the United States is THCA, so levels of CBDA, CBGA, and THCVA are estimated by reference to THCA calibration.

HPLC analyses were performed using a Perkin Elmer™ (Waltham, Mass.) HPLC system comprised of a Flexar FX-15 binary pump, a Flexar 5-CH solvent manager, an FX UHPLC autosampler, and a Peltier LC column oven. UV data was collected at 228 nm and 280 nm with a Flexar FX-PDA UHPLC detector. Chromatography was performed on a Brownlee SPP C18 column (PKI N9308411, 2.7 μm, 3.0×150 mm), protected by a Brownlee SPP C18 guard column (2.7 μm, 2.1×5 mm). HPLC system control, data acquisition and analyses were performed with Chromera software version 3.4.1.5904.

Calibration was achieved by performing a five-point calibration curve (0.016-0.25 mg/mL for each analyte) followed by linear regression analysis. This analysis was performed with Microsoft Excel (Redmond, Wash.) software. The calibration curves were generated by injecting each standard in triplicate and the RSDs provided the measure of precision while the absolute accuracy was determined by comparing the concentrations of the standards predicted by the calibration curve to their "known" values determined by dilution ratios. AOAC International standards for accuracy and precision were used as quality guidelines for every calibration. Check standards were run at the start, middle, and end of every analysis, and recalibration was performed when they varied more than +/−5% of their initial average response.

In some embodiments, HPLC measurements for cannabinoids were conducted in triplicate so as to provide 95% confidence intervals for each cannabinoid measurement. In some embodiments, only a single measurement was made, and the confidence intervals were designated as N/A. In these cases, an Agilent™ 1290 HPLC was used with a 0.5 mL/min flow rate on a Poroshell 120 EC-C18, 2.1×150 mm, 2.7 uM column.

Orthogonal Analyses of all Samples

The cannabinoid content was quantified by both GC-FID and HPLC. The main difference between GC and HPLC is that GC involves thermal stress and mainly resolves analytes by boiling points while HPLC does not involve heat and mainly resolves analytes by polarity. There are several reasons that this orthogonal approach to analyses is desirable for highly accurate and reproducible results in determining chemotype. The first reason is related to the difference between the cannabinoids produced naturally by the plant (the acidic cannabinoids) and those that are bioactive (the neutral cannabinoids). *Cannabis* biosynthesizes all the cannabinoids in their relatively unstable acidic forms, and these forms are generally not bioactive in the traditional sense. The application of heat (flame, vaporizer, oven, etc) causes a loss of the carboxylic acid group and generates the neutral forms of the cannabinoids, which are generally the bioactive forms that are sought after, however this process is highly variable and not quantitative. If one wants to know the native phytochemical profile of the plant then HPLC should be used since this assay does not involve heat. If one wants to know the possible available amount of bioactive cannabinoids, then GC should be used since conversion to these forms in the injector of the GC is an inherent part of the analytical method.

The second reason is also related to the difference between the acidic and neutral cannabinoids, but has to do with the availability of analytical standards to calibrate the instruments. While all of the neutral cannabinoids (THC, CBG, CBC, CBD, and CBN) are available as analytical standards, THCA is the only acidic cannabinoid available as an analytical standard and the instruments were only calibrated for quantification using actual analytical standards. Technically the HPLC assay could characterize the naturally occurring chemotypes, but the acidic analytes are not available as standards, so this quantification is approximate and considered for information only. The acidic analytes are all quantified by reference to the calibration curve for THCA, and this is not an unreasonable assumption as many of them have approximately the same spectral properties. The GC assay is calibrated with analytical standards, but these are the neutral cannabinoids and their formation from the naturally occurring acidic cannabinoids in the GC injector is not quantitative, which complicates exact characterization of the naturally occurring chemotype.

The final reason is simply to have an internal crosscheck of our results by using orthogonal testing methods. Each type of assay (GC and HPLC) has its strengths and weaknesses, and by using both methods one can compare results and ensure that both the identification and quantitation of the components are accurate. A caveat to this, as mentioned above, is that the conversion of the acidic forms to the neutral forms is not quantitative due to thermal degradation. Under the highly optimized conditions of a GC injector we have found conversion can vary between 75-85% (for analytical THCA standards), while *cannabis* samples generally have a conversion of 70-80%. Similar conversion rates are also described in literature for highly optimized analytical instruments (Dussy et al. 2004). Because of this incomplete conversion our GC results are consistently 20-30% lower than the HPLC results for *cannabis* samples. This same conversion efficiency can be applied to estimate the maximum availability of THC based on THCA content when smoking or vaporizing *cannabis*.

Method "Validation"

In order to demonstrate the performance of a method of analysis, a systematic process known and method validation can be carried out. This process demonstrates the method is fit for its intended purpose and is necessary for the confident use of that method, providing assurance that the results that are reported are precise, accurate, and reflective of the sample. Very few labs in the *cannabis* industry attempt to validate their assays and this fact, combined with inappropriate sampling have resulted in erroneous data for several varieties. In order to validate the analytical methods employed for this project, an abbreviated protocol similar to Single Laboratory Validation (SLV) was carried out. Assay "validation" was carried out by spiking blank matrix with the analytes at low, med, and high concentrations and carrying out the assay procedure in replicate (n=5). While some analytes provided better results than others the analyte RSDs, recoveries, and precisions at these concentrations satisfied AOAC guidance (based on mg/mL). In general the RSDs for the terpenes at the low, medium, and high concentrations (varied by terpene but generally 0.016, 0.125, and 1.0 mg/mL) were less than 5%, 4%, and 3% respectively. The absolute bias for these analytes was generally less than 10%, 4%, and 2%. In general the RSDs for the cannabinoids by both GC and HPLC at the low, medium, and high concentrations (0.016, 0.61, and 0.250 mg/mL) were less than 2%, 2%, and 1% respectively. The absolute bias for these analytes was generally less than 10%, 2%, and 2%. The assays all provided satisfactory S/N ratios at the lowest level and this was initially taken as the LOQ. After subsequent re-calibrations (n=3 at each level), the LOQ was taken as the lowest level of the calibration curve that provided acceptable accuracy (<10% error) determined by comparing the known concentration levels (determined by dilution ratios) to the predicted levels (obtained from the signal and calibration curve).

The error between the known and measured values establishes the accuracy of the method and verifies that real samples do not present any matrix effects that influence the resulting measurements. The precision, or closeness of individual measurements, of the method is also determined by carrying out all analyses in replicate (n=5). Guidance for acceptable values was taken from publications provided by the AOAC.

The in-house validation revealed that the above-described chemical analysis methods were accurate and reliable, and the use of orthogonal methods of analyses provided an internal check on the assays as well as an understanding of the use of GC to analyze thermally unstable molecules. Using multiple dilution ratios kept samples in the linear ranges of the assays, and method validation verified that precise and accurate results were obtained.

Example 10. Preparing a *Cannabis* Flavor and Aroma Report

A chemical analysis was conducted for a sample of *cannabis* variety YLW03 according to the methods described in Example 9. The absolute contents of each of the terpenes within the terpene profile were recorded and multiplied by each terpene's aroma and flavor descriptor loading values as shown in Tables 11 and 12 below. A table of the loading values used in this example can be seen in earlier Tables 5 and 6.

TABLE 11

Multiplication of Terpene Values by Aroma Descriptor Loading Factors

| # | Analyte | Analyte (mass %) | Sweet | Fruity | Citrusy | Floral | Herbal |
|---|---|---|---|---|---|---|---|
| 1 | myrcene | 0.35% | 0 | 0 | 0 | 0.0008865 | 0.003546 |
| 2 | Caryophyllene oxide | 0.01% | 0.00002575 | 0 | 0 | 0 | 0 |
| 3 | linalool | 0.05% | 0.000509 | 0.0002545 | 0.000509 | 0.000509 | 0 |
| 4 | b-caryophyllene | 0.23% | 0.001162 | 0 | 0 | 0 | 0 |
| 5 | a-humulene | 0.06% | 0 | 0 | 0 | 0 | 0 |
| 6 | a-terpineol | 0.03% | 0 | 0 | 0.0001685 | 0.000337 | 0 |
| 7 | camphene | 0.00% | 0 | 0 | 0 | 0 | 0 |
| 8 | fenchol | 0.02% | 0.0000375 | 0.0000375 | 0 | 0 | 0 |
| 9 | b-pinene | 0.11% | 0 | 0 | 0 | 0 | 0 |
| 10 | a-terpinene | 0.04% | 0 | 0.00009025 | 0.000361 | 0 | 0 |
| 11 | a-pinene | 0.06% | 0 | 0 | 0 | 0 | 0.00015675 |
| 12 | g-terpinene | 0.02% | 0.000169 | 0.00004225 | 0.0000845 | 0 | 0 |
| 13 | limonene | 0.16% | 0.0007915 | 0.001583 | 0.001583 | 0 | 0 |
| 14 | carene | 0.04% | 0.000379 | 0 | 0.000379 | 0 | 0 |
| 15 | b-ocimene | 0.32% | 0.001578 | 0 | 0 | 0.003156 | 0.003156 |
| 16 | a-phellandrene | 0.05% | 0 | 0 | 0.00049 | 0 | 0.00049 |
| 17 | terpinolene | 1.05% | 0.010545 | 0 | 0.0052725 | 0 | 0 |
| | TOTAL Chart Scaling | 50 | 0.7598375 | 0.100375 | 0.442375 | 0.244425 | 0.3674375 |

TABLE 11-continued

Multiplication of Terpene Values by Aroma Descriptor Loading Factors

| # | Piney | Earthy | Camphor | Spicy | Tropical |
|---|---|---|---|---|---|
| 1 | 0.001773 | 0.0008865 | 0 | 0 | 0 |
| 2 | 0 | 0.0000515 | 0 | 0.0000515 | 0 |
| 3 | 0 | 0 | 0 | 0 | 0.00012725 |
| 4 | 0 | 0.001162 | 0.001162 | 0.002324 | 0 |
| 5 | 0 | 0.0003065 | 0 | 0 | 0 |
| 6 | 0.000337 | 0.00008425 | 0 | 0 | 0 |
| 7 | 0 | 0 | 0 | 0 | 0 |
| 8 | 0.00015 | 0.0000375 | 0.00015 | 0 | 0 |
| 9 | 0.001122 | 0.000561 | 0.001122 | 0 | 0 |
| 10 | 0.0001805 | 0.0001805 | 0.00009025 | 0.00009025 | 0 |
| 11 | 0.000627 | 0.0003135 | 0.000627 | 0 | 0 |
| 12 | 0.0000845 | 0.00004225 | 0 | 0 | 0.00004225 |
| 13 | 0 | 0 | 0 | 0 | 0.0007915 |
| 14 | 0 | 0 | 0 | 0 | 0 |
| 15 | 0 | 0 | 0 | 0 | 0.004734 |
| 16 | 0 | 0.0001225 | 0 | 0.0001225 | 0.000245 |
| 17 | 0.0052725 | 0.00263625 | 0.0052725 | 0 | 0 |
| TOTAL | 0.477325 | 0.3192125 | 0.4211875 | 0.1294125 | 0.297 |

TABLE 12

Multiplication of Terpene Values by Flavor Descriptor Loading Factors

| # | Analyte | Analyte (mass %) | Sweet | Fruity | Citrusy | Floral |
|---|---|---|---|---|---|---|
| 1 | myrcene | 0.35% | 0 | 0.001773 | 0.001773 | 0 |
| 2 | caryophyllene oxide | 0.01% | 0 | 0 | 0 | 0 |
| 3 | linalool | 0.05% | 0 | 0.000509 | 0.0002545 | 0.000509 |
| 4 | b-caryophyllene | 0.23% | 0 | 0 | 0.000581 | 0 |
| 5 | a-humulene | 0.06% | 0 | 0 | 0 | 0 |
| 6 | a-terpineol | 0.03% | 0 | 0 | 0 | 0.000337 |
| 7 | camphene | 0.00% | 0 | 0 | 0 | 0 |
| 8 | fenchol | 0.02% | 0 | 0 | 0.000075 | 0 |
| 9 | b-pinene | 0.11% | 0 | 0 | 0 | 0 |
| 10 | a-terpinene | 0.04% | 0 | 0.0001805 | 0.0001805 | 0 |
| 11 | a-pinene | 0.06% | 0 | 0.00015675 | 0 | 0 |
| 12 | g-terpinene | 0.02% | 0 | 0.000169 | 0.000169 | 0 |
| 13 | limonene | 0.16% | 0.001583 | 0.0007915 | 0.001583 | 0 |
| 14 | carene | 0.04% | 0 | 0 | 0.000379 | 0 |
| 15 | b-ocimene | 0.32% | 0 | 0 | 0 | 0.003156 |
| 16 | a-phellandrene | 0.05% | 0 | 0.000245 | 0.000245 | 0 |
| 17 | terpinolene | 1.05% | 0 | 0.0052725 | 0 | 0.00263625 |
| TOTAL | Chart Scaling | 50 | 0.07915 | 0.4548625 | 0.262 | 0.3319125 |

| # | Herbal | Piney | Earthy | Camphor | Spicy | Tropical |
|---|---|---|---|---|---|---|
| 1 | 0.003546 | 0 | 0.001773 | 0 | 0 | 0 |
| 2 | 0 | 0 | 0 | 0 | 0.000103 | 0 |
| 3 | 0 | 0 | 0.00012725 | 0 | 0 | 0.0002545 |
| 4 | 0 | 0 | 0.001162 | 0.002324 | 0.002324 | 0 |
| 5 | 0 | 0 | 0.000613 | 0 | 0 | 0 |
| 6 | 0 | 0 | 0 | 0 | 0 | 0 |
| 7 | 0 | 0 | 0 | 0 | 0 | 0 |
| 8 | 0 | 0 | 0 | 0 | 0 | 0 |
| 9 | 0 | 0.001122 | 0 | 0.000561 | 0 | 0 |
| 10 | 0 | 0.000361 | 0.00009025 | 0 | 0.00009025 | 0 |
| 11 | 0.00015675 | 0.000627 | 0.0003135 | 0.0003135 | 0.00015675 | 0 |
| 12 | 0 | 0.000169 | 0 | 0 | 0 | 0 |
| 13 | 0 | 0 | 0 | 0 | 0 | 0.0007915 |
| 14 | 0 | 0 | 0 | 0 | 0 | 0 |
| 15 | 0 | 0 | 0 | 0 | 0 | 0.004734 |
| 16 | 0 | 0.00049 | 0 | 0 | 0 | 0.0001225 |

TABLE 12-continued

| | | Multiplication of Terpene Values by Flavor Descriptor Loading Factors | | | | |
|---|---|---|---|---|---|---|
| 17 | 0.00263625 | 0.010545 | 0.0052725 | 0 | 0 | 0 |
| TOTAL | 0.31695 | 0.6657 | 0.467575 | 0.159925 | 0.1337 | 0.295125 |

A summary of the results are shown in Table 13 below.

TABLE 13

| | Summary Aroma/Flavor Interpretive Values | | | | | | | | | |
|---|---|---|---|---|---|---|---|---|---|---|
| | Sweet | Fruity | Citrusy | Floral | Herbal | Piney | Earthy | Camphor | Spicy | Tropical |
| Aroma | 0.760 | 0.100 | 0.442 | 0.244 | 0.367 | 0.477 | 0.319 | 0.421 | 0.129 | 0.297 |
| Flavor | 0.079 | 0.455 | 0.262 | 0.332 | 0.317 | 0.666 | 0.468 | 6.160 | 0.134 | 0.295 |
| Organoleptic | 0.839 | 0.555 | 0.704 | 0.576 | 0.684 | 1.143 | 0.787 | 0.581 | 0.263 | 0.592 |

Figure 9:
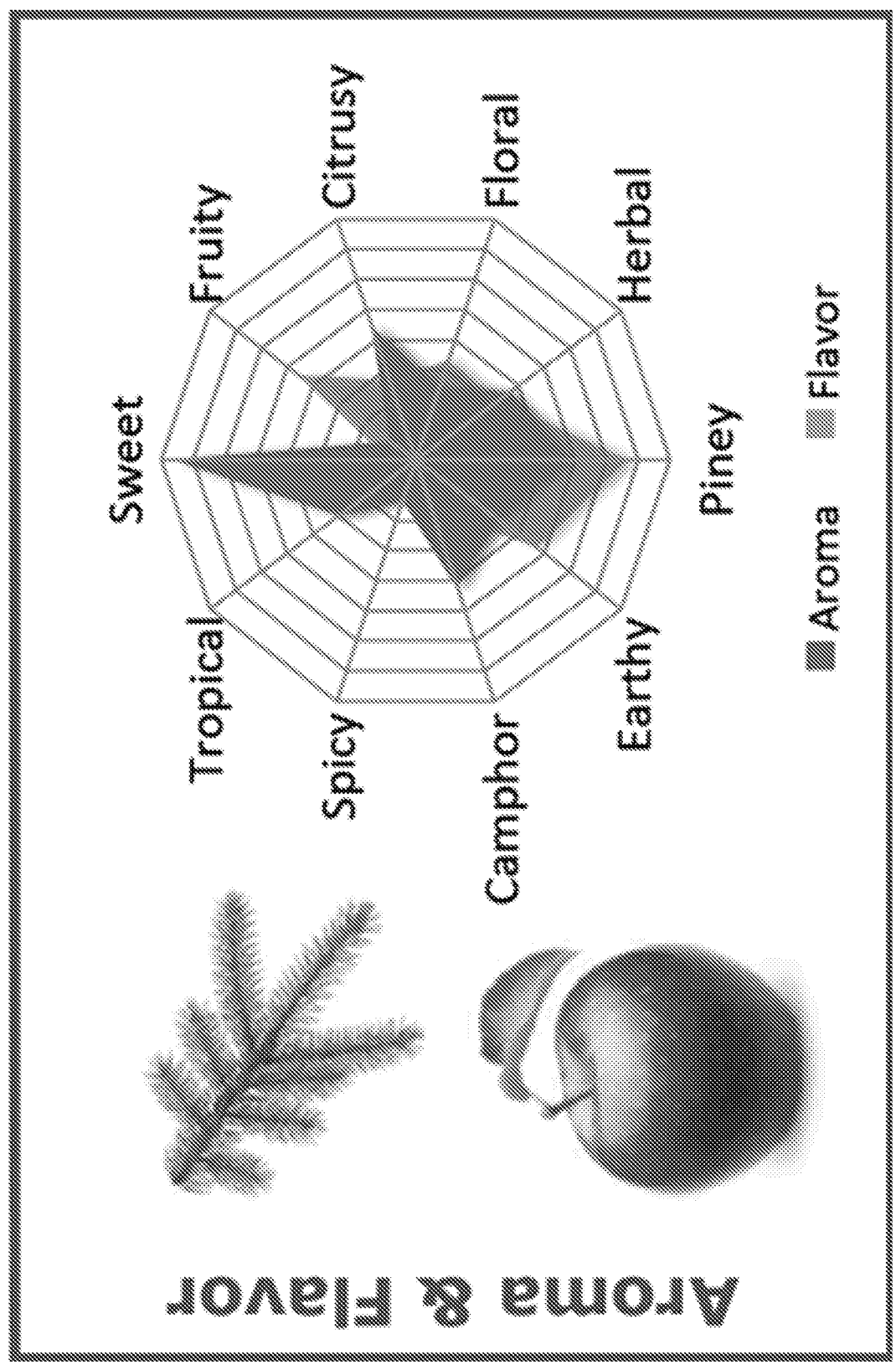
FIG. 9 Depicts an embodiment of a *cannabis* aroma and flavor report. The report stock images represent the two most dominant flavors for the variety. The radar chart indicates the expected aroma and flavor distributions across the organoleptic spectrum. Report is based on the analysis and transformation of terpene content data for the *cannabis* sample.

In order to create a further transform the interpretive flavor and aroma values into an easy to understand chart, the final aroma and flavor values were multiplied by scaling factors as shown in Tables 11 and 12. These values were then used to create a radar chart in excel. A example of the radar chart created in this example is shown in FIG. 9.

Example 11. Preparing a Entourage Effect Report

A chemical analysis was conducted for a sample of *cannabis* variety YLW03 according to the methods described in Example 9. Because the YLW03 variety is a chemotype I plant, only THC was found to accumulate at pharmacologically relevant concentrations. The absolute contents of THC (21.4%) were first multiplied by the THC synergy factor as shown in Table 14.

TABLE 14

| | Multiplication of Absolute THC contents by THC Synergy Factor for Each Terpene | | | | | | | |
|---|---|---|---|---|---|---|---|---|
| | | Synergy Factor | 3 THC Scaled | | | THC Synergy Addition | | |
| # | Analyte | | (mass %) | Focus | Energy | Inspiration | Calm | Comfort | Relaxation |
| 1 | myrcene | | 64.12% | | | | | 64.12% | 64.12% |
| 2 | caryophyllene oxide | | 64.12% | | | | | | |
| 3 | linalool | | 64.12% | | | | | 64.12% | 64.12% |
| 4 | b-caryophyllene | | 64.12% | | | | | | |
| 5 | a-humulene | | 64.12% | | | | | | |
| 6 | a-terpineol | | 64.12% | | | | | | |
| 7 | camphene | | 64.12% | | | | | | |
| 8 | fenchol | | 64.12% | | | | | | |
| 9 | b-pinene | | 64.12% | | | | | | |
| 10 | a-terpinene | | 64.12% | | | | | | |
| 11 | a-pinene | | 64.12% | | | | | | |
| 12 | g-terpinene | | 64.12% | | | | | | |
| 13 | limonene | | 64.12% | | | | | | |
| 14 | carene | | 64.12% | | | | | | |
| 15 | b-oclmene | | 64.12% | | | | | | |
| 16 | a-phellandrene | | 64.12% | | | | | | |
| 17 | terpinolene | | 64.12% | | | | | | |

The resulting values indicated the total multiplication factor that should be applied to the terpene base entourage factors as previously disclosed in Table 7. Thus each of the multiplication factors of Table 14 were added to 100%, and were then multiplied by the terpene base entourage factor for each terpene type to arrive at the weighted entourage loading factors which are shown in Table 15.

TABLE 15

Weighted Entourage Loading Factors, and Final Entourage Effects Values for YLW03

| # | Analyte | Analyte (mass %) | Focus | Energy | Inspiration | Calm | Comfort | Relaxation |
|---|---|---|---|---|---|---|---|---|
| 1 | myrcene | 0.35% | 0 | 0 | 0 | 0.0008865 | 0.00290983 | 0.00581966 |
| 2 | caryophyllene oxide | 0.01% | 0 | 0.000103 | 0 | 0 | 0 | 0 |
| 3 | linalool | 0.05% | 0 | 0 | 0.0002545 | 0.000509 | 0.00020884 | 0.00041768 |
| 4 | b-caryophyllene | 0.23% | 0 | 0 | 0 | 0.001162 | 0.002324 | 0 |
| 5 | a-humulene | 0.06% | 0 | 0 | 0 | 0 | 0.00015325 | 0 |
| 6 | a-terpineol | 0.03% | 0.00008425 | 0.0001685 | 0 | 0 | 0 | 0.00008425 |
| 7 | camphene | 0.00% | 0 | 0 | 0 | 0 | 0 | 0 |
| 8 | fenchol | 0.02% | 0 | 0.000075 | 0 | 0 | 0 | 0 |
| 9 | b-pinene | 0.11% | 0.001122 | 0 | 0.0002805 | 0 | 0.0002805 | 0 |
| 10 | a-terpinene | 0.04% | 0 | 0 | 0 | 0 | 0 | 0 |
| 11 | a-pinene | 0.06% | 0.000627 | 0.00015675 | 0 | 0 | 0.00015675 | 0 |
| 12 | g-terpinene | 0.02% | 0 | 0 | 0 | 0 | 0 | 0 |
| 13 | limonene | 0.16% | 0.00039575 | 0.001583 | 0.0023745 | 0.0007915 | 0 | 0 |
| 14 | carene | 0.04% | 0 | 0 | 0 | 0.0001895 | 0.00009475 | 0 |
| 15 | b-ocimene | 0.32% | 0 | 0 | 0.001578 | 0.003156 | 0 | 0 |
| 16 | a-phellandrene | 0.05% | 0 | 0 | 0 | 0 | 0.0001225 | 0 |
| 17 | terpinolene | 1.05% | 0 | 0.0158175 | 0 | 0.0052725 | 0 | 0 |
| TOT. | Chart Scaling | 20 | 0.04458 | 0.358075 | 0.08975 | 0.23934 | 0.12500843 | 0.12643185 |
|  | Entourage |  | 0.04458 | 0.35808 | 0.08975 | 0.23934 | 0.12501 | 0.12643 |
|  | Scaled Entourage |  | 0.04458 | 0.35808 | 0.08975 | 0.23934 | 0.12501 | 0.12643 |

Figure 10:
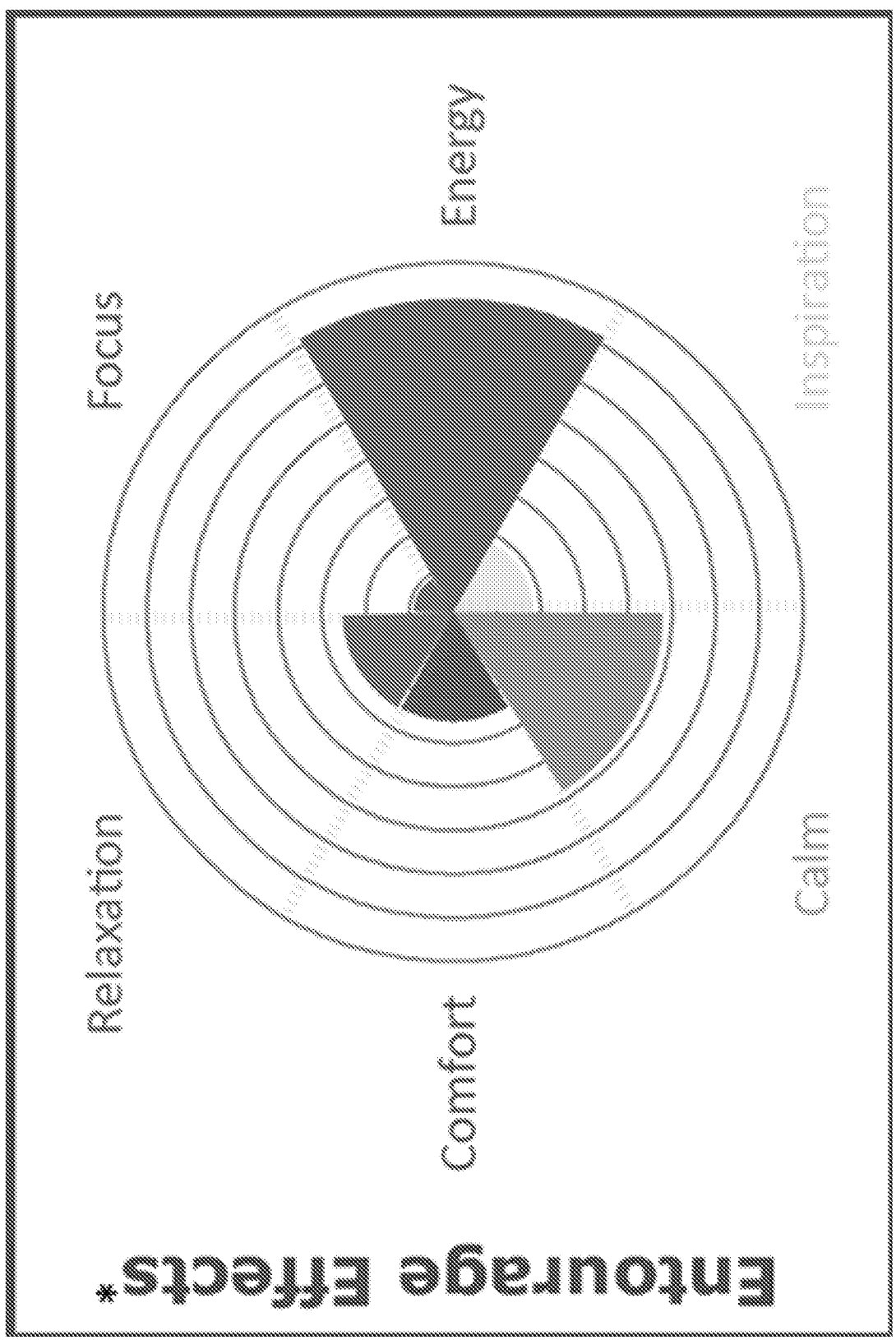
FIG. 10 Depicts an embodiment of a *cannabis* entourage effect report. The pie chart indicates the expected physiological effects of the variety based on the analysis and transformation of terpene and cannabinoid content data for the *cannabis* sample.

In order to create a further transform the entourage effects values into an easy to understand chart, the final entourage effects values were multiplied by scaling factors as shown in Table 15. These values were then used to create modified pie chart in excel. A example of the resulting entourage report chart created in this example is shown in FIG. 10.

Example 11. Consumer Aroma and Flavor Trials

Samples from several popular varieties will be harvested and prepared for consumption. Each of the selected samples will be chemically analyzed as described in Example 9, and aroma and flavor reports will be generated as described in Example 10 and earlier sections of the specification.

Small portions of each of the analyzed samples will then be provided to volunteers who will be asked to rank the flavors or aroma from 1 (most prevalent) to 10 (least prevalent). Aromas or flavors which are undetectable to the volunteers will be left blank.

The trial will be double blinded, with each sample labeled with non-descriptive codes. Once volunteers finish assessing each sample assigned to them, researchers will input the flavor and aroma rankings as determined by the flavor and aroma reports of the present invention.

The correlation between volunteer and report-generated flavor rankings will be compared for accuracy. An example of the expected experimental design is shown in Table 16 below. Sample 1 was filled out with artificially generated data for exemplary purposes.

TABLE 16

Flavor Ranking Data Comparison

| Sample # | Flavor Ranking | Sweet | Fruity | Citrusy | Floral | Herbal | Piney | Earthy | Camphor | Spicy | Tropical |
|---|---|---|---|---|---|---|---|---|---|---|---|
| 1 | Volunteer Ranking | 2 | 1 | 3 |  |  |  | 4 |  |  |  |
|  | Report Ranking | 2 | 1 | 3 |  |  |  | 4 |  |  |  |
| 2 | Volunteer Ranking |  |  |  |  |  |  |  |  |  |  |
|  | Report Ranking |  |  |  |  |  |  |  |  |  |  |
| 3 | Volunteer Ranking |  |  |  |  |  |  |  |  |  |  |
|  | Report Ranking |  |  |  |  |  |  |  |  |  |  |
| 4 | Volunteer Ranking |  |  |  |  |  |  |  |  |  |  |
|  | Report Ranking |  |  |  |  |  |  |  |  |  |  |

Table 17 below shows similar analysis conducted to compare the aroma rankings by volunteers and the reports of the present application. Sample 1 was filled out with artificially generated data for exemplary purposes.

TABLE 17

Aroma Ranking Data Comparison

| Sample # | Aroma Ranking | Sweet | Fruity | Citrusy | Floral | Herbal | Piney | Earthy | Camphor | Spicy | Tropical |
|---|---|---|---|---|---|---|---|---|---|---|---|
| 1 | Volunteer Ranking | 2 | 1 | 3 |  |  |  | 4 |  |  |  |
|  | Report Ranking | 2 | 1 | 3 |  |  |  | 4 |  |  |  |

TABLE 17-continued

Aroma Ranking Data Comparison

| Sample # | Aroma Ranking | Sweet | Fruity | Citrusy | Floral | Herbal | Piney | Earthy | Camphor | Spicy | Tropical |
|---|---|---|---|---|---|---|---|---|---|---|---|
| 2 | Volunteer Ranking | | | | | | | | | | |
|   | Report Ranking | | | | | | | | | | |
| 3 | Volunteer Ranking | | | | | | | | | | |
|   | Report Ranking | | | | | | | | | | |
| 4 | Volunteer Ranking | | | | | | | | | | |
|   | Report Ranking | | | | | | | | | | |

Trials will be conducted with at least 10 volunteers and at least 3 samples per volunteer. Results will be assessed in the form of a correlation chart where X will be the ranking value for a particular aroma or flavor, and Y will be the volunteer-provided ranking for the same sample and aroma or flavor.

Example 12. Aroma Flavor Levels of Human Detection

Volunteer aroma trials will be conducted to determine the limit to which users can distinguish between different terpene profiles.

Volunteers will be provided with several *cannabis* samples with increasingly distinct terpene profiles such that they can initially be divided into two groups based on their dominant terpene, can be further divided into additional groups based on their secondary terpene, and further divided into additional groups due to their tertiary terpene.

Volunteers will be asked to group each sample into an increasingly smaller number of categories based on the aroma and/or flavor of the samples. The volunteer-based classifications will then be compared to the actual differences in the terpene profile of the samples to determine whether users can distinguish samples based on 1, 2, 3 or more terpenes.

An example Table 18 showing the classification experimental design is below. *Cannabis* samples listed in each column are distinguished by different terpene profiles as shown by arbitrary letter codes indicating a the highest, second highest, third highest, and fourth highest-accumulating terpenes in the sample.

The left hand side of each column indicates the proper group assignment based on the measured terpene profile. The right hand side of each column indicates the grouping assignment given from the volunteer. Accuracy will be checked by counting the number of correctly grouped samples. It is expected that accuracy will go down as the samples are further sub-divided.

TABLE 1

Volunteer Classification Limit Experimental Design

| | # of Terpenes Used for Grouping | | |
|---|---|---|---|
| | 1 Terpenes | 2 Terpenes | 3 Terpenes |
| | | | MLPC MLPC |
| | MLFC MLFC | MLPC MLPC | MLFC — |
| | MLFC MLFC | MLPC MLPC | |
| | MLPC MLPC | | MHPC MHPC |
| | MHFC MHFC | MHFC MHFC | |
| | MHPC MHPC | MHPC MHPC | MHFC — |
| | TLPC TLPC | TLPC TLPC | TLPC TLPC |
| | TLFC TLFC | TLFC TLFC | |

TABLE 1-continued

Volunteer Classification Limit Experimental Design

| | # of Terpenes Used for Grouping | | |
|---|---|---|---|
| | 1 Terpenes | 2 Terpenes | 3 Terpenes |
| | THPC THPC | THPC THPC | |
| | THFC THFC | THFC THFC | TLFC TLFC |
| | | THPC THPC | |
| | | THFC — | THPC — |
| | | | THFC THFC |
| Accuracy | 8/8 | 7/8 | 5/8 |

Results from this experiment are expected to show that volunteers can only accurately distinguish up to a maximum of 3 terpenes.

INCORPORATION BY REFERENCE

All references, articles, publications, patents, patent publications, and patent applications cited herein are incorporated by reference in their entireties for all purposes.

However, mention of any reference, article, publication, patent, patent publication, and patent application cited herein is not, and should not be taken as, an acknowledgment or any form of suggestion that they constitute valid prior art or form part of the common general knowledge in any country in the world.

Some embodiments described herein relate to a computer storage product with a non-transitory computer-readable medium (also can be referred to as a non-transitory processor-readable medium) having instructions or computer code thereon for performing various computer-implemented operations. The computer-readable medium (or processor-readable medium) is non-transitory in the sense that it does not include transitory propagating signals per se (e.g., a propagating electromagnetic wave carrying information on a transmission medium such as space or a cable). The media and computer code (also can be referred to as code) may be those designed and constructed for the specific purpose or purposes. Examples of non-transitory computer-readable media include, but are not limited to: magnetic storage media such as hard disks, floppy disks, and magnetic tape; optical storage media such as Compact Disc/Digital Video Discs (CD/DVDs), Compact Disc-Read Only Memories (CD-ROMs), and holographic devices; magneto-optical storage media such as optical disks; carrier wave signal processing modules; and hardware devices that are specially configured to store and execute program code, such as Application-Specific Integrated Circuits (ASICs), Programmable Logic Devices (PLDs), Read-Only Memory (ROM) and Random-Access Memory (RAM) devices. Other embodiments described herein relate to a computer program product, which can include, for example, the instructions and/or computer code discussed herein.

Examples of computer code include, but are not limited to, micro-code or micro-instructions, machine instructions, such as produced by a compiler, and/or files containing higher-level instructions that are executed by a computer using an interpreter. For example, embodiments may be implemented using C, Java, C++, MATLAB or other programming languages and/or other development tools.

The processor(s) can be any processor (e.g., a central processing unit (CPU), an application-specific integrated circuit (ASIC), and/or a field programmable gate array (FPGA)) configured to execute one or more instructions received from, for example, a memory. In some embodiments, the processor(s) can be a Reduced Instruction Set computing (RISC) processor. The processor(s) can be in communication with any of the memory and the network card. In some embodiments, the processor(s) can accordingly send information (e.g., data, instructions and/or network data packets) to and/or receive information from any of the memory and the network card.

The memories disclosed herein can be any memory (e.g., a RAM, a ROM, a hard disk drive, an optical drive, other removable media) configured to store information (e.g., one or more software applications, user account information, media, text, etc.). The memories can include one or more modules performing the functions described herein. In some embodiments, the functions described herein can be performed by any number of modules. For example, in some embodiments, the functions described herein can be performed by a single module.

The memories can also alternatively store one or more resources (e.g., software resources such as drivers, code libraries, etc.) associated with one or more of the modules. The network card can be a hardware module (e.g., a wired and/or wireless Ethernet card, a cellular network interface card) configured to transmit information (e.g., data packets, cells, etc.) from and receive information at the system 100.

While various embodiments have been described above, it should be understood that they have been presented by way of example only, and not limitation. Where methods described above indicate certain events occurring in certain order, the ordering of certain events may be modified. Additionally, certain of the events may be performed concurrently in a parallel process when possible, as well as performed sequentially as described above.

The invention claimed is:

1. A kit, comprising:
 a chemical analyzer configured to:
  (a) receive a sample, the sample including a plurality of terpenes or a plurality of cannabinoids, and
  (b) chemically analyze the sample, including:
   estimating a terpene level of two or more terpenes of the plurality of terpenes in the sample to generate a set of terpene levels, and
   estimating a cannabinoid level of two or more cannabinoids of the plurality of cannabinoids in the sample to generate a set of cannabinoid levels; and
 a computing apparatus operatively coupled to the chemical analyzer, the computing apparatus including:
  a memory configured to:
   receive and store the set of terpene levels and the set of cannabinoid levels, and
   store a set of classification groups; and
  a processor configured to:
   classify the sample to a classification group from the set of classification groups based on the set of terpene levels and the set of cannabinoid levels, the classifying including dividing a relative content of a second-highest accumulating terpene from the plurality of terpenes by a relative content of a primary terpene from the plurality of terpenes to define a modulating factor, the classification group selected based on a comparison of the modulating factor with a predetermined contribution factor, and
   transmit an alphanumeric sequence to an output interface of the processor based on the classification group from the set of classification groups, the alphanumeric sequence including a representation of a terpene classification of the sample followed by a representation of a cannabinoid classification of the sample.

2. The kit of claim 1, wherein the modulating factor is a first modulating factor, the classifying further including dividing a relative content of a third-highest accumulating terpene from the plurality of terpenes by the relative content of the primary terpene to define a second modulating factor, the classification group including the primary terpene and at least one of:
 the second-highest accumulating terpene when the first modulating factor is equal to or greater than the predetermined contribution factor; or
 the third-highest accumulating terpene when the second modulating factor is equal to or greater than the predetermined contribution factor.

3. The kit of claim 1, the sample including one or more *cannabis* species, each *cannabis* species selected from the group consisting of *Cannabis sativa, Cannabis indica*, and *Cannabis ruderalis*.

4. The kit of claim 1, the processor further configured to classify the sample based on at least one of a highest terpene level of the set of terpene levels, or a highest cannabinoid level of the set of cannabinoid levels.

5. The kit of claim 1, the processor further configured to classify the sample based on at least one of:
 two or more terpene levels of the set of terpene levels, the two or more terpene levels including a first terpene level and a second terpene level, the first terpene level being the highest terpene level of the set of terpene levels, the second terpene level being lesser than the first terpene level and greater than a remainder of the set of terpene levels, or
 two or more cannabinoid levels of the set of cannabinoid levels, the two or more cannabinoid levels including a first cannabinoid level and a second cannabinoid level, the first cannabinoid level being the highest cannabinoid level of the set of cannabinoid levels, the second cannabinoid level being lesser than the first cannabinoid level and greater than a remainder of the set of cannabinoid levels.

6. An apparatus, comprising:
 a housing;
 a chemical analyzer disposed within the housing and configured to:
  receive a sample, the sample including a plurality of terpenes and a plurality of cannabinoids;
  chemically analyze the sample, including:
   estimating a terpene level of two or more terpenes of the plurality of terpenes in the sample to generate a set of terpene levels, and
   estimating a cannabinoid level of two or more cannabinoids of the plurality of cannabinoids in the sample to generate a set of cannabinoid levels;
 a classifier disposed within the housing and implemented in one of a memory or a processing device, the classifier communicably coupled to the chemical analyzer, the classifier configured to classify the sample to a classification group from a set of classification groups based on the set of terpene levels and the set of cannabinoid levels, the classifying including dividing a relative content of a second-highest accumulating terpene from the plurality of terpenes by a relative content of a primary terpene from the plurality of terpenes to define a modulating factor, the classification group selected based on a comparison of the modulating factor with a predetermined contribution factor; and a sequence generator disposed within the housing and configured to generate and transmit an alphanumeric sequence based on the classification group from the set of classification groups, the alphanumeric sequence including a representation of a terpene classification of the sample followed by a representation of a cannabinoid classification of the sample.

7. The apparatus of claim 6, wherein the modulating factor is a first modulating factor, the classifying further including dividing a relative content of a third-highest accumulating terpene from the plurality of terpenes by the relative content of the primary terpene to define a second modulating factor, the classification group including the primary terpene and at least one of:
the second-highest accumulating terpene when the first modulating factor is equal to or greater than the predetermined contribution factor; or
the third-highest accumulating terpene when the second modulating factor is equal to or greater than the predetermined contribution factor.

8. The apparatus of claim 6, the sample including one or more *cannabis* species, each *cannabis* species selected from the group consisting of *Cannabis sativa, Cannabis indica,* and *Cannabis ruderalis*.

9. The apparatus of claim 6, the classifier further configured to classify the sample based on at least one of: a highest terpene level of the set of terpene levels, or a highest cannabinoid level of the set of cannabinoid levels.

10. The apparatus of claim 6, the classifier further configured to classify the sample based on at least one of:
at least two terpene levels of the set of terpene levels, the at least two terpene levels including a first terpene level and a second terpene level, the first terpene level being the highest terpene level of the set of terpene levels, the second terpene level being lesser than the first terpene level and greater than a remainder of the set of terpene levels, or
at least two cannabinoid levels of the set of cannabinoid levels, the at least two cannabinoid levels including a first cannabinoid level and a second cannabinoid level, the first cannabinoid level being the highest cannabinoid level of the set of cannabinoid levels, the second cannabinoid level being lesser than the first cannabinoid level and greater than a remainder of the set of cannabinoid levels.

11. The apparatus of claim 6, the classifier configured to classify the sample using bottom up hierarchical classification.

12. The apparatus of claim 6, the classifier configured to classify the sample using a agglomerative hierarchical clustering approach.

13. A method, comprising:
chemically analyzing, via a chemical analyzer, a sample including a plurality of terpenes and a plurality of cannabinoids, the chemically analyzing including:
estimating a terpene level of at least two terpenes of the plurality of terpenes in the sample to generate a set of terpene levels, and
estimating a cannabinoid level of at least two cannabinoids of the plurality of cannabinoids in the sample to generate a set of cannabinoid levels;
classifying the sample to a classification group from a set of classification groups based on the set of terpene levels and the set of cannabinoid levels, the classifying including dividing a relative content of a second-highest accumulating terpene from the plurality of terpenes by a relative content of a primary terpene from the plurality of terpenes to define a modulating factor, the classification group selected based on a comparison of the modulating factor with a predetermined contribution factor; and
transmitting an alphanumeric sequence based on the classification group from the set of classification groups, the alphanumeric sequence including a representation of a terpene classification of the sample followed by a representation of a cannabinoid classification of the sample.

14. The method of claim 13, wherein the modulating factor is a first modulating factor, the classifying further including dividing a relative content of a third-highest accumulating terpene from the plurality of terpenes by the relative content of the primary terpene to define a second modulating factor.

15. The method of claim 14, wherein the classification group includes the primary terpene and at least one of:
the second-highest accumulating terpene when the first modulating factor is equal to or greater than the predetermined contribution factor; or
the third-highest accumulating terpene when the second modulating factor is equal to or greater than the predetermined contribution factor.

16. The method of claim 13, the sample including one or more *cannabis* species, each *cannabis* species selected from the group consisting of *Cannabis sativa, Cannabis indica,* and *Cannabis ruderalis*.

17. The method of claim 13, the classifying including classifying the sample based on at least one of: a highest terpene level of the set of terpene levels, or a highest cannabinoid level of the set of cannabinoid levels.

18. The method of claim 13, the classifying the sample based on at least one of:
at least two terpene levels of the set of terpene levels, the at least two terpene levels including a first terpene level and a second terpene level, the first terpene level being the highest terpene level of the set of terpene levels, the second terpene level being lesser than the first terpene level and greater than a remainder of the set of terpene levels, or
at least two cannabinoid levels of the set of cannabinoid levels, the at least two cannabinoid levels including a first cannabinoid level and a second cannabinoid level, the first cannabinoid level being the highest cannabinoid level of the set of cannabinoid levels, the second cannabinoid level being lesser than the first cannabinoid level and greater than a remainder of the set of cannabinoid levels.

19. The method of claim 13, wherein:
the chemically analyzing includes generating the set of terpene levels;
the set of terpene levels is a set of absolute terpene levels; and the classifying includes:
generating a set of relative terpene levels based on the set of absolute terpene levels, and
classifying the sample based on the set of relative terpene levels.

20. The method of claim 13, wherein the classifying includes classifying the sample using an agglomerative hierarchical clustering (AHC) analysis.

21. The method of claim 20, wherein the classifying further includes pruning the AHC analysis after detecting 40% similarity between members of the classification group.

* * * * *